(12) United States Patent
Probst et al.

(10) Patent No.: US 6,555,115 B1
(45) Date of Patent: Apr. 29, 2003

(54) COMPOUNDS AND METHODS FOR TREATMENT AND DIAGNOSIS OF CHLAMYDIAL INFECTION

(75) Inventors: Peter Probst, Seattle, WA (US); Ajay Bhatia, Seattle, WA (US); Yasir A. W. Skeiky, Seattle, WA (US); Shyian Jen, Seattle, WA (US); Erika Jean Stromberg, Seattle, WA (US)

(73) Assignee: Corixa Corporation, Seattle, WA (US)

( * ) Notice: Subject to any disclaimer, the term of this patent is extended or adjusted under 35 U.S.C. 154(b) by 0 days.

(21) Appl. No.: 09/410,568

(22) Filed: Oct. 1, 1999

Related U.S. Application Data

(63) Continuation-in-part of application No. 09/288,594, filed on Apr. 8, 1999, now Pat. No. 6,447,779, which is a continuation-in-part of application No. 09/208,277, filed on Dec. 8, 1998, now Pat. No. 6,166,177.

(51) Int. Cl.$^7$ .................. A61K 39/118; A61K 39/02; A61K 38/00; C07K 2/00; A01N 37/18

(52) U.S. Cl. .................. 424/263.1; 424/234.1; 424/184.1; 424/185.1; 514/2; 530/300; 530/324; 530/325; 530/326; 530/350

(58) Field of Search .................. 424/185.1, 184.1, 424/234.1, 263.1; 530/350, 300, 324, 325, 326; 514/2

(56) References Cited

U.S. PATENT DOCUMENTS

| | | | |
|---|---|---|---|
| 4,118,469 A | | 10/1978 | Caldwell et al. ............... 424/1 |
| 4,497,863 A | | 2/1985 | Armstrong et al. ......... 436/510 |
| 5,166,053 A | | 11/1992 | Huguenel et al. .......... 435/7.36 |
| 5,318,892 A | | 6/1994 | Watanabe et al. .......... 435/7.36 |
| 5,725,863 A | | 3/1998 | Daniels et al. ........... 424/263.1 |
| 6,166,177 A | * | 12/2000 | Probst et al. |
| 6,432,916 B1 | * | 8/2002 | Probst et al. .................. 514/2 |
| 6,447,779 B1 | * | 9/2002 | Probst et al. ............ 424/190.1 |
| 6,448,234 B1 | * | 9/2002 | Fling ............................ 514/44 |
| 2002/0061848 A1 | * | 5/2002 | Bhatia et al. ................. 514/12 |
| 2002/0146776 A1 | * | 10/2002 | Bhatia et al. .............. 435/69.3 |

FOREIGN PATENT DOCUMENTS

| | | | |
|---|---|---|---|
| EP | 348725 | * | 3/1990 |
| EP | 0784 059 A | | 7/1997 |
| WO | WO 94/06827 | * | 3/1994 |
| WO | WO 97/06263 | | 2/1997 |
| WO | WO 98/02546 | | 1/1998 |
| WO | WO 98/10789 | | 3/1998 |
| WO | WO 99/27105 | | 6/1999 |
| WO | WO 99/28475 | | 6/1999 |
| WO | WO 99/28475 A | | 6/1999 |
| WO | WO 99/51748 | | 10/1999 |
| WO | WO 00/34483 | | 6/2000 |
| WO | WO 01/40474 | | 6/2001 |

OTHER PUBLICATIONS

Stephens et al., "Genome Sequence of an Obligate Intracellular Pathogen of Humans: *Chlamydia trachomatis*," *Science* 282: 754–759, 1998.

Levinson and Jawetz, *Medical Microbiology & Immunology*, 3d ed., Appleton & Lange, 1994, pp. 292–293.

GenBank Accession No. AE001273, "Genome sequence of an obligate intracellular pathogen of humans: *Chlamydia trachomatis*," Oct. 30, 1999.

GenBank Accession No. AE001323, "Genome sequence of an obligate intracellular pathogen of humans: *Chlamydia trachomatis*," Oct. 30, 1999.

GenBank Accession No. AE001324, "Genome sequence of an obligate intracellular pathogen of humans: *Chlamydia trachomatis*," Oct. 30, 1999.

GenBank Accession No. AE001335, "Genome sequence of an obligate intracellular pathogen of humans: *Chlamydia trachomatis*," Oct. 30, 1999.

GenBank Accession No. E71500, "Genome sequence of an obligate intracellular pathogen of humans: *Chlamydia trachomatis*," Oct. 8, 1999.

GenBank Accession No. H71501, "Genome sequence of an obligate intracellular pathogen of humans: *Chlamydia trachomatis*," Oct. 8, 1999.

GenBank Accession No. H71510, "Genome sequence of an obligate intracellular pathogen of humans: *Chlamydia trachomatis*," Oct. 8, 1999.

Rank et al., *Infect. And Immunity*, 58(8):2599–2605, 1990.

Genbank Accession No. AE001316.

Genbank Accession No. AE001320.

Genbank Accession No. AE001326.

Gu et al., "*Chlamydia trachomatis* RNA polymerase α subunit: sequence and structural analysis," *J. Bacteriology* 177:2594–2601, May 1995.

Sanderson et al., "Identification of a CD4$^+$ T Cell–stimulating Antigen of Pathogenic Bacteria by Expression Cloning," *J. Exp. Med.* 182(6):1751–1757, 1995.

Scudiero et al., "Evaluation of a soluble tetrazolium/formazan assay for cell growth and drug sensitivity in culture using human and other tumor cell lines," *Cancer Research* 48:4827–4833, Sep. 1, 1988.

(List continued on next page.)

*Primary Examiner*— Nita Minnifield
(74) *Attorney, Agent, or Firm*—Seed Intellectual Property Law Group PLLC

(57) ABSTRACT

Compounds and methods for the diagnosis and treatment of Chlamydial infection are disclosed. The compounds provided include polypeptides that contain at least one antigenic portion of a Chlamydia antigen and DNA sequences encoding such polypeptides. Pharmaceutical compositions and vaccines comprising such polypeptides or DNA sequences are also provided, together with antibodies directed against such polypeptides. Diagnostic kits containing such polypeptides or DNA sequences and a suitable detection reagent may be used for the detection of Chlamydial infection in patients and in biological samples.

3 Claims, 11 Drawing Sheets

OTHER PUBLICATIONS

Baehr et al., "Mapping antigenic domains expressed by *chlamydia trachomatis* major outer membrane protein genes," *Proc Natl Acad Sci USA* 85(1):4000–4004, Jun. 1, 1988.
Brunham et al., "*Chlamydia trachomatis* antigens: role in immunity and pathogenesis," *Infectious Agents and Disease* 3(5):218–233, Oct. 1994.
Genbank Accession No. AE001361, Jul. 22, 1998.
Read et al N.A. Research 28/6: 1397–1406, 2000.*
Grimwood et al Infection & Immunity 69/4: 2383–2389, 2001.*
Pawlikowska et al Central–European J of Immunology, 24: 293–298, 1999.*
Kalman et al Nature Genetics 21: 385–389, 1999.*
Lu et al. Infection & Immunity 67/4: 1763–1769, 1999.*
Shirai et al, N. A. Research 28/12: 2311–2314, 2000.*
Zhong et al. J. Industrial Microbial & Biotechnology 19:71–76, 1997.*
Murdin et al Infection & Immunity 61/10: 4406–4414, 1993.*
Zhong et al. J. Immunology 151/7: 3728–3736, 1993.*
Pal et al, Infection & Immunity 65/8:3361–3369, 1997.*
Coulan et al, J. General Microbiology 136: 2013–2020, 1990.*
Kwon et al, Arthritis & Rheumatism 40/5: 945–954, 1997.*
Zhong et al, JBC 269/39: 24183–24188, 1994.*
Hayes et al, J. General Microbiology 136 :1559–1566, 1990.*
Peterson et al, Molecular Immunology 33/4–5: 335–339, 1996.*
Peterson et al Infection & Immunity 64/8: 3354–3359, 1996.*
Su et al, Vaccine 13/11: 1023–1032, 1995.*
Su et al Vaccine 11/11: 1159–1166, 1993.*
Allen et al Eur. J Immunol. 23: 1169–1172, 1993.*
Hayes et al, J. Gen. Microbiology 137: 1557–1564, 1991.*

* cited by examiner

PRIMER SEQUENCES-CP SWIB AND CP S13

CP SWIB Nde (5' primer)
5' GATATACATATGCATCACCATCACCATCACATGAGTCAAAAAAATAAAAACTCT CP SWIB EcoRI (3' primer)
5' CTCGAGGAATTCTTATTTTACAATATGTTTGGA CP S13 Nde (5' primer)
5' GATATACATATGCATCACCATCACCATCACATGCCACGCATCATTGGAATGAT CP S13 EcoRI (3' primer)
5' CTCGAGGAATTCTTATTTCTTCTTACCTGC

*Fig. 6*

T cell line TCL-8 EBCD responds to *E. coli* expressing ribosomal S13 from *C. trachomatis* and from *C. pneumoniae*

T cell line TCL-8 EBCD responds to *E. coli* expressing SWIB from *C. trachomatis* but not from *C. pneumoniae*

Identification of T cell epitopes in chlamydial ribosomal S13 protein with TCL8 EB/DC
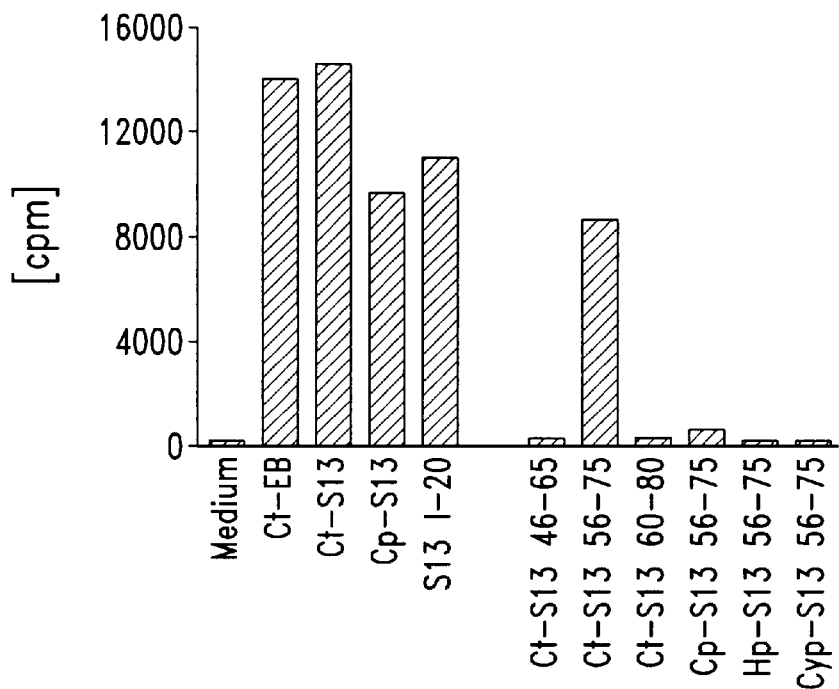
Proliferative responses were determined by stimulating 2.5 x $10^4$ T cells in the pressence of 1 x $10^4$ monocyte-derived dendritic cells and Ct-EB (1 $\mu$g/ml), Ct-, CpS13 (2 $\mu$g/ml) or the respective peptide (0.2 $\mu$g/ml). Assay was harvested after 4 days with a $^3$H-thymidine pulse for the last 18h.
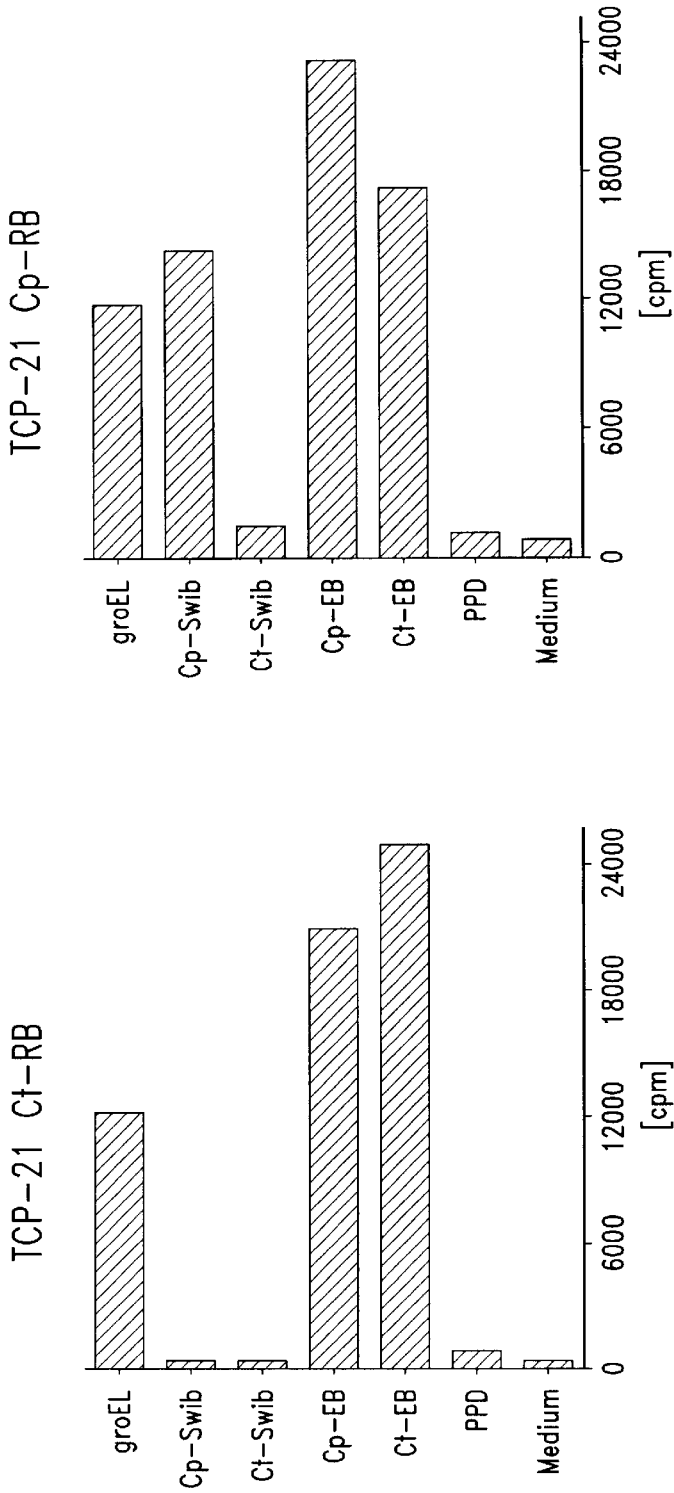

A primary T cell line (TCT-10 EB) from an asymptomatic donor has a *C. trachomatis*-specific Swib response

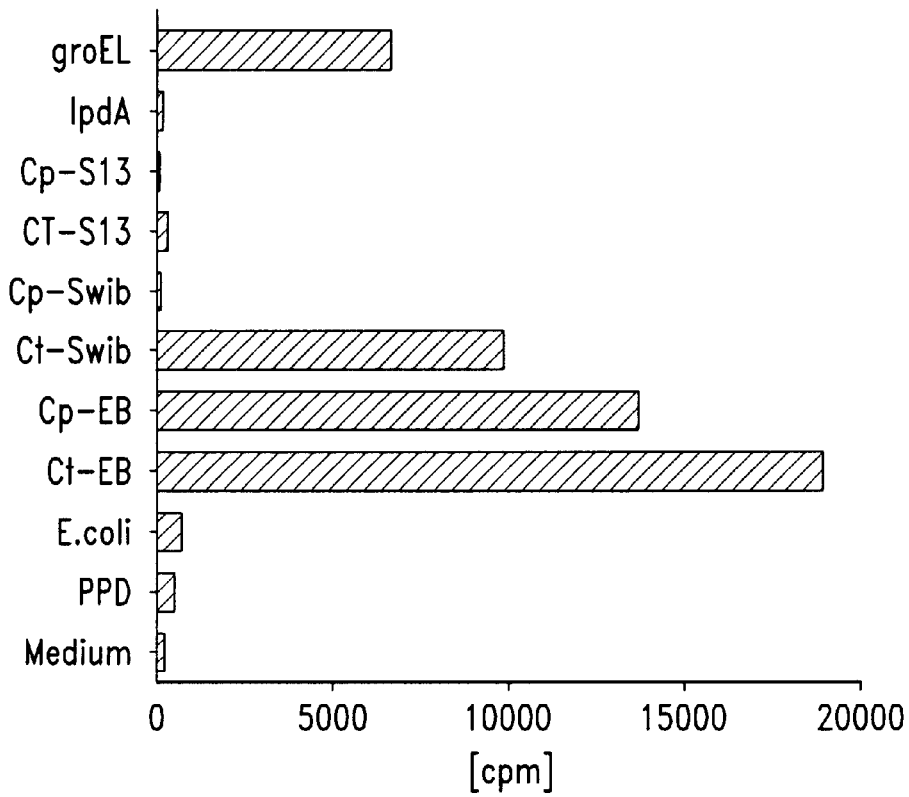

T cell line TCT-10 EB was generated by stimulating PBMC with 1 μg/ml killed C. trachomatis LGV2 elementary body (EB). Proliverative responses were determined by stimulating 2.5 x $10^4$ T cells in the presence of 1 x $10^4$ monocyte-derived dendritic cells and the respective antigen. Assay was harvested after 4 days with a $^3$H-thymidine pulse for the last 18h.

*Fig. 10*

Identification of T cell epitope in C. trachomatis Swib with TCL-10 EB

[Bar chart with y-axis labeled [cpm] ranging 0 to 32000, showing bars for: Medium, CTSWIB, CTSWIB 43-61, CTSWIB 48-67, CTSWIB 52-71, CTSWIB 58-77, CTSWIB 63-82, CTSWIB 52-67, CPSWIB 53-68, CTSWIB 51-66, CPSWIB 52-67, HuSWI 288-302, CPSWI-T 828-842, CTSWI-T 822-837]

Proliferative responses were determined by stimulating 2.5 × $10^4$ T cells in the presence of 1 × $10^4$ monocyte-derived dendritic cells and Ct-Swib 2 g/ml or the respective peptide 0.2 µg/ml. Assay was harvested after 4 days with a $^3$H-thymidine pulse for the last 18h.

SEQUENCE LISTING

<160> NUMBER OF SEQ ID NOS: 109

<210> SEQ ID NO 1
<211> LENGTH: 481
<212> TYPE: DNA
<213> ORGANISM: Chlamydia trachomatis

<400> SEQUENCE: 1

| | | | | | |
|---|---|---|---|---|---|
| ctgaagactt | ggctatgttt | tttattttga | cgataaacct | agttaaggca | taaaagagtt | 60 |
| gcgaaggaag | agccctcaac | ttttcttatc | accttcttta | actaggagtc | atccatgagt | 120 |
| caaaataaga | actctgcttt | catgcagcct | gtgaacgtat | ccgctgattt | agctgccatc | 180 |
| gttggtgcag | gacctatgcc | tcgcacagag | atcattaaga | aaatgtggga | ttacattaag | 240 |
| gagaatagtc | ttcaagatcc | tacaaacaaa | cgtaatatca | atcccgatga | taaattggct | 300 |
| aaagtttttg | gaactgaaaa | acctatcgat | atgttccaaa | tgacaaaaat | ggtttctcaa | 360 |
| cacatcatta | aataaaatag | aaattgactc | acgtgttcct | cgtctttaag | atgaggaact | 420 |
| agttcattct | ttttgttcgt | ttttgtgggt | attactgtat | ctttaacaac | tatcttagca | 480 |
| g | | | | | | 481 |

<210> SEQ ID NO 2
<211> LENGTH: 183
<212> TYPE: DNA
<213> ORGANISM: Chlamydia trachomatis

<400> SEQUENCE: 2

| | | | | | |
|---|---|---|---|---|---|
| atcgttggtg | caggacctat | gcctcgcaca | gagatcatta | agaaaatgtg | ggattacatt | 60 |
| aaggagaata | gtcttcaaga | tcctacaaac | aaacgtaata | tcaatcccga | tgataaattg | 120 |
| gctaaagttt | ttggaactga | aaaacctatc | gatatgttcc | aaatgacaaa | aatggtttct | 180 |
| caa | | | | | | 183 |

<210> SEQ ID NO 3
<211> LENGTH: 110
<212> TYPE: DNA
<213> ORGANISM: Chlamydia trachomatis

<400> SEQUENCE: 3

| | | | | | |
|---|---|---|---|---|---|
| gctgcgacat | catgcgagct | tgcaaaccaa | catggacatc | tccaatttcc | ccttctaact | 60 |
| cgctctttgg | aactaatgct | gctaccgagt | caatcacaat | cacatcgacc | | 110 |

<210> SEQ ID NO 4
<211> LENGTH: 555

<212> TYPE: DNA
<213> ORGANISM: Chlamydia trachomatis

<400> SEQUENCE: 4

```
cggcacgagc ctaagatgct tatactactt taagggaggc ccttcgtatg ccgcgcatca      60
ttggaataga tattcctgcg aaaaagaaat taaaaataag tcttacatat atttatggaa     120
tagggccagc tctttctaaa gagattattg ctagattgca gttgaatccc gaagctagag     180
ctgcagagtt gactgaggaa gaggttggtc gactaaacgc tcttttacag tcggattacg     240
ttgttgaagg ggatttgcgc cgtcgtgtgc aatctgatat caaacgtctg attactatcc     300
atgcttatcg tggacaaaga catagacttt ctttgcctgt tcgtggtcag agaacaaaaa     360
caaattctcg cacgcgtaag ggtaaacgta aaactattgc aggtaagaag aataataat     420
ttttaggaga gagtgttttg gttaaaaatc aagcgcaaaa aagaggcgta aaaagaaaac     480
aagtaaaaaa cattccttcg ggcgttgtcc atgttaaggc tacttttaat aatacaattg     540
taaccataac agacc                                                      555
```

<210> SEQ ID NO 5
<211> LENGTH: 86
<212> TYPE: PRT
<213> ORGANISM: Chlamydia trachomatis

<400> SEQUENCE: 5

```
Met Ser Gln Asn Lys Asn Ser Ala Phe Met Gln Pro Val Asn Val Ser
  1               5                  10                  15

Ala Asp Leu Ala Ala Ile Val Gly Ala Gly Pro Met Pro Arg Thr Glu
             20                  25                  30

Ile Ile Lys Lys Met Trp Asp Tyr Ile Lys Glu Asn Ser Leu Gln Asp
         35                  40                  45

Pro Thr Asn Lys Arg Asn Ile Asn Pro Asp Asp Lys Leu Ala Lys Val
     50                  55                  60

Phe Gly Thr Glu Lys Pro Ile Asp Met Phe Gln Met Thr Lys Met Val
 65                  70                  75                  80

Ser Gln His Ile Ile Lys
                 85
```

<210> SEQ ID NO 6
<211> LENGTH: 61
<212> TYPE: PRT
<213> ORGANISM: Chlamydia trachomatis

<400> SEQUENCE: 6

```
Ile Val Gly Ala Gly Pro Met Pro Arg Thr Glu Ile Ile Lys Lys Met
  1               5                  10                  15

Trp Asp Tyr Ile Lys Glu Asn Ser Leu Gln Asp Pro Thr Asn Lys Arg
             20                  25                  30

Asn Ile Asn Pro Asp Asp Lys Leu Ala Lys Val Phe Gly Thr Glu Lys
         35                  40                  45

Pro Ile Asp Met Phe Gln Met Thr Lys Met Val Ser Gln
     50                  55                  60
```

<210> SEQ ID NO 7
<211> LENGTH: 36
<212> TYPE: PRT
<213> ORGANISM: Chlamyida trachomatis

<400> SEQUENCE: 7

-continued

```
Ala Ala Thr Ser Cys Glu Leu Ala Asn Gln His Gly His Leu Gln Phe
 1               5                  10                  15

Pro Leu Leu Thr Arg Ser Leu Glu Leu Met Leu Leu Pro Ser Gln Ser
                20                  25                  30

Gln Ser His Arg
        35

<210> SEQ ID NO 8
<211> LENGTH: 18
<212> TYPE: PRT
<213> ORGANISM: Chlamydia trachomatis

<400> SEQUENCE: 8

Leu Arg His His Ala Ser Leu Gln Thr Asn Met Asp Ile Ser Asn Phe
 1               5                  10                  15

Pro Phe

<210> SEQ ID NO 9
<211> LENGTH: 5
<212> TYPE: PRT
<213> ORGANISM: Chlamydia trachomatis

<400> SEQUENCE: 9

Leu Ala Leu Trp Asn
 1               5

<210> SEQ ID NO 10
<211> LENGTH: 11
<212> TYPE: PRT
<213> ORGANISM: Chlamydia trachomatis

<400> SEQUENCE: 10

Cys Cys Tyr Arg Val Asn His Asn His Ile Asp
 1               5                  10

<210> SEQ ID NO 11
<211> LENGTH: 36
<212> TYPE: PRT
<213> ORGANISM: Chlamydia trachomatis

<400> SEQUENCE: 11

Val Asp Val Ile Val Ile Asp Ser Val Ala Ala Leu Val Pro Lys Ser
 1               5                  10                  15

Glu Leu Glu Gly Glu Ile Gly Asp Val His Val Gly Leu Gln Ala Arg
                20                  25                  30

Met Met Ser Gln
        35

<210> SEQ ID NO 12
<211> LENGTH: 122
<212> TYPE: PRT
<213> ORGANISM: Chlamydia trachomatis

<400> SEQUENCE: 12

Met Pro Arg Ile Ile Gly Ile Asp Ile Pro Ala Lys Lys Leu Lys
 1               5                  10                  15

Ile Ser Leu Thr Tyr Ile Tyr Gly Ile Gly Pro Ala Leu Ser Lys Glu
                20                  25                  30

Ile Ile Ala Arg Leu Gln Leu Asn Pro Glu Ala Arg Ala Ala Glu Leu
        35                  40                  45

Thr Glu Glu Glu Val Gly Arg Leu Asn Ala Leu Leu Gln Ser Asp Tyr
```

```
                    50                  55                  60
Val Val Glu Gly Asp Leu Arg Arg Arg Val Gln Ser Asp Ile Lys Arg
 65                  70                  75                  80

Leu Ile Thr Ile His Ala Tyr Arg Gly Gln Arg His Arg Leu Ser Leu
                 85                  90                  95

Pro Val Arg Gly Gln Arg Thr Lys Thr Asn Ser Arg Thr Arg Lys Gly
            100                 105                 110

Lys Arg Lys Thr Ile Ala Gly Lys Lys Lys
        115                 120

<210> SEQ ID NO 13
<211> LENGTH: 20
<212> TYPE: PRT
<213> ORGANISM: Chlamydia trachomatis

<400> SEQUENCE: 13

Asp Pro Thr Asn Lys Arg Asn Ile Asn Pro Asp Lys Leu Ala Lys
 1               5                  10                  15

Val Phe Gly Thr
             20

<210> SEQ ID NO 14
<211> LENGTH: 20
<212> TYPE: PRT
<213> ORGANISM: Chlamydia trachomatis

<400> SEQUENCE: 14

Asp Asp Lys Leu Ala Lys Val Phe Gly Thr Glu Lys Pro Ile Asp Met
 1               5                  10                  15

Phe Gln Me Thr
         20

<210> SEQ ID NO 15
<211> LENGTH: 161
<212> TYPE: DNA
<213> ORGANISM: Chlymidia trachomatis

<400> SEQUENCE: 15
atctttgtgt gtctcataag cgcagagcgg ctgcggctgt ctgtagcttc atcggaggaa    60
ttacctacct cgcgacattc ggagctatcc gtccgattct gtttgtcaac aaaatgctgg   120
cgcaaccgtt tctttcttcc caaactaaag caaatatggg a                       161

<210> SEQ ID NO 16
<211> LENGTH: 897
<212> TYPE: DNA
<213> ORGANISM: Chlymidia trachomatis

<400> SEQUENCE: 16
atggcttcta tatgcggacg tttagggtct ggtacaggga atgctctaaa agcttttttt    60
acacagccca acaataaaat ggcaagggta gtaaataaga cgaagggaat ggataagact   120
attaaggttg ccaagtctgc tgccgaattg accgcaaata ttttggaaca agctggaggc   180
gcgggctctt ccgcacacat tacagcttcc caagtgtcca aaggattagg ggatgcgaga   240
actgttgtcg ctttagggaa tgcctttaac ggagcgttgc caggaacagt tcaaagtgcg   300
caaagcttct tctctcacat gaaagctgct agtcagaaaa cgcaagaagg ggatgagggg   360
ctcacagcag atctttgtgt gtctcataag cgcagagcgg ctgcggctgt ctgtagcatc   420
atcggaggaa ttacctacct cgcgacattc ggagctatcc gtccgattct gtttgtcaac   480
```

-continued

```
aaaatgctgg caaaaccgtt tctttcttcc caaactaaag caaatatggg atcttctgtt     540
agctatatta tggcggctaa ccatgcagcg tctgtggtgg gtgctggact cgctatcagt     600
gcggaaagag cagattgcga agcccgctgc gctcgtattg cgagagaaga gtcgttactc     660
gaagtgccgg gagaggaaaa tgcttgcgag aagaaagtcg ctggagagaa agccaagacg     720
ttcacgcgca tcaagtatgc actcctcact atgctcgaga gttttttgga atgcgttgcc     780
gacgttttca aattggtgcc gctgcctatt acaatgggta ttcgtgcgat tgtggctgct     840
ggatgtacgt tcacttctgc aattattgga ttgtgcactt tctgcgccag agcataa       897
```

<210> SEQ ID NO 17
<211> LENGTH: 298
<212> TYPE: PRT
<213> ORGANISM: Chlamydia trachomatis

<400> SEQUENCE: 17

```
Met Ala Ser Ile Cys Gly Arg Leu Gly Ser Gly Thr Gly Asn Ala Leu
 1               5                  10                  15

Lys Ala Phe Phe Thr Gln Pro Asn Asn Lys Met Ala Arg Val Val Asn
            20                  25                  30

Lys Thr Lys Gly Met Asp Lys Thr Ile Lys Val Ala Lys Ser Ala Ala
        35                  40                  45

Glu Leu Thr Ala Asn Ile Leu Glu Gln Ala Gly Gly Ala Gly Ser Ser
    50                  55                  60

Ala His Ile Thr Ala Ser Gln Val Ser Lys Gly Leu Gly Asp Ala Arg
65                  70                  75                  80

Thr Val Val Ala Leu Gly Asn Ala Phe Asn Gly Ala Leu Pro Gly Thr
                85                  90                  95

Val Gln Ser Ala Gln Ser Phe Phe Ser His Met Lys Ala Ala Ser Gln
            100                 105                 110

Lys Thr Gln Glu Gly Asp Glu Gly Leu Thr Ala Asp Leu Cys Val Ser
        115                 120                 125

His Lys Arg Arg Ala Ala Ala Val Cys Ser Ile Ile Gly Gly Ile
    130                 135                 140

Thr Tyr Leu Ala Thr Phe Gly Ala Ile Arg Pro Ile Leu Phe Val Asn
145                 150                 155                 160

Lys Met Leu Ala Lys Pro Phe Leu Ser Ser Gln Thr Lys Ala Asn Met
                165                 170                 175

Gly Ser Ser Val Ser Tyr Ile Met Ala Ala Asn His Ala Ala Ser Val
            180                 185                 190

Val Gly Ala Gly Leu Ala Ile Ser Ala Glu Arg Ala Asp Cys Glu Ala
        195                 200                 205

Arg Cys Ala Arg Ile Ala Arg Glu Glu Ser Leu Leu Glu Val Pro Gly
    210                 215                 220

Glu Glu Asn Ala Cys Glu Lys Lys Val Ala Gly Glu Lys Ala Lys Thr
225                 230                 235                 240

Phe Thr Arg Ile Lys Tyr Ala Leu Leu Thr Met Leu Glu Lys Phe Leu
                245                 250                 255

Glu Cys Val Ala Asp Val Phe Lys Leu Val Pro Leu Pro Ile Thr Met
            260                 265                 270

Gly Ile Arg Ala Ile Val Ala Ala Gly Cys Thr Phe Thr Ser Ala Ile
        275                 280                 285

Ile Gly Leu Cys Thr Phe Cys Ala Arg Ala
    290                 295
```

```
<210> SEQ ID NO 18
<211> LENGTH: 18
<212> TYPE: PRT
<213> ORGANISM: Chlamydia trachomatis

<400> SEQUENCE: 18

Arg Ala Ala Ala Ala Ala Val Cys Ser Phe Ile Gly Gly Ile Thr
 1               5                  10                  15

Tyr Leu

<210> SEQ ID NO 19
<211> LENGTH: 18
<212> TYPE: PRT
<213> ORGANISM: Chlamydia trachomatis

<400> SEQUENCE: 19

Cys Ser Phe Ile Gly Gly Ile Thr Tyr Leu Ala Thr Phe Gly Ala Ile
 1               5                  10                  15

Arg Pro

<210> SEQ ID NO 20
<211> LENGTH: 216
<212> TYPE: PRT
<213> ORGANISM: Chlamydia trachomatis

<400> SEQUENCE: 20

Met Arg Gly Ser Gln Gln Ile Phe Val Cys Leu Ile Ser Ala Glu Arg
 1               5                  10                  15

Leu Arg Leu Ser Val Ala Ser Ser Glu Glu Leu Pro Thr Ser Arg His
                20                  25                  30

Ser Glu Leu Ser Val Arg Phe Cys Leu Ser Thr Lys Cys Trp Gln Asn
            35                  40                  45

Arg Phe Phe Leu Pro Lys Leu Lys Gln Ile Trp Asp Leu Leu Leu Ala
        50                  55                  60

Ile Leu Trp Arg Leu Thr Met Gln Arg Leu Trp Trp Val Leu Asp Ser
65                  70                  75                  80

Leu Ser Val Arg Lys Glu Gln Ile Ala Lys Pro Ala Ala Leu Val Leu
                85                  90                  95

Arg Glu Lys Ser Arg Tyr Ser Lys Cys Arg Glu Arg Lys Met Leu Ala
            100                 105                 110

Arg Arg Lys Ser Leu Glu Arg Lys Pro Arg Arg Ser Arg Ala Ser Ser
        115                 120                 125

Met His Ser Ser Leu Cys Ser Arg Ser Phe Trp Asn Ala Leu Pro Thr
    130                 135                 140

Phe Ser Asn Trp Cys Arg Cys Leu Leu Gln Trp Val Phe Val Arg Leu
145                 150                 155                 160

Trp Leu Leu Asp Val Arg Ser Leu Leu Gln Leu Leu Asp Cys Ala Leu
                165                 170                 175

Ser Ala Pro Glu His Lys Gly Phe Phe Lys Phe Leu Lys Lys Lys Ala
            180                 185                 190

Val Ser Lys Lys Lys Gln Pro Phe Leu Ser Thr Lys Cys Leu Ala Phe
        195                 200                 205

Leu Ile Val Lys Ile Val Phe Leu
    210                 215

<210> SEQ ID NO 21
```

<211> LENGTH: 1256
<212> TYPE: DNA
<213> ORGANISM: Chlamydia trachomatis

<400> SEQUENCE: 21

```
ctcgtgccgg cacgagcaaa gaaatccctc aaaaaatggc cattattggc ggtggtgtga      60
tcggttgcga attcgcttcc ttattccata cgttaggctc cgaagtttct gtgatcgaag     120
caagctctca aatccttgct ttgaataatc cagatatttc aaaaaccatg ttcgataaat     180
tcacccgaca aggactccgt ttcgtactag aagcctctgt atcaaatatt gaggatatag     240
gagatcgcgt tcggttaact atcaatggga atgtcgaaga atacgattac gttctcgtat     300
ctataggacg ccgtttgaat acagaaaata ttggcttgga taaagctggt gttatttgtg     360
atgaacgcgg agtcatccct accgatgcca caatgcgcac aaacgtacct aacatttatg     420
ctattggaga tatcacagga aaatggcaac ttgcccatgt agcttctcat caaggaatca     480
ttgcagcacg gaatataggt ggccataaag aggaaatcga ttactctgct gtcccttctg     540
tgatctttac cttccctgaa gtcgcttcag taggcctctc cccaacagca gctcaacaac     600
atctccttct tcgcttactt tttctgaaaa atttgataca gaagaagaat tcctcgcaca     660
cttgcgagga ggagggcgtc tggaagacca gttgaattta gctaagtttt ctgagcgttt     720
tgattctttg cgagaattat ccgctaagct tggttacgat agcgatggag agactgggga     780
tttcttcaac gaggagtacg acgacgaaga agaggaaatc aaaccgaaga aaactacgaa     840
acgtggacgt aagaagagcc gttcataagc cttgctttta aggtttggta gttttacttc     900
tctaaaatcc aaatggttgc tgtgccaaaa agtagtttgc gtttccggat agggcgtaaa     960
tgcgctgcat gaaagattgc ttcgagagcg gcatcgcgtg ggagatcccg gatactttct    1020
ttcagatacg aataagcata gctgttccca gaataaaaac ggccgacgct aggaacaaca    1080
agatttagat agagcttgtg tagcaggtaa actgggttat atgttgctgg gcgtgttagt    1140
tctagaatac ccaagtgtcc tccaggttgt aatactcgat acacttccct aagagcctct    1200
aatggatagg ataagttccg taatccatag gccatagaag ctaaacgaaa cgtatt       1256
```

<210> SEQ ID NO 22
<211> LENGTH: 601
<212> TYPE: DNA
<213> ORGANISM: Chlamydia trachomatis

<400> SEQUENCE: 22

```
ctcgtgccgg cacgagcaaa gaaatccctc aaaaaatggc cattattggc ggtggtgtga      60
tcggttgcga attcgcttcc ttattccata cgttaggctc cgaagtttct gtgatcgaag     120
caagctctca aatccttgct ttgaataatc cagatatttc aaaaaccatg ttcgataaat     180
tcacccgaca aggactccgt ttcgtactag aagcctctgt atcaaatatt gaggatatag     240
gagatcgcgt tcggttaact atcaatggga atgtcgaaga atacgattac gttctcgtat     300
ctataggacg ccgtttgaat acagaaaata ttggcttgga taaagctggt gttatttgtg     360
atgaacgcgg agtcatccct accgatgcca caatgcgcac aaacgtacct aacatttatg     420
ctattggaga tatcacagga aaatggcaac ttgcccatgt agcttctcat caaggaatca     480
ttgcagcacg gaatataggt ggccataaag aggaaatcga ttactctgct gtcccttctg     540
tgatctttac cttccctgaa gtcgcttcag taggcctctc cccaacagca gctcaacaac     600
a                                                                     601
```

<210> SEQ ID NO 23
<211> LENGTH: 270
<212> TYPE: DNA
<213> ORGANISM: Chlamydia trachomatis

<400> SEQUENCE: 23

```
acatctcctt cttcgcttac tttttctgaa aaatttgata cagaagaaga attcctcgca    60
cacttgcgag gaggagggcg tctggaagac cagttgaatt tagctaagtt ttctgagcgt   120
tttgattctt tgcgagaatt atccgctaag cttggttacg atagcgatgg agagactggg   180
gatttcttca acgaggagta cgacgacgaa gaagaggaaa tcaaaccgaa gaaaactacg   240
aaacgtggac gtaagaagag ccgttcataa                                    270
```

<210> SEQ ID NO 24
<211> LENGTH: 363
<212> TYPE: DNA
<213> ORGANISM: Chlamydia trachomatis

<400> SEQUENCE: 24

```
ttacttctct aaaatccaaa tggttgctgt gccaaaaagt agtttgcgtt tccggatagg    60
gcgtaaatgc gctgcatgaa agattgcttc gagagcggca tcgcgtggga gatcccggat   120
actttctttc agatacgaat aagcatagct gttcccagaa taaaaacggc cgacgctagg   180
aacaacaaga tttagataga gcttgtgtag caggtaaact gggttatatg ttgctgggcg   240
tgttagttct agaataccca agtgtcctcc aggttgtaat actcgataca cttccctaag   300
agcctctaat ggataggata agttccgtaa tccataggcc atagaagcta aacgaaacgt   360
att                                                                 363
```

<210> SEQ ID NO 25
<211> LENGTH: 696
<212> TYPE: DNA
<213> ORGANISM: Chlamydia trachomatis

<400> SEQUENCE: 25

```
gctcgtgccg gcacgagcaa agaaatccct caaaaaatgg ccattattgg cggtggtgtg    60
atcggttgcg aattcgcttc cttattccat acgttaggct ccgaagtttc tgtgatcgaa   120
gcaagctctc aaatccttgc tttgaataat ccagatattt caaaaaccat gttcgataaa   180
ttcacccgac aaggactccg tttcgtacta gaagcctctg tatcaaatat tgaggatata   240
ggagatcgcg ttcggttaac tatcaatggg aatgtcgaag aatacgatta cgttctcgta   300
tctataggac gccgtttgaa tacagaaaat attggcttgg ataaagctgg tgttatttgt   360
gatgaacgcg gagtcatccc taccgatgcc acaatgcgca caaacgtacc taacatttat   420
gctattggag atatcacagg aaaatggcaa cttgcccatg tagcttctca tcaaggaatc   480
attgcagcac ggaatatagg tggccataaa gaggaaatcg attactctgc tgtcccttct   540
gtgatcttta ccttccctga agtcgcttca gtaggcctct ccccaacagc agctcaacaa   600
catctccttc ttcgcttact tttctgaaa aatttgatac agaagaagaa ttcctcgcac   660
acttgcgagg aggagggcgt ctggaagacc agttga                             696
```

<210> SEQ ID NO 26
<211> LENGTH: 231
<212> TYPE: PRT
<213> ORGANISM: Chlamydia trachomatis

<400> SEQUENCE: 26

-continued

```
Ala Arg Ala Gly Thr Ser Lys Glu Ile Pro Gln Lys Met Ala Ile Ile
  1               5                  10                  15

Gly Gly Gly Val Ile Gly Cys Glu Phe Ala Ser Leu Phe His Thr Leu
             20                  25                  30

Gly Ser Glu Val Ser Val Ile Glu Ala Ser Ser Gln Ile Leu Ala Leu
         35                  40                  45

Asn Asn Pro Asp Ile Ser Lys Thr Met Phe Asp Lys Phe Thr Arg Gln
 50                  55                  60

Gly Leu Arg Phe Val Leu Glu Ala Ser Val Ser Asn Ile Glu Asp Ile
 65                  70                  75                  80

Gly Asp Arg Val Arg Leu Thr Ile Asn Gly Asn Val Glu Glu Tyr Asp
                 85                  90                  95

Tyr Val Leu Val Ser Ile Gly Arg Arg Leu Asn Thr Glu Asn Ile Gly
            100                 105                 110

Leu Asp Lys Ala Gly Val Ile Cys Asp Glu Arg Gly Val Ile Pro Thr
        115                 120                 125

Asp Ala Thr Met Arg Thr Asn Val Pro Asn Ile Tyr Ala Ile Gly Asp
130                 135                 140

Ile Thr Gly Lys Trp Gln Leu Ala His Val Ala Ser His Gln Gly Ile
145                 150                 155                 160

Ile Ala Ala Arg Asn Ile Gly Gly His Lys Glu Glu Ile Asp Tyr Ser
                165                 170                 175

Ala Val Pro Ser Val Ile Phe Thr Phe Pro Glu Val Ala Ser Val Gly
            180                 185                 190

Leu Ser Pro Thr Ala Ala Gln Gln His Leu Leu Arg Leu Leu Phe
        195                 200                 205

Leu Lys Asn Leu Ile Gln Lys Lys Asn Ser Ser His Thr Cys Glu Glu
    210                 215                 220

Glu Gly Val Trp Lys Thr Ser
225                 230
```

<210> SEQ ID NO 27
<211> LENGTH: 264
<212> TYPE: DNA
<213> ORGANISM: Chlamydia pneumoniae

<400> SEQUENCE: 27

```
atgagtcaaa aaataaaaa ctctgctttt atgcatcccg tgaatatttc cacagattta      60
gcagttatag ttggcaaggg acctatgccc agaaccgaaa ttgtaaagaa agtttgggaa    120
tacattaaaa aacacaactg tcaggatcaa aaaataaac gtaatatcct tcccgatgcg    180
aatcttgcca aagtctttgg ctctagtgat cctatcgaca tgttccaaat gaccaaagcc    240
ctttccaaac atattgtaaa ataa                                           264
```

<210> SEQ ID NO 28
<211> LENGTH: 87
<212> TYPE: PRT
<213> ORGANISM: Chlamydia pneumoniae

<400> SEQUENCE: 28

```
Met Ser Gln Lys Asn Lys Asn Ser Ala Phe Met His Pro Val Asn Ile
  1               5                  10                  15

Ser Thr Asp Leu Ala Val Ile Val Gly Lys Gly Pro Met Pro Arg Thr
             20                  25                  30

Glu Ile Val Lys Lys Val Trp Glu Tyr Ile Lys Lys His Asn Cys Gln
         35                  40                  45
```

Asp Gln Lys Asn Lys Arg Asn Ile Leu Pro Asp Ala Asn Leu Ala Lys
        50                  55                  60

Val Phe Gly Ser Ser Asp Pro Ile Asp Met Phe Gln Met Thr Lys Ala
 65                  70                  75                  80

Leu Ser Lys His Ile Val Lys
                85

<210> SEQ ID NO 29
<211> LENGTH: 369
<212> TYPE: DNA
<213> ORGANISM: Chlamydia pneumoniae

<400> SEQUENCE: 29
atgccacgca tcattggaat tgatattcct gcaaagaaaa agttaaaaat aagtctgaca      60
tatatttatg gaataggatc agctcgttct gatgaaatca ttaaaaagtt gaagttagat    120
cctgaggcaa gagcctctga attaactgaa gaagaagtag gacgactgaa ctctctgcta    180
caatcagaat ataccgtaga agggatttg cgacgtcgtg ttcaatcgga tatcaaaaga     240
ttgatcgcca tccattctta tcgaggtcag agacatagac tttctttacc agtaagagga    300
caacgtacaa aaactaattc tcgtactcga aaggtaaaa gaaaaacagt cgcaggtaag     360
aagaaataa                                                            369

<210> SEQ ID NO 30
<211> LENGTH: 122
<212> TYPE: PRT
<213> ORGANISM: Chlamydia pneumoniae

<400> SEQUENCE: 30

Met Pro Arg Ile Ile Gly Ile Asp Ile Pro Ala Lys Lys Lys Leu Lys
  1               5                  10                  15

Ile Ser Leu Thr Tyr Ile Tyr Gly Ile Gly Ser Ala Arg Ser Asp Glu
                 20                  25                  30

Ile Ile Lys Lys Leu Lys Leu Asp Pro Glu Ala Arg Ala Ser Glu Leu
             35                  40                  45

Thr Glu Glu Val Gly Arg Leu Asn Ser Leu Leu Gln Ser Glu Tyr
     50                  55                  60

Thr Val Glu Gly Asp Leu Arg Arg Val Gln Ser Asp Ile Lys Arg
 65                  70                  75                  80

Leu Ile Ala Ile His Ser Tyr Arg Gly Gln Arg His Arg Leu Ser Leu
                 85                  90                  95

Pro Val Arg Gly Gln Arg Thr Lys Thr Asn Ser Arg Thr Arg Lys Gly
                100                 105                 110

Lys Arg Lys Thr Val Ala Gly Lys Lys Lys
            115                 120

<210> SEQ ID NO 31
<211> LENGTH: 10
<212> TYPE: PRT
<213> ORGANISM: Artificial Sequence
<220> FEATURE:
<223> OTHER INFORMATION: Made in the lab

<400> SEQUENCE: 31

Cys Ser Phe Ile Gly Gly Ile Thr Tyr Leu
  1               5                  10

<210> SEQ ID NO 32
<211> LENGTH: 53
<212> TYPE: PRT
<213> ORGANISM: Chlamydia trachomatis

<400> SEQUENCE: 32

Leu Cys Val Ser His Lys Arg Arg Ala Ala Ala Val Cys Ser Phe
1               5                   10                  15

Ile Gly Gly Ile Thr Tyr Leu Ala Thr Phe Gly Ala Ile Arg Pro Ile
            20                  25                  30

Leu Phe Val Asn Lys Met Leu Ala Gln Pro Phe Leu Ser Ser Gln Thr
        35                  40                  45

Lys Ala Asn Met Gly
    50

<210> SEQ ID NO 33
<211> LENGTH: 161
<212> TYPE: DNA
<213> ORGANISM: Chlamydia trachomatis

<400> SEQUENCE: 33
atctttgtgt gtctcataag cgcagagcgg ctgcggctgt ctgtagcatc atcggaggaa      60
ttacctacct cgcgacattc ggagctatcc gtccgattct gtttgtcaac aaaatgctgg    120
caaaaccgtt tctttcttcc caaactaaag caaatatggg a                         161

<210> SEQ ID NO 34
<211> LENGTH: 53
<212> TYPE: PRT
<213> ORGANISM: Chlamydia trachomatis

<400> SEQUENCE: 34

Leu Cys Val Ser His Lys Arg Arg Ala Ala Ala Val Cys Ser Ile
1               5                   10                  15

Ile Gly Gly Ile Thr Tyr Leu Ala Thr Phe Gly Ala Ile Arg Pro Ile
            20                  25                  30

Leu Phe Val Asn Lys Met Leu Ala Lys Pro Phe Leu Ser Ser Gln Thr
        35                  40                  45

Lys Ala Asn Met Gly
    50

<210> SEQ ID NO 35
<211> LENGTH: 55
<212> TYPE: DNA
<213> ORGANISM: Chlamydia pneumoniae

<400> SEQUENCE: 35
gatatacata tgcatcacca tcaccatcac atgagtcaaa aaaataaaa actct            55

<210> SEQ ID NO 36
<211> LENGTH: 33
<212> TYPE: DNA
<213> ORGANISM: Chlamydia pneumoniae

<400> SEQUENCE: 36
ctcgaggaat tcttatttta caatatgttt gga                                   33

<210> SEQ ID NO 37
<211> LENGTH: 53
<212> TYPE: DNA
<213> ORGANISM: Chlamydia pneumoniae -continued

<210> SEQ ID NO 37
<400> SEQUENCE: 37
gatatacata tgcatcacca tcaccatcac atgccacgca tcattggaat gat      53

<210> SEQ ID NO 38
<211> LENGTH: 30
<212> TYPE: DNA
<213> ORGANISM: Chlamydia pneumoniae

<400> SEQUENCE: 38
ctcgaggaat tcttatttct tcttacctgc      30

<210> SEQ ID NO 39
<211> LENGTH: 16
<212> TYPE: PRT
<213> ORGANISM: Artificial Sequence
<220> FEATURE:
<223> OTHER INFORMATION: Made in the lab

<400> SEQUENCE: 39

Lys Arg Asn Ile Asn Pro Asp Asp Lys Leu Ala Lys Val Phe Gly Thr
1               5                   10                  15

<210> SEQ ID NO 40
<211> LENGTH: 16
<212> TYPE: PRT
<213> ORGANISM: Artificial Sequence
<220> FEATURE:
<223> OTHER INFORMATION: made in the lab

<400> SEQUENCE: 40

Lys Arg Asn Ile Leu Pro Asp Ala Asn Leu Ala Lys Val Phe Gly Ser
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: made in the lab

<400> SEQUENCE: 41

Lys Glu Tyr Ile Asn Gly Asp Lys Tyr Phe Gln Gln Ile Phe Asp
1               5                   10                  15

<210> SEQ ID NO 42
<211> LENGTH: 16
<212> TYPE: PRT
<213> ORGANISM: Artificial Sequence
<220> FEATURE:
<223> OTHER INFORMATION: made in the lab

<400> SEQUENCE: 42

Lys Lys Ile Ile Ile Pro Asp Ser Lys Leu Gln Gly Val Ile Gly Ala
1               5                   10                  15

<210> SEQ ID NO 43
<211> LENGTH: 15
<212> TYPE: PRT
<213> ORGANISM: Artificial Sequence
<220> FEATURE:
<223> OTHER INFORMATION: made in the lab

<400> SEQUENCE: 43

Lys Lys Leu Leu Val Pro Asp Asn Asn Leu Ala Thr Ile Ile Gly
1               5                   10                  15

<210> SEQ ID NO 44
<211> LENGTH: 509
<212> TYPE: DNA
<213> ORGANISM: Chlamydia

<400> SEQUENCE: 44

| | | | | | |
|---|---|---|---|---|---|
| ggagctcgaa | ttcggcacga | gagtgcctat | tgttttgcag | gctttgtctg | atgatagcga | 60 |
| taccgtacgt | gagattgctg | tacaagtagc | tgttatgtat | ggttctagtt | gcttactgcg | 120 |
| cgccgtgggc | gatttagcga | aaaatgattc | ttctattcaa | gtacgcatca | ctgcttatcg | 180 |
| tgctgcagcc | gtgttggaga | tacaagatct | tgtgcctcat | ttacgagttg | tagtccaaaa | 240 |
| tacacaatta | gatggaacgg | aaagaagaga | agcttggaga | tctttatgtg | ttcttactcg | 300 |
| gcctcatagt | ggtgtattaa | ctggcataga | tcaagcttta | atgacctgtg | agatgttaaa | 360 |
| ggaatatcct | gaaaagtgta | cggaagaaca | gattcgtaca | ttattggctg | cagatcatcc | 420 |
| agaagtgcag | gtagctactt | tacagatcat | tctgagagga | ggtagagtat | tccggtcatc | 480 |
| ttctataatg | gaatcggttc | tcgtgccgg | | | | 509 |

<210> SEQ ID NO 45
<211> LENGTH: 481
<212> TYPE: DNA
<213> ORGANISM: Chlamydia
<220> FEATURE:
<221> NAME/KEY: unsure
<222> LOCATION: (23)
<223> OTHER INFORMATION: n=A,T,C or G

<400> SEQUENCE: 45

| | | | | | |
|---|---|---|---|---|---|
| gatccgaatt | cggcacgagg | cantatttac | tcccaacatt | acggttccaa | ataagcgata | 60 |
| aggtcttcta | ataaggaagt | taatgtaaga | ggcttttttta | ttgcttttcg | taaggtagta | 120 |
| ttgcaaccgc | acgcgattga | atgatacgca | agccatttcc | atcatggaaa | agaaccttg | 180 |
| gacaaaaata | caaggaggt | tcactcctaa | ccagaaaaag | ggagagttag | tttccatggg | 240 |
| ttttccttat | atacacccgt | tcacacaat | taggagccgc | gtctagtatt | tggaatacaa | 300 |
| attgtcccca | agcgaatttt | gttcctgttt | cagggatttc | tcctaattgt | tctgtcagcc | 360 |
| atccgcctat | ggtaacgcaa | ttagctgtag | taggaagatc | aactccaaac | aggtcataga | 420 |
| aatcagaaag | ctcataggtg | cctgcagcaa | taacaacatt | cttgtctgag | tgagcgaatt | 480 |
| g | | | | | | 481 |

<210> SEQ ID NO 46
<211> LENGTH: 427
<212> TYPE: DNA
<213> ORGANISM: Chlamydia
<220> FEATURE:
<221> NAME/KEY: unsure
<222> LOCATION: (20)
<223> OTHER INFORMATION: n=A,T,C or G

<400> SEQUENCE: 46

| | | | | | |
|---|---|---|---|---|---|
| gatccgaatt | cggcacgagn | tttttcctgt | tttttcttag | ttttttagtgt | tcccggagca | 60 |
| ataacacaga | tcaaagaacg | gccattcagt | ttaggctctg | actcaacaaa | acctatgtcc | 120 |
| tctaagcct | gacacattct | tgaacaacc | ttatgcccgt | gttcgggata | agccaactct | 180 |
| cgcccccgaa | acatacaaga | aacctttact | ttatttcctt | tctcaataaa | ggctctagct | 240 |
| tgctttgctt | tcgtaagaaa | gtcgttatca | tcgatattag | gcttaagctt | aacctctttg | 300 |
| atacgcactt | ggtgctgtgc | tttcttacta | tcttttttctt | ttttagttat | gtcgtaacga | 360 |

```
tacttcccgt agtccatgat tttgcacaca ggaggctctg agtttgaagc aacctcgtgc    420
cgaattc                                                              427
```

<210> SEQ ID NO 47
<211> LENGTH: 600
<212> TYPE: DNA
<213> ORGANISM: Chlamydia
<220> FEATURE:
<221> NAME/KEY: unsure
<222> LOCATION: (522)
<223> OTHER INFORMATION: n=A,T,C or G

<400> SEQUENCE: 47

```
gatccgaatt cggcacgaga tgcttctatt acaattggtt tggatgcgga aaaagcttac     60
cagcttattc tagaaaagtt gggagatcaa attcttggtg gaattgctga tactattgtt    120
gatagtacag tccaagatat tttagacaaa atcacaacag acccttctct aggtttgttg    180 aaagcttta acaactttcc aatcactaat aaaattcaat gcaacgggtt attcactccc     240
aggaacattg aaactttatt aggaggaact gaaataggaa aattcacagt cacacccaaa    300
agctctggga gcatgttctt agtctcagca gatattattg catcaagaat ggaaggcggc    360
gttgttctag ctttggtacg agaaggtgat tctaagccct acgcgattag ttatggatac    420
tcatcaggcg ttcctaattt atgtagtcta agaaccagaa ttattaatac aggattgact    480
ccgacaacgt attcattacg tgtaggcggt ttagaaagcg gngtggtatg ggttaatgcc    540
ctttctaatg gcaatgatat tttaggaata acaaatcttc taatgtatct tttttggagg    600
```

<210> SEQ ID NO 48
<211> LENGTH: 600
<212> TYPE: DNA
<213> ORGANISM: Chlamydia

<400> SEQUENCE: 48

```
ggagctcgaa ttcggcacga gctctatgaa tatccaattc tctaaactgt tcggataaaa     60
atgatgcagg aattaggtcc acactatctt ttttttgttc gcaaatgatt gattttaaat    120
cgtttgatgt gtatactatg tcgtgtaagc cttttttggtt acttctgaca ctagccccca    180
atccagaaga taaattggat tgcgggtcta ggtcagcaag taacactttt ttccctaaaa    240
attgggccaa gttgcatccc acgtttagag aaagtgttgt ttttccagtt cctcccttaa    300
aagagcaaaa aactaaggtg tgcaaatcaa ctccaacgtt agagtaagtt atctattcag    360
ccttggaaaa catgtctttt ctagacaaga taagcataat caaagccttt tttagctta    420 aactgttatc ctctaatttt tcaagaacag gagagtctgg gaataatcct aaagagtttt    480
ctatttgttg aagcagtcct agaattagtg agacactttt atggtagagt tctaagggag    540
aatttaagaa agttactttt tccttgttta ctcgtatttt taggtctaat tcggggaaat    600
```

<210> SEQ ID NO 49
<211> LENGTH: 600
<212> TYPE: DNA
<213> ORGANISM: Chlamydia

<400> SEQUENCE: 49

```
gatccgaatt cggcacgaga tgcttctatt acaattggtt tggatgcgga aaaagcttac     60
cagcttattc tagaaaagtt gggagatcaa attcttggtg gaattgctga tactattgtt    120
gatagtacag tccaagatat tttagacaaa atcacaacag acccttctct aggtttgttg    180
```

-continued

```
aaagctttta caactttcc aatcactaat aaaattcaat gcaacgggtt attcactccc    240
aggaacattg aaactttatt aggaggaact gaaataggaa aattcacagt cacacccaaa    300
agctctggga gcatgttctt agtctcagca gatattattg catcaagaat ggaaggcggc    360
gttgttctag ctttggtacg agaaggtgat tctaagccct acgcgattag ttatggatac    420
tcatcaggcg ttcctaattt atgtagtcta agaaccagaa ttattaatac aggattgact    480
ccgacaacgt attcattacg tgtaggcggt ttagaaagcg gtgtggtatg ggttaatgcc    540
ctttctaatg gcaatgatat tttaggaata acaaatactt ctaatgtatc ttttttggag    600
```

<210> SEQ ID NO 50
<211> LENGTH: 406
<212> TYPE: DNA
<213> ORGANISM: Chlamydia

<400> SEQUENCE: 50

```
gatccgaatt cggcacgagt tcttagcttg cttaattacg taattaacca aactaaaggg     60
gctatcaaat agcttattca gtctttcatt agttaaacga tcttttctag ccatgactca    120
tcctatgttc ttcagctata aaaatacttc ttaaaacttg atatgctgta atcaaatcat    180
cattaaccac aacataatca aattcgctag cggcagcaat ttcgacagcg ctatgctcta    240
atctttcttt cttctggaaa tctttctctg aatcccgagc attcaaacgg cgctcaagtt    300
cttcttgaga gggagcttga ataaaaatgt gactgccggc atttgcttct tcagagccaa    360
agctccttgt acatcaatca cggctatgca gtctcgtgcc gaattc                   406
```

<210> SEQ ID NO 51
<211> LENGTH: 602
<212> TYPE: DNA
<213> ORGANISM: Chlamydia

<400> SEQUENCE: 51

```
gatccgaatt cggcacgaga tattttagac aaaatcacaa cagacccttc tctaggtttg     60
ttgaaagctt ttaacaactt tccaatcact aataaaattc aatgcaacgg ttattcact    120 cccaggaaca ttgaaacttt attaggagga actgaaatag gaaaattcac agtcacaccc    180
aaaagctctg ggagcatgtt cttagtctca gcagatatta ttgcatcaag aatggaaggc    240
ggcgttgttc tagctttggt acgagaaggt gattctaagc cctacgcgat tagttatgga    300
tactcatcag gcgttcctaa tttatgtagt ctaagaacca gaattattaa tacaggattg    360
actccgacaa cgtattcatt acgtgtaggc ggtttagaaa gcggtgtggt atgggttaat    420 gcccttcta tggcaatga tttttagga ataacaaata cttctaatgt atctttttg    480 gaggtaatac ctcaaacaaa cgcttaaaca attttttattg gattttttctt ataggtttta    540 tatttagaga aaaagttcg aattacgggg tttgttatgc aaaataaact cgtgccgaat    600
tc                                                                   602
```

<210> SEQ ID NO 52
<211> LENGTH: 145
<212> TYPE: DNA
<213> ORGANISM: Chlamydia

<400> SEQUENCE: 52

```
gatccgaatt cggcacgagc tcgtgccgat gtgttcaaca gcatccatag gatgggcagt     60
caaatatact ccaagtaatt cttttctct tttcaacaac tccttaggag agcgttggat    120
aacattttca gctcgtgccg aattc                                          145
```

<210> SEQ ID NO 53
<211> LENGTH: 450
<212> TYPE: DNA
<213> ORGANISM: Chlamydia

<400> SEQUENCE: 53

| | | | | | |
|---|---|---|---|---|---|
| gatccgaatt | cggcacgagg | taatcggcac | cgcactgctg | acactcatct | cctcgagctc | 60 |
| gatcaaaccc | acacttggga | caagtaccta | caacataacg | gtccgctaaa | aacttccctt | 120 |
| cttcctcaga | atacagctgt | tcggtcacct | gattctctac | cagtccgcgt | tcctgcaagt | 180 |
| ttcgatagaa | atcttgcaca | atagcaggat | gataagcgtt | cgtagttctg | gaaagaaat | 240 |
| ctacagaaat | tcccaatttc | ttgaaggtat | ctttatgaag | cttatgatac | atgtcgacat | 300 |
| attcttgata | ccccatgcct | gccaactctg | cattaagggt | aattgcgatt | ccgtattcat | 360 |
| cagaaccaca | aatatacaaa | acctctttgc | cttgtagtct | ctgaaaacgc | gcataaacat | 420 |
| ctgcaggcaa | ataagcctcg | tgccgaattc | | | | 450 |

<210> SEQ ID NO 54
<211> LENGTH: 716
<212> TYPE: DNA
<213> ORGANISM: Chlamydia

<400> SEQUENCE: 54

| | | | | | |
|---|---|---|---|---|---|
| gatcgaaatt | cggcacgagc | ggcacgagtt | ttctgatagc | gatttacaat | cctttattca | 60 |
| acttttgcct | agagaggcac | actatactaa | gaagtttctt | gggtgtgtgg | cacagtcctg | 120 |
| tcgtcagggg | attctgctag | aggggtaggg | gaaaaaaccc | ttattactat | gaccatgcgc | 180 |
| atgtggaatt | acattccata | gactttcgca | tcattcccaa | catttacaca | gctctacacc | 240 |
| tcttaagaag | aggtgacgtg | gattgggtgg | ggcagccttg | gcaccaaggg | attccttttg | 300 |
| agcttcggac | tacctctgct | ctctacaccc | attaccctgt | agatggcaca | ttctggctta | 360 |
| ttcttaatcc | caaagatcct | gtactttcct | ctctatctaa | tcgtcagcga | ttgattgctg | 420 |
| ccatccaaaa | ggaaaaactg | gtgaagcaag | ctttaggaac | acaatatcga | gtagctgaaa | 480 |
| gctctccatc | tccagaggga | atcatagctc | atcaagaagc | ttctactcct | tttcctggga | 540 |
| aaattacttt | gatatatccc | aataatatta | cgcgctgtca | gcgtttggcc | gaggtatcca | 600 |
| aaaaatgatc | gacaaggagc | acgctaaatt | tgtacatacc | ccaaaatcaa | tcagccatct | 660 |
| aggcaaatgg | aatatcaaag | taaacagtat | acaactgggg | atctcgtgcc | gaattc | 716 |

<210> SEQ ID NO 55
<211> LENGTH: 463
<212> TYPE: DNA
<213> ORGANISM: Chlamydia trachomatis

<400> SEQUENCE: 55

| | | | | | |
|---|---|---|---|---|---|
| tctcaaatcc | ttgctttgaa | taatccagat | atttcaaaaa | ccatgttcga | taaattcacc | 60 |
| cgacaaggac | tccgtttcgt | actagaagcc | tctgtatcaa | atattgagga | tataggagat | 120 |
| cgcgttcggt | taactatcaa | tgggaatgtc | gaagaatacg | attacgttct | cgtatctata | 180 |
| ggacgccgtt | tgaatacaga | aaatattggc | ttggataaag | ctggtgttat | ttgtgatgaa | 240 |
| cgcggagtca | tccctaccga | tgccacaatg | cgcacaaacg | tacctaacat | ttatgctatt | 300 |
| ggagatatca | caggaaaatg | gcaacttgcc | catgtagctt | ctcatcaagg | aatcattgca | 360 |
| gcacggaata | taggtggcca | taaagaggaa | atcgattact | ctgctgtccc | ttctgtgatc | 420 |

-continued tttaccttcc ctgaagtcgc ttcagtaggc ctctccccaa cag                             463

<210> SEQ ID NO 56
<211> LENGTH: 829
<212> TYPE: DNA
<213> ORGANISM: Chlamydia trachomatis

<400> SEQUENCE: 56
gtactatggg atcattagtt ggaagacagg ctccggattt ttctggtaaa gccgttgttt            60
gtggagaaga gaaagaaatc tctctagcag actttcgtgg taagtatgta gtgctcttct           120
tttatcctaa agattttacc tatgtttgtc ctacagaatt acatgctttt caagatagat           180
tggtagattt tgaagagcat ggtgcagtcg tccttggttg ctccgttgac gacattgaga           240
cacattctcg ttggctcact gtagcgagag atgcaggagg atagaggga acagaatatc            300
ctctgttagc agaccctctc tttaaaatat cagaagcttt tggtgttttg aatcctgaag           360
gatcgctcgc tttaagagct actttcctta tcgataaaca tggggttatt cgtcatgcgg           420
ttatcaatga tcttcccttta gggcgttcca ttgacgagga attgcgtatt ttagattcat          480
tgatcttctt tgagaaccac ggaatggttt gtccagctaa ctggcgttct ggagagcgtg           540
gaatggtgcc ttctgaagag ggattaaaag aatacttcca gacgatggat taagcatctt           600
tgaaagtaag aaagtcgtac agatcttgat ctgaaaagag aagaaggctt tttaattttc           660
tgcagagagc cagcgaggct tcaataatgt tgaagtctcc gacaccaggc aatgctaagg           720
cgacgatatt agttagtgaa gtctgagtat taaggaaatg aaggccaaag aaatagctat           780
caataaagaa gccttcttcc ttgactctaa agaatagtat gtcgtatcc                       829

<210> SEQ ID NO 57
<211> LENGTH: 1537
<212> TYPE: DNA
<213> ORGANISM: Chlamydia trachomatis

<400> SEQUENCE: 57
acatcaagaa atagcggact cgcctttagt gaaaaagct gaggagcaga ttaatcaagc             60
acaacaagat attcaaacga tcacacctag tggtttggat attcctatcg ttggtccgag           120
tgggtcagct gcttccgcag gaagtgcggc aggagcgttg aaatcctcta acaattcagg           180
aagaatttcc ttgttgcttg atgatgtaga caatgaaatg gcagcgattg caatgcaagg           240
ttttcgatct atgatcgaac aatttaatgt aaacaatcct gcaacagcta agagctaca            300
agctatggag gctcagctga ctgcgatgtc agatcaactg gttggtgcgg atggcgagct           360
cccagccgaa atacaagcaa tcaaagatgc tcttgcgcaa gctttgaaac aaccatcagc           420
agatggttta gctacagcta tgggacaagt ggcttttgca gctgccaagg ttggaggagg           480
ctccgcagga acagctggca ctgtccagat gaatgtaaaa cagctttaca agacagcgtt           540
ttcttcgact tcttccagct cttatgcagc agcactttcc gatggatatt ctgcttacaa           600
aacactgaac tctttatatt ccgaaagcag aagcggcgtg cagtcagcta ttagtcaaac           660
tgcaaatccc gcgctttcca gaagcgtttc tcgttctggc atagaaagtc aaggacgcag           720
tgcagatgct agccaaagag cagcagaaac tattgtcaga gatagccaaa cgttaggtga           780
tgtatatagc cgcttacagg ttctggattc tttgatgtct acgattgtga gcaatccgca           840
agcaaatcaa gaagagatta tgcagaagct cacggcatct attagcaaag ctccacaatt           900
tgggtatcct gctgttcaga attctgtgga tagcttgcag aagtttgctg cacaattgga           960
aagagagttt gttgatgggg aacgtagtct cgcagaatct caagagaatg cgtttagaaa          1020

```
acagcccgct tcattcaac aggtgttggt aaacattgct tctctattct ctggttatct    1080
ttcttaacgt gtgattgaag tttgtgaatt gagggggagc caaaaaagaa tttctttttt    1140
ggctcttttt tcttttcaaa ggaatctcgt gtctacagaa gtcttttcaa taataagttc    1200
ttagttccaa aagaagaaaa tatataaaag aaaaaactcc taattcattt aaaaagtgct    1260
cggcagactt cgtggaaaat gtctgtaaag ctggagggga atcagcagaa agatgcaaga    1320
tatccgagaa aaaaggctca ggctcgtgcc gaattcggca cgagactacg aaagaaaggt    1380
cttttctttc ggaatctgtc attggatctg cgtaagactt aaagttcggc aacacaggct    1440
ctgtcttctc tttaggtttc ttgcgcgaga aaaattttct caagtaacaa gaagatttct    1500
ttttacagcc ggcatccggc ttctcgcgaa gtataac                             1537
```

<210> SEQ ID NO 58
<211> LENGTH: 463
<212> TYPE: DNA
<213> ORGANISM: Chlamydia trachomatis

<400> SEQUENCE: 58

```
tctcaaatcc ttgctttgaa taatccagat atttcaaaaa ccatgttcga taaattcacc     60
cgacaaggac tccgtttcgt actagaagcc tctgtatcaa atattgagga tataggagat    120
cgcgttcggt taactatcaa tgggaatgtc gaagaatacg attacgttct cgtatctata    180
ggacgccgtt tgaatacaga aaatattggc ttggataaag ctggtgttat ttgtgatgaa    240
cgcggagtca tccctaccga tgccacaatg cgcacaaacg tacctaacat ttatgctatt    300
ggagatatca caggaaaatg gcaacttgcc catgtagctt ctcatcaagg aatcattgca    360
gcacggaata taggtggcca taagaggaa atcgattact ctgctgtccc ttctgtgatc    420
tttaccttcc ctgaagtcgc ttcagtaggc ctctccccaa cag                     463
```

<210> SEQ ID NO 59
<211> LENGTH: 552
<212> TYPE: DNA
<213> ORGANISM: Chlamydia trachomatis

<400> SEQUENCE: 59

```
acattcctcc tgctcctcgc ggccatccac aaattgaggt aaccttcgat attgatgcca     60
acggaatttt acacgtttct gctaaagatg ctgctagtgg acgcgaacaa aaaatccgta    120
ttgaagcaag ctctggatta aagaagatg aaattcaaca aatgatccgc gatgcagagc    180
ttcataaaga ggaagacaaa caacgaaaag aagcttctga tgtgaaaaat gaagccgatg    240
gaatgatctt tagagccgaa aaagctgtga agattacca cgacaaaatt cctgcagaac    300
ttgttaaaga aattgaagag catattgaga agtacgcca agcaatcaaa gaagatgctt    360
ccacaacagc tatcaaagca gcttctgatg agttgagtac tcgtatgcaa aaaatcggag    420
aagctatgca ggctcaatcc gcatccgcag cagcatcttc tgcagcgaat gctcaaggag    480
ggccaaacat taactccgaa gatctgaaaa acatagttt cagcacacga cctccagcag    540
gaggaagcgc ct                                                       552
```

<210> SEQ ID NO 60
<211> LENGTH: 1180
<212> TYPE: DNA
<213> ORGANISM: Chlamydia trachomatis

<400> SEQUENCE: 60

-continued

```
atcctagcgg taaaactgct tactggtcag ataaaatcca tacagaagca acacgtactt      60
cttttaggag aaaaaatcta taatgctaga aaaatcctga gtaaggatca cttctcctca     120 acaactttt catcttggat agagttagtt tttagaacta agtcttctgc ttacaatgct      180
cttgcatatt acgagctttt tataaacctc cccaaccaaa ctctacaaaa agagtttcaa     240
tcgatcccct ataaatccgc atatattttg gccgctagaa aaggcgattt aaaaaccaag     300
gtcgatgtga tagggaaagt atgtggaatc tcgtgccgaa ttcggcacga gcggcacgag     360
gatgtagagt aattagttaa agagctgcat aattatgaca aagcatggaa aacgcattcg     420
tggtatccaa gagacttacg atttagctaa gtcgtattct ttgggtgaag cgatagatat     480
tttaaaacag tgtcctactg tgcgtttcga tcaaacggtt gatgtgtctg ttaaattagg     540
gatcgatcca agaaagagtg atcagcaaat tcgtggttcg gtttctttac ctcacggtac     600
aggtaaagtt ttgcgaattt tagttttttgc tgctggagat aaggctgcag aggctattga     660
agcaggagcg gactttgttg gtagcgacga cttggtagaa aaaatcaaag gtggatgggt     720
tgacttcgat gttgcggttg ccactcccga tatgatgaga gaggtcggaa agctaggaaa     780
agttttaggt ccaagaaacc ttatgcctac gcctaaagcc ggaactgtaa caacagatgt     840
ggttaaaact attgcggaac tgcgaaaagg taaaattgaa tttaaagctg atcgagctgg     900
tgtatgcaac gtcggagttg cgaagctttc tttcgatagt gcgcaaatca agaaaatgt      960 tgaagcgttg tgtgcagcct tagttaaagc taagcccgca actgctaaag gacaatattt    1020
agttaatttc actatttcct cgaccatggg gccaggggtt accgtggata ctaggagtt     1080 gattgcgtta taattctaag tttaaagagg aaaaatgaaa gaagagaaaa agttgctgct    1140
tcgcgaggtt gaagaaaaga taaccgcttc tcggcacgag                          1180
```

<210> SEQ ID NO 61
<211> LENGTH: 1215
<212> TYPE: DNA
<213> ORGANISM: Chlamydia trachomatis

<400> SEQUENCE: 61

```
attacagcgt gtgcaggtaa cgacatcatt gcatgatgct tttgatggca ttgatgcggc      60
attccttata gggtcagttc ctagaggccc aggaatggag agaagagatc ttctaaagaa     120
aaatggggag attgttgcta cgcaaggaaa agctttgaac acaacagcca agcgggatgc     180 aaagatttt gttgttggga accctgtgaa taccaattgc tggatagcaa tgaatcatgc      240
tcccagatta ttgagaaaga actttcatgc gatgctacga ttggaccaga atcgtatgca     300
tagcatgtta tcgcatagag cagaagtacc tttatcggct gtatcacaag ttgtggtttg     360
gggaaatcac tccgccaaac aagtgcctga ttttacgcaa gctctgatta atgaccgtcc     420
tatcgcagag acgatagcgg atcgtgattg gttagagaat attatggtgc cttctgtaca     480
gagtcgtggt agtgcagtaa ttgaagcacg agggaagtct tcggcagctt ctgcagcacg     540
agctttagca gaggctgctc gatcaatata tcagccaaaa gaaggactcg tgccgaattc     600
ggcacgagta tcgaaattgc aggcatttct agtgaatggt cgtatgctta taaactacgt     660
ggtacagact tgagctctca aaagtttgct acagattctt acatcgcaga cccttattct     720
aagaatatct actcccctca actatttgga tcccctaaac aagaaaagga ttacgcattt     780
agttacctga aatatgagga ttttgactgg gaaggcgaca ctcctttgca ccttccaaaa     840
gaaaattact tcatttatga aatgcatgtt cggtcattca cccgagatcc gtcttcccag     900
gtttcccatc ctggaacttt ccttggtatc atcgaaaaaa tagccaccct caaacaacta     960
```

```
ggcgttcatg cagttgaact ccttcctatt ttcgaattcg atgaaaccgt ccatccattt   1020
aaaaatcagg acttccccca cctgtgtaac tattgggggt attcttcggt gaattttttc   1080
tgcccctctc gccgttatac ttatggggca gaccttgcgc tccggcccg  agagttcaag   1140 actcttgtca aagcgttaca ccgtgcggga atcgaagtca ttctcgatgt cgttttcaat   1200
catacaggct ttgaa                                                    1215

<210> SEQ ID NO 62
<211> LENGTH: 688
<212> TYPE: DNA
<213> ORGANISM: Chlamydia trachomatis

<400> SEQUENCE: 62
gtggatccaa aaagaatct aaaaagccat acaaagattg cgttacttct tgcgatgcct    60 ctaacactttt atcagcgtca tctttgagaa gcatctcaat gagcgctttt tcttctctag  120
catgccgcac atccgcttct tcatgttctg tgaaatatgc atagtcttca ggattggaaa   180
atccaaagta ctcagtcaat ccacgaattt tctctctagc gatacgtgga atttgactct   240
cataagaata caaagcagcc actcctgcag ctaaagaatc tcctgtacac caccgcatga   300
aagtagctac tttcgctttt gctgcttcac taggctcatg agcctctaac tcttctggag   360
taactcctag agcaaacaca aactgcttcc acaaatcaat atgattaggg taaccgttct   420
cttcatccat caagttatct aacaataact acgcgcctc taaatcatcg caacgactat    480
gaatcgcaga taaatattta ggaaaggctt tgatatgtaa ataatagtct ttggcacgag   540
cctgtaattg ctctttagta agctccccct tcgaccattt cacataaaac gtgtgttcta   600
gcatatgctt attttgaata attaaatcta actgatctaa aaaattcata aacacctcca   660
tcatttcttt tcttgactcc acgtaacc                                      688

<210> SEQ ID NO 63
<211> LENGTH: 269
<212> TYPE: DNA
<213> ORGANISM: Chlamydia trachomatis

<400> SEQUENCE: 63
atgttgaaat cacacaagct gttcctaaat atgctacggt aggatctccc tatcctgttg    60
aaattactgc tacaggtaaa agggattgtg ttgatgttat cattactcag caattaccat   120
gtgaagcaga gttcgtacgc agtgatccag cgacaactcc tactgctgat ggtaagctag   180
tttggaaaat tgaccgctta ggacaaggcg aaaagagtaa aattactgta tgggtaaaac   240
ctcttaaaga aggttgctgc tttacagct                                     269

<210> SEQ ID NO 64
<211> LENGTH: 1339
<212> TYPE: DNA
<213> ORGANISM: Chlamydia trachomatis

<400> SEQUENCE: 64
cttttattat ggcttctggg gatgatgtca acgatatcga cctgctatct cgaggagatt    60
ttaaaattgt tatacagacg gctccagagg agatgcatgg attagcggac tttttggctc   120
ccccggcgaa ggatcttggt attctctccg cctgggaagc tggtgagctg cgttacaaac   180
agctagttaa tccttaggaa acatttctgg acctatgccc atcacattgg ctccgtgatc   240
cacatagaga gtttctcccg taattgcgct agctagggga gagactaaga aggctgctgc   300
```

-continued

```
tgcgcctact tgctcagctt ccattggaga aggtagtgga gcccagtctt ggtagtaatc    360
caccattctc tcaataaatc caatagcttt tcctgcacgg ctagctaatg ccctgccga    420 gatagtattc actcggactc cccaacgtcg gccggcttcc caagccagta cttttgtatc    480
actttctaaa gcagcttttg ctgcgttcat tcctccgcca taccctggaa cagcacgcat    540
ggaagcaaga taagttagag agatggtgct agctcctgca ttcataattg ggccaaaatg    600
agagagaagg ctgataaagg agtagctgga tgtacttaag gcggcaagat agcctttacg    660
agaggtatca agtaatggtt tagcaatttc cggactgttt gctaaagagt gaacaagaat    720
atcaatgtgt ccaaaatctt ttttcacctg ttctacaact tcggatacag tgtacccaga    780
aagatctttg taacgtttat tttccaaaat ttcctgagga atatcttctg gggtgtcgaa    840
actggcatcc atgggataga ttttagcgaa agttagcaat tctccattgg agagttcacg    900
agatgcattg aattttccta actcccaaga ttgagagaaa attttataga taggaaccca    960
ggtccccaca agtatggttg cgcctgcttc tgctaacatt ttggcaatgc cccagccata   1020
cccgttatca tcgcctatgc cggctatgaa agcaattttt cctgttaaat caattttcaa   1080
catgagctaa ccccatttg tcttcttgag agaggagagt agcagattct ttattattga   1140
gaaacgggcc tcataataca taaggagtag attcactggc tggatccagg tttctagagt   1200
aaagagtttc cttgtcaaat tcttatatgg gtagagttaa tcaactgttt tcaagtgatt   1260
tatgtttatt ttaaaataat ttgttttaac aactgtttaa tagttttaat ttttaaagtg   1320
tgaaaaacag gttttatat                                                1339
```

<210> SEQ ID NO 65
<211> LENGTH: 195
<212> TYPE: PRT
<213> ORGANISM: Chlamydia trachomatis

<400> SEQUENCE: 65

```
Met Gly Ser Leu Val Gly Arg Gln Ala Pro Asp Phe Ser Gly Lys Ala
                 5                  10                  15
Val Val Cys Gly Glu Lys Glu Ile Ser Leu Ala Asp Phe Arg Gly
            20                  25                  30
Lys Tyr Val Val Leu Phe Phe Tyr Pro Lys Asp Phe Thr Tyr Val Cys
        35                  40                  45
Pro Thr Glu Leu His Ala Phe Gln Asp Arg Leu Val Asp Phe Glu Glu
    50                  55                  60
His Gly Ala Val Val Leu Gly Cys Ser Val Asp Asp Ile Glu Thr His
65                  70                  75                  80
Ser Arg Trp Leu Thr Val Ala Arg Asp Ala Gly Ile Glu Gly Thr
                85                  90                  95
Glu Tyr Pro Leu Leu Ala Asp Pro Ser Phe Lys Ile Ser Glu Ala Phe
            100                 105                 110
Gly Val Leu Asn Pro Glu Gly Ser Leu Ala Leu Arg Ala Thr Phe Leu
        115                 120                 125
Ile Asp Lys His Gly Val Ile Arg His Ala Val Ile Asn Asp Leu Pro
    130                 135                 140
Leu Gly Arg Ser Ile Asp Glu Glu Leu Arg Ile Leu Asp Ser Leu Ile
145                 150                 155                 160
Phe Phe Glu Asn His Gly Met Val Cys Pro Ala Asn Trp Arg Ser Gly
                165                 170                 175
Glu Arg Gly Met Val Pro Ser Glu Glu Gly Leu Lys Glu Tyr Phe Gln
            180                 185                 190
```

Thr Met Asp
      195

<210> SEQ ID NO 66
<211> LENGTH: 520
<212> TYPE: DNA
<213> ORGANISM: Chlamydia

<400> SEQUENCE: 66

| | | | | | |
|---|---|---|---|---|---|
| gatccgaatt | cggcacgagg | aggaatggaa | gggccctccg | attttaaatc | tgctaccatg | 60 |
| ccattcacta | gaaactccat | aacagcggtt | ttctctgatg | gcgagtaaga | agcaagcatt | 120 |
| tgatgtaaat | tagcgcaatt | agaggggat | gaggttactt | ggaaatataa | ggagcgaagc | 180 |
| gatgaaggag | atgtatttgc | tctggaagca | aaggtttctg | aagctaacag | aacattgcgt | 240 |
| cctccaacaa | tcgcctgagg | attctggctc | atcagttgat | gctttgcctg | aatgagagcg | 300 |
| gacttaagtt | tcccatcaga | gggagctatt | tgaattagat | aatcaagagc | tagatccttt | 360 |
| attgtgggat | cagaaaattt | acttgtgagc | gcatcgagaa | tttcgtcaga | agaagaatca | 420 |
| tcatcgaacg | aattttttcaa | tcctcgaaaa | tcttctccag | agacttcgga | aagatcttct | 480 |
| gtgaaacgat | cttcaagagg | agtatcgcct | ttttcctctg | | | 520 |

<210> SEQ ID NO 67
<211> LENGTH: 276
<212> TYPE: DNA
<213> ORGANISM: Chlamydia

<400> SEQUENCE: 67

| | | | | | |
|---|---|---|---|---|---|
| gatccgaatt | cggcacgagg | tattgaagga | gaaggatctg | actcgatcta | tgaaatcatg | 60 |
| atgcctatct | atgaagttat | gaatatggat | ctagaaacac | gaagatcttt | tgcggtacag | 120 |
| caagggcact | atcaggaccc | aagagcttca | gattatgacc | tcccacgtgc | tagcgactat | 180 |
| gatttgccta | gaagcccata | tcctactcca | cctttgcctt | ctagatatca | gctacagaat | 240 |
| atggatgtag | aagcagggtt | ccgtgaggca | gtttat | | | 276 |

<210> SEQ ID NO 68
<211> LENGTH: 248
<212> TYPE: DNA
<213> ORGANISM: Chlamydia

<400> SEQUENCE: 68

| | | | | | |
|---|---|---|---|---|---|
| gatccgaatt | cggcacgagg | tgttcaagaa | tatgtccttc | aagaatgggt | taaattgaaa | 60 |
| gatctaccgg | tagaagagtt | gctagaaaaa | cgatatcaga | aattccgaac | gataggtcta | 120 |
| tatgaaactt | cttctgaaag | cgattctgag | gcataagaag | catttagttt | tattcggttt | 180 |
| ttctcttttta | tccatattag | ggctaacgat | aacgtctcaa | gcagaaattt | tttctctagg | 240 |
| tcttattg | | | | | | 248 |

<210> SEQ ID NO 69
<211> LENGTH: 715
<212> TYPE: DNA
<213> ORGANISM: Chlamydia
<220> FEATURE:
<221> NAME/KEY: unsure
<222> LOCATION: (34)
<223> OTHER INFORMATION: n=A,T,C or G

<400> SEQUENCE: 69

| | | | | | |
|---|---|---|---|---|---|
| gatccgaatt | cggcacgaga | aggtagatcc | gatntcagca | aaagtgctcc | taaaggaaga | 60 |

```
ttccttcggt atcctgcagc aaataaggtg gcacactcca tctcggacag tttgagcttt    120
attttcatat agttttcgac ggaactcttt attaaactcc caaaaccgaa tgttagtcgt    180
gtgggtgatg cctatatggt aagggaggtt tttggcttcg agaatattgg tgatcatttt    240
ttgtacgaca aaattagcta atgcaggac ctctgggggg aagtatgcat ctgatgttcc     300
atcttttcgg atgctagcaa cagggacaaa ataatctcct atttggtagt gggatcttaa    360
gcctccgcac atgcccaaca tgatcgctgc tgtagcattg ggaaggaaag aacacagatc    420
tacggtaaga gctgctcctg gagagcctaa tttaaaatcg atgattgagg tgtgaatttg    480
aggcgcatgc gctgccgaaa acatggatcc tcgagaaaca gggacctgat agatttcagc    540
gaaaacatcc acgtaatac ccmaaattag taagaaggag atagggctgg aactcttgaa     600
tggtagagcc ggtatagcgc tctagcatgt cacaggcgat tgtttcttcg ctgattttt     660 tatgttgatg ggtcataaat cacagatatt ataatggtta gagaatcttt ttttc         715

<210> SEQ ID NO 70
<211> LENGTH: 323
<212> TYPE: DNA
<213> ORGANISM: Chlamydia

<400> SEQUENCE: 70
gatccgaatt cggcacgagc agaacgtaaa cagcacactt aaaccgtgta tgaggtttaa     60
cactgtttgg caagcaaaca accattcctc tttccacatc gttcttacca atacctctga    120
ggagcaatcc aacattctct cctgcacgac cttctgggag ttcttttctg aacatttcaa    180
ccccagtaac aatcgtttct ttagtatctc taagaccgac caactgaact ttatcggaaa    240
ctttaacaat tccacgctca atacgtccag ttactacagt tcctcgtccg gagatagaga    300
acacgtcctc aatgggcatt aag                                            323

<210> SEQ ID NO 71
<211> LENGTH: 715
<212> TYPE: DNA
<213> ORGANISM: Chlamydia

<400> SEQUENCE: 71
gatccgaatt cggcacgagg aaaaaaagat tctctaacca ttataatatc tgtgatttat     60
gacccatcaa cataaaaaaa tcagcgaaga aacaatcgcc tgtgacatgc tagagcggct    120
ataccggctc taccattcaa gagttccagc cctatctcct tcttactaat tttgggtatt    180
acgtggatgt tttcgctgaa atctatcagg tccctgtttc tcgaggatcc atgttttcgg    240
gcagcgcatg cgcctcaaat tcacacctca atcatcgatt ttaaattagg ctctccagga    300
gcagctctta ccgtagatct gtgttctttc cttcccaatg ctacagcagc gatcatgttg    360
ggcatgtgcg gaggcttaag atcccactac caaataggag attattttgt ccctgttgct    420
agcatccgaa aagatggaac atcagatgca tacttccccc cagaggtccc tgcattagct    480
aattttgtcg tacaaaaaat gatcaccaat attctcgaag ccaaaaacct cccttaccat    540
ataggcatca cccacacgac taacattcgg ttttgggagt ttaataaaga gttccgtcga    600
aaactatatg aaaataaagc tcaaactgtc gagatggagt gtgccacctt atttgctgca    660
ggataccgaa ggaatcttcc tttaggagca cttttgctga tatcggatct accttt        715

<210> SEQ ID NO 72
<211> LENGTH: 641
<212> TYPE: DNA
```

```
<213> ORGANISM: Chlamydia
<220> FEATURE:
<221> NAME/KEY: unsure
<222> LOCATION: (550)
<223> OTHER INFORMATION: n=A,T,C or G
<220> FEATURE:
<221> NAME/KEY: unsure
<222> LOCATION: (559)
<223> OTHER INFORMATION: n=A,T,C or G
<220> FEATURE:
<221> NAME/KEY: unsure
<222> LOCATION: (575)
<223> OTHER INFORMATION: n=A,T,C or G
<220> FEATURE:
<221> NAME/KEY: unsure
<222> LOCATION: (583)
<223> OTHER INFORMATION: n=A,T,C or G
<220> FEATURE:
<221> NAME/KEY: unsure
<222> LOCATION: (634)
<223> OTHER INFORMATION: n=A,T,C or G
<220> FEATURE:
<221> NAME/KEY: unsure
<222> LOCATION: (638)
<223> OTHER INFORMATION: n=A,T,C or G

<400> SEQUENCE: 72
gatccgaatt cggcacgaga tctcctcgag ctcgatcaaa cccacacttg ggacaagtac      60
ctacaacata acggtccgct aaaaacttcc cttcttcctc agaatacagc tgttcggtca     120
cctgattctc taccagtccg cgttcctgca gtttcgata gaaatcttgc acaatagcag     180
gatgataagc gttcgtagtt ctggaaaaga atctacaga aattcccaat ttcttgaagg     240
tatctttatg aagcttatga tacatgtcga catattcttg atacccatg cctgccaact     300 ctgcattaag ggtaattgcg attccgtatt catcagaacc acaaatatac aaaacctctt     360
tgccttgtag tctctgaaaa cgcgcataaa catctgcagg caaataagca ccggtaatat     420
gtccaaaatg caaggacca tttgcgtaag gcaacgcaga agtaataaga atacgggaag      480
attccactat ttcacgtcgc tccagttgta cagagaagga tcttttcttc tggatgttcc     540
gaaaccttgn tctcttcgnc tctctcctgt agcanacaaa tgnctctctc gacatctctt     600
tcagcgtatt cggactgatg ccctaaagat cccnggangt t                         641

<210> SEQ ID NO 73
<211> LENGTH: 584
<212> TYPE: DNA
<213> ORGANISM: Chlamydia
<220> FEATURE:
<221> NAME/KEY: unsure
<222> LOCATION: (460)
<223> OTHER INFORMATION: n=A,T,C or G
<220> FEATURE:
<221> NAME/KEY: unsure
<222> LOCATION: (523)
<223> OTHER INFORMATION: n=A,T,C or G
<220> FEATURE:
<221> NAME/KEY: unsure
<222> LOCATION: (541)
<223> OTHER INFORMATION: n=A,T,C or G
<220> FEATURE:
<221> NAME/KEY: unsure
<222> LOCATION: (546)
<223> OTHER INFORMATION: n=A,T,C or G

<400> SEQUENCE: 73
gaattcggca cgagacattt ctagaatgga accggcaaca acaaaaact ttgtatctga      60 agatgacttt aagcaatctt tagataggga agattttttg gaatgggtct ttttatttgg    120
gacttattac ggaacgagta aggcggagat ttctagagtt ctgcaaaagg gtaagcactg    180
```

```
catagccgtg attgatgtac aaggagcttt ggctctgaag aagcaaatgc cggcagtcac      240 tattttatt caagctccct ctcaagaaga acttgagcgc cgtttgaatg ctcgggattc      300
agagaaagat ttccagaaga aagaaagatt agagcatagc gctgtcgaaa ttgctgccgc      360
tagcgaattt gattatgttg tggttaatga tgatttgatt acagcatatc aagttttaag      420
aagtattttt atagctgaag aacataggat gagtcatggn tagaaaagat cgtttaacta      480
atgaaagact gaataagcta tttgatagcc cctttagttt ggntaattac gtaattaagc      540
nagctnagaa caaaattgct agaggagatg ttcgttcttc taac                       584
```

<210> SEQ ID NO 74
<211> LENGTH: 465
<212> TYPE: DNA
<213> ORGANISM: Chlamydia

<400> SEQUENCE: 74

```
gatccgaatt cggcacgagc tcgtgccgtt tgggatcgtg taatcgcatc ggagaatggt       60
taagaaatta ttttcgagtg aaagagctag gcgtaatcat tacagatagc catactactc      120
caatgcggcg tggagtactg ggtatcgggc tgtgttggta tggattttct ccattacaca      180
actatatagg atcgctagat tgtttcggtc gtcccttaca gatgacgcaa agtaatcttg      240
tagatgcctt agcagttgcg gctgttgttt gtatgggaga ggggaatgag caaacaccgt      300
tagcggtgat agagcaggca cctaatatgg tctaccattc atatcctact ctcgagaag       360 agtattgttc tttgcgcata gatgaaacag aggacttata cggaccttt ttgcaagcgg       420 ttaccgtgga gtcaagaaaa gaaatgatgg aggtgtttat gaatt                     465
```

<210> SEQ ID NO 75
<211> LENGTH: 545
<212> TYPE: DNA
<213> ORGANISM: Chlamydia

<400> SEQUENCE: 75

```
gaattcggca cgagatgaaa agttagcgtc acagggggatt ctcctaccaa agaattccga      60
aaagttttct tccaaaaacc tcttcctctc ttgattagtg atccctctgc aactacttta     120
ctatatgttc tgtgaaatat gcatagtctt caggattgga aaatccaaag tactcagtca     180
atccacgaat tttctctcta gcgatacgtg gaatttgact ctcataagaa tacaaagcag     240
ccactcctgc agctaaagaa tctcctgtac accaccgcat gaaagtagct actttcgctt     300
ttgctgcttc actaggctca tgagcctcta actcttctgg agtaactcct agagcaaaca     360
caaactgctt ccacaaatca atatgattag ggtaaccgtt ctcttcatcc atcaagttat     420
ctaacaataa cttacgcgcc tctaaatcat cgcaacgact atgaatcgca gataaatatt     480
taggaaaggc tttgatatgt aaataatagt ctttggcata cgcctgtaat tgctctttag     540
taagc                                                                545
```

<210> SEQ ID NO 76
<211> LENGTH: 797
<212> TYPE: DNA
<213> ORGANISM: Chlamydia
<220> FEATURE:
<221> NAME/KEY: unsure
<222> LOCATION: (788)
<223> OTHER INFORMATION: n=A,T,C or G
<220> FEATURE:
<221> NAME/KEY: unsure
<222> LOCATION: (789)

<223> OTHER INFORMATION: n=A,T,C or G

<400> SEQUENCE: 76

| | | | | | |
|---|---|---|---|---|---|
| gatccgaatt | cggcacgaga | tacgctagat | gcgataaatg | cggataatga | ggattatcct | 60 |
| aaaccaggtg | acttcccacg | atcttccttc | tctagtacgc | ctcctcatgc | tccagtacct | 120 |
| caatctgaga | ttccaacgtc | acctacctca | acacagcctc | catcaccta | acttgtaaaa | 180 |
| actgtaataa | aaagagcgcg | cttcctttat | gcaaaatcaa | tttgaacaac | tccttactga | 240 |
| attagggact | caaatcaaca | gccctcttac | tcctgattcc | aataatgcct | gtatagttcg | 300 |
| ctttggatac | aacaatgttg | ctgtacaaat | tgaagaggat | ggtaattcag | gattttagt | 360 |
| tgctggagtc | atgcttggaa | acttccaga | gaatacctt | agacaaaaaa | ttttcaaagc | 420 |
| tgctttgtct | atcaatggat | ctccgcaatc | taatattaaa | ggcactctag | gatacggtga | 480 |
| aatctctaac | caactctatc | tctgtgatcg | gcttaacatg | acctatctaa | atggagaaaa | 540 |
| gctcgcccgt | tacttagttc | tttttttcgca | gcatgccaat | atctggatgc | aatctatctc | 600 |
| aaaaggagaa | cttccagatt | tacatgctct | aggtatgtat | cacctgtaaa | ttatgccgtc | 660 |
| attatcccaa | tcccgacgta | tcatccagca | atcttccatt | cgaaagattt | ggaatcagat | 720 |
| agatacttct | cctaagcatg | ggggtatgcg | taccggttat | ttttctcttc | atactcaaaa | 780 |
| aaagttgnng | gggaata | | | | | 797 |

<210> SEQ ID NO 77
<211> LENGTH: 399
<212> TYPE: DNA
<213> ORGANISM: Chlamydia

<400> SEQUENCE: 77

| | | | | | |
|---|---|---|---|---|---|
| catatgcatc | accatcacca | tcacatgcca | cgcatcattg | gaattgatat | tcctgcaaag | 60 |
| aaaagttaa | aaataagtct | gacatatatt | tatggaatag | gatcagctcg | ttctgatgaa | 120 |
| atcattaaaa | agttgaagtt | agatcctgag | gcaagagcct | ctgaattaac | tgaagaagaa | 180 |
| gtaggacgac | tgaactctct | gctacaatca | gaatataccg | tagaagggga | tttgcgacgt | 240 |
| cgtgttcaat | cggatatcaa | aagattgatc | gccatccatt | cttatcgagg | tcagagacat | 300 |
| agactttctt | taccagtaag | aggacaacgt | acaaaaacta | attctcgtac | tcgaaaaggt | 360 |
| aaaagaaaaa | cagtcgcagg | taagaagaaa | taagaattc | | | 399 |

<210> SEQ ID NO 78
<211> LENGTH: 285
<212> TYPE: DNA
<213> ORGANISM: Chlamydia

<400> SEQUENCE: 78

| | | | | | |
|---|---|---|---|---|---|
| atgcatcacc | atcaccatca | catgagtcaa | aaaataaaa | actctgcttt | tatgcatccc | 60 |
| gtgaatattt | ccacagattt | agcagttata | gttggcaagg | gacctatgcc | cagaaccgaa | 120 |
| attgtaaaga | aagtttggga | atacattaaa | aaacacaact | gtcaggatca | aaaaaataaa | 180 |
| cgtaatatcc | ttcccgatgc | gaatcttgcc | aaagtctttg | gctctagtga | tcctatcgac | 240 |
| atgttccaaa | tgaccaaagc | cctttccaaa | catattgtaa | aataa | | 285 |

<210> SEQ ID NO 79
<211> LENGTH: 950
<212> TYPE: DNA
<213> ORGANISM: Chlamydia

<400> SEQUENCE: 79

```
aaattaactc gagcacaaat tacggcaatt gctgagcaaa agatgaagga catggatgtc    60
gttcttttag agtccgccga gagaatggtt gaagggactg cccgaagcat gggtgtagat   120
gtagagtaat tagttaaaga gctgcataat tatgacaaag catggaaaac gcattcgtgg   180
tatccaagag acttacgatt tagctaagtc gtattctttg ggtgaagcga tagatatttt   240
aaaacagtgt cctactgtgc gtttcgatca aacggttgat gtgtctgtta aattagggat   300
cgatccaaga aagagtgatc agcaaattcg tggttcggtt tctttacctc acggtacagg   360
taaagttttg cgaattttag tttttgctgc tggagataag gctgcagagg ctattgaagc   420
aggagcggac tttgttggta gcgacgactt ggtagaaaaa atcaaaggtg atgggttga    480 cttcgatgtt gcggttgcca ctcccgatat gatgagagag gtcggaaagc taggaaaagt   540
tttaggtcca agaaacctta tgcctacgcc taaagccgga actgtaacaa cagatgtggt   600
taaaactatt gcggaactgc gaaaaggtaa aattgaattt aaagctgatc gagctggtgt   660
atgcaacgtc ggagttgcga agctttcttt cgatagtgcg caaatcaaag aaaatgttga   720
agcgttgtgt gcagccttag ttaaagctaa gcccgcaact gctaaaggac aatatttagt   780
taatttcact atttcctcga ccatggggcc aggggttacc gtggatacta gggagttgat   840
tgcgttataa ttctaagttt aaagaggaaa atgaaagaa gagaaaaagt tgctgcttcg   900
cgaggttgaa gaaaagataa ccgcttctca aggttttatt ttgttgagat             950

<210> SEQ ID NO 80
<211> LENGTH: 395
<212> TYPE: DNA
<213> ORGANISM: Chlamydia

<400> SEQUENCE: 80
tttcaaggat tttgttttcc cgatcatctt actaaatgca gctccaacaa tcacatcatg    60
ggctggttta gcatctaagg caacagaagc tcctctgctg taataagtga attcttcaga   120
agtaggtgtt cctacttgcg atagcatcgt tcctagtcct gatatccaca ggttgttata   180
gctaacttca tcaaagcgag ctagattcat tttatcgttg agcaagcctt gtttgactgt   240
gaccattgac atttgagatc ccagaatcga gttcgcatag aaatgattgt ctctaggtac   300
ataagcccat tgtctataag agtcaaattt ccagagcgct gagatcgttc cattttgtag   360
ttgatcagga tccagagtga gtgttcctgt atatc                              395

<210> SEQ ID NO 81
<211> LENGTH: 2085
<212> TYPE: DNA
<213> ORGANISM: Chlamydia

<400> SEQUENCE: 81
atttggcgaa ggagtttggg ctacggctat taataaatca ttcgtgttcg ctgcctccaa    60
gaccagattg tgtactttct tatgaagaat ctcctattga gcaaatgttg cgttggggag   120
agtctcagtt agaacaattt gctcaagtag gtttagatac aagttggcaa gttgttttcg   180
atccaggaat aggatttggg aagactcccg ttcagtcgat gttattgatg gatggagtaa   240
agcagtttaa acgtgtttta gagtgtcctg tattaatagg ccattctaga aaatcgtgtt   300
tgagtatgtt gggccgattt aatagtgacg atcgtgattg ggaaacgatc ggctgttctg   360
tatctcttca tgatcgagga gttgattatc tacgtgtgca tcaggttgaa ggtaacagac   420
gtgccttagc cgctgctgct tgggctggta tgtttgtatg atccaagcaa caggtatcgt   480
```

-continued

```
tgctattgat cccagaggag tgatgggagc tttaggcaag ctcccttgga gttatcccga      540
agatctacgt ttttttgcag aaaccattcg aaatcatccc atcattatgg gacgaaagac      600
ttgggagtct cttccagaca agtataagca tgggcgggat atcgttgtct tttctcgcag      660
gatgcatcca ccacaatgca taggagtttc ttcctttgca gagtatggga cactatcttt      720
gaatcatccg tttttaattg ggggagcgga gctctttgaa agttttttcc aacaaaacct      780
tctgaaagct tgttttgtca cacatatcaa aaagaaatat tggggcgata ctttcttccc      840
tatcacgcga ttatcaggat ggaagaagga atgtatttgt aatacagagg atttcagtat      900
ttattattat gaaaataact ccgatcaaaa cacgtaaagt atttgcacat gattcgcttc      960
aagagatctt gcaagaggct tgccgcctc tgcaagaacg gagtgtggta gttgtctctt     1020
caaagattgt gagtttatgt gaaggcgctg tcgctgatgc aagaatgtgc aaagcagagt    1080
tgataaaaaa agaagcggat gcttatttgt tttgtgagaa aagcgggata tatctaacga    1140
aaaaagaagg tattttgatt ccttctgcag ggattgatga atcgaatacg gaccagcctt    1200 ttgtttata tcctaaagat attttgggat cgtgtaatcg catcggagaa tggttaagaa    1260
attattttcg agtgaaagag ctaggcgtaa tcattacaga tagccatact actccaatgc    1320
ggcgtggagt actgggtatc gggctgtgtt ggtatggatt ttctccatta cacaactata    1380
taggatcgct agattgtttc ggtcgtccct tacagatgac gcaaagtaat cttgtagatg    1440
ccttagcagt tgcggctgtt gtttgtatgg gagagggaa tgagcaaaca ccgttagcgg    1500
tgatagagca ggcaccctaat atggtctacc attcatatcc tacttctcga gaagagtatt    1560
gttctttgcg catagatgaa acagaggact tatacgacc tttttttgcaa gcggttacgt    1620 ggagtcaaga aaagaaatga tggaggtgtt tatgaatttt ttagatcagt tagattaat    1680 tattcaaaat aagcatatgc tagaacacac gttttatgtg aaatggtcga agggggagct    1740
tactaaagag caattacagg cgtatgccaa agactattat ttacatatca aagcctttcc    1800
taaatattta tctgcgattc atagtcgttg cgatgattta gaggcgcgta agttattgtt    1860
agataacttg atggatgaag agaacggtta ccctaatcat attgatttgt ggaagcagtt    1920
tgtgtttgct ctaggagtta ctccagaaga gttagaggct catgagccta gtgaagcagc    1980
aaaagcgaaa gtagctactt tcatgcgtgt gtgtacagga gattctttag ctgcaggagt    2040
ggctgctttg tattcttatg agagtcaaat tccacgtatc gcctc                    2085
```

<210> SEQ ID NO 82
<211> LENGTH: 405
<212> TYPE: DNA
<213> ORGANISM: Chlamydia

<400> SEQUENCE: 82

```
ttcatcggtc tagttcgcta ttctactctc caatggttcc gcattttttgg gcagagcttc      60 gcaatcatta tgcaacgagt ggtttgaaaa gcgggtacaa tattgggagt accgatgggt     120
ttctccctgt cattgggcct gttatatggg agtcggaggg tcttttccgc gcttatattt     180
cttcggtgac tgatggggat ggtaagagcc ataaagtagg atttctaaga attcctacat     240
atagttggca ggacatggaa gatttttgatc cttcaggacc gcctccttgg gaagaattgt     300
attggctcca taaagggagg agaaaacttc gatatatggga atcgtatcaa ggtgaaagta    360
gcaaaaaata aattagctcc tccattccga actgcagaat ttgat                      405
```

<210> SEQ ID NO 83
<211> LENGTH: 379

<212> TYPE: DNA
<213> ORGANISM: Chlamydia

<400> SEQUENCE: 83

```
tataccattc gtttgaaagt gcctttgacg ggagaaagtg ttttgaaga tcaatgcaaa      60
ggtcgtgtcg ttttcccttg ggcagatgtt gacgatcaag ttttggttaa atcagacggg     120
ttccctacgt atcactttgc taatgtagtt gatgatcatt tgatgggat taccatgtg      180
ttgcgagggg aagagtggtt aagttctaca cctaaacacc ttcttcttta caaagctttt    240
gggtgggagc ctccgcagtt tttccatatg ccgcttcttc taaatcctga tggaagtaag    300
ctttccaaga gaaagaatcc tacttctatt ttttactatc gggatgctgg atacaaaaaa    360
gaagcgttca tgaatttcc                                                 379
```

<210> SEQ ID NO 84
<211> LENGTH: 715
<212> TYPE: DNA
<213> ORGANISM: Chlamydia

<400> SEQUENCE: 84

```
tcaatcctgt attaataatt ctggttctta gactacataa attaggaacg cctgatgagt     60
atccataact aatcgcgtag ggcttagaat caccttctcg taccaaagct agaacaacgc    120
cgccttccat tcttgatgca ataatatctg ctgagactaa aacatgctc ccagagcttt    180
tgggtgtgac tgtgaatttt cctatttcag ttcctcctaa taaagtttca atgttcctgg    240
gagtgaataa cccgttgcat tgaattttat tagtgattgg aaagttgtta aaagctttca    300
acaaacctag agaagggtct gttgtgattt tgtctaaaat tcttggact gtactatcaa    360
caatagtatc agcaattcca ccaagaattt gatctcccaa ctttctaga ataagctggt    420
aagctttttc cgcatccaaa ccaattgtaa tagaagcatt ggttgatgga ttattggaga    480
ctgttaaaga tattccatca gaagctgtca ttttggctgc gacaggtgtt gatgttgtcc    540
caaggattat tgctggtcc ttgagcggct ctgtcatttg cccaactttg atattatcag    600
caaagacgca gttttgagtg ttatacaaat aaaaaccaga atttcccatt ttaaaactct    660
ttttatttt gagctttaaa taaattaggt tttagtttc agtttgcta ttaat          715
```

<210> SEQ ID NO 85
<211> LENGTH: 476
<212> TYPE: DNA
<213> ORGANISM: Chlamydia

<400> SEQUENCE: 85

```
ctcgtgccgc tcgtgccgct cgtgccggtc ttttagaaga gcgtgaagct ttaaataatt     60
cgattacgtt tatcatggat aagcgtaatt ggatagaaac cgagtctgaa caggtacaag    120
tggttttcag agatagtaca gcttgcttag gaggaggcgc tattgcagct caagaaattg    180
tttctattca gaacaatcag gctgggattt ccttcgaggg aggtaaggct agtttcggag    240
gaggtattgc gtgtggatct ttttcttccg caggcggtgc ttctgtttta gggactattg    300
atatttcgaa gaatttaggc gcgatttcgt tctctcgtac tttatgtacg acctcagatt    360
taggacaaat ggagtaccag ggaggaggag ctctatttgg tgaaaatatt tctctttctg    420
agaatgctgg tgtgctcacc tttaaagaca acattgtgaa gacttttgct tcgaat       476
```

<210> SEQ ID NO 86
<211> LENGTH: 1551
<212> TYPE: DNA

<213> ORGANISM: Chlamydia

<400> SEQUENCE: 86

```
gcgtatcgat atttcttctg ttacattctt tatagggatt ctgttggctg ttaatgcgct      60
aacctactct catgtattac gggatttatc tgtgagtatg gatgcgctgt tttctcgtaa     120
cacgcttgct gttcttttag gtttagtctc tagcgtttta gataatgtgc cattagtcgc     180
tgcaacaata ggtatgtatg acttacctat gaacgatcct ctttggaaac tcattgccta     240
tacagcaggc acaggggaa gtattctcat cattggatcc gctgcaggtg ttgcctacat      300
gggaatggaa aaagtgagtt tcggctggta tgtcaaacac gcttcttgga ttgctttagc     360
cagttatttt ggaggtctag cagtctattt tctaatggaa aattgtgtga atttgttcgt     420
ttgaggtagt cagtatggca gagtttcttt aaaaattctt ttaataaaag gttctctgc     480
ctattctagg cccctttttg aatggaaaaa tgggttttg gagaacatcg attatgaaaa      540
tgaataggat ttggctatta ctgcttacct tttcttctgc catacattct cctgtacgag     600
gagaaagctt ggtttgcaag aatgctcttc aagatttgag tttttagag catttattac      660
aggttaaata tgctcctaaa acatggaaag agcaatactt aggatgggat cttgttcaaa     720
gctccgtttc tgcacagcag aagcttcgta cacaagaaaa tccatcaaca gttttttgcc     780
agcaggtcct tgctgatttt atcggaggat taaatgactt tcacgctgga gtaactttct     840
ttgcgataga aagtgcttac cttccttata ccgtacaaaa aagtagtgac ggccgttct      900
actttgtaga tatcatgact ttttcttcag agatccgtgt tggagatgag ttgctagagg     960
tggatggggc gcctgtccaa gatgtgctcg ctactctata tggaagcaat cacaaaggga    1020
ctgcagctga gagtcggct gctttaagaa cactattttc tcgcatggcc tctttagggc     1080
acaaagtacc ttctgggcgc actactttaa agattcgtcg cccttttggt actacgagag    1140
aagttcgtgt gaaatggcgt tatgttcctg aaggtgtagg agatttggct accatagctc    1200
cttctatcag ggctccacag ttacagaaat cgatgagaag ctttttccct aagaaagatg    1260
atgcgtttca tcggtctagt tcgctattct actctccaat ggttccgcat ttttgggcag    1320
agcttcgcaa tcattatgca acgagtggtt tgaaaagcgg gtacaatatt gggagtaccg    1380
atgggtttct ccctgtcatt gggcctgtta tatgggagtc ggagggtctt ttccgcgctt    1440
atatttcttc ggtgactgat ggggatggta agagccataa agtaggattt ctaagaattc    1500
ctacatatag ttggcaggac atggaagatt ttgatccttc aggaccgcct c             1551
```

<210> SEQ ID NO 87
<211> LENGTH: 3031
<212> TYPE: DNA
<213> ORGANISM: Chlamydia

<400> SEQUENCE: 87

```
atgtaggccc tcaagcggtt ttattgttag accaaattcg agatctattc gttgggtcta      60
aagatagtca ggctgaagga cagtataggt taattgtagg agatccaagt tctttccaag     120
agaaagatgc agatactctt cccgggaagg tagagcaaag tactttgttc tcagtaacca     180
atcccgtggt tttccaaggt gtggaccaac aggatcaagt ctcttcccaa gggttaattt     240
gtagttttac gagcagcaac cttgattctc cccgtgacgg agaatctttt ttaggtattg     300
cttttgttgg ggatagtagt aaggctgaaa tcacattaac tgacgtgaaa gcttcttgt      360
ctggagcggc tttatattct acagaagatc ttatctttga aaagattaag ggtggattgg     420
aatttgcatc atgttcttct ctagaacagg ggggagcttg tgcagctcaa agtattttga     480
```

```
ttcatgattg tcaaggattg caggttaaac actgtactac agccgtgaat gctgaggggt    540
ctagtgcgaa tgatcatctt ggatttggag gaggcgcttt ctttgttacg ggttctcttt    600
ctggagagaa aagtctctat atgcctgcag agatatggt agttgcgaat tgtgatgggg    660
ctatatcttt tgaaggaaac agcgcgaact ttgctaatgg aggagcgatt gctgcctctg    720
ggaaagtgct ttttgtcgct aatgataaaa agacttcttt tatagagaac cgagctttgt    780
ctggaggagc gattgcagcc tcttctgata ttgcctttca aaactgcgca gaactagttt    840
tcaaaggcaa ttgtgcaatt ggaacagagg ataaaggttc tttaggtgga ggggctatat    900
cttctctagg caccgttctt ttgcaaggga atcacgggat aacttgtgat aataatgagt    960
ctgcttcgca aggaggcgcc attttggca aaaattgtca gatttctgac aacgaggggc   1020
cagtggtttt cagagatagt acagcttgct taggaggagg cgctattgca gctcaagaaa   1080
ttgtttctat tcagaacaat caggctggga tttccttcga gggaggtaag gctagtttcg   1140
gaggaggtat tgcgtgtgga tcttttttctt ccgcaggcgg tgcttctgtt ttagggacta   1200
ttgatatttc gaagaattta ggcgcgattt cgttctctcg tactttatgt acgacctcag   1260
atttaggaca aatggagtac cagggaggag gagctctatt tggtgaaaat atttctcttt   1320
ctgagaatgc tggtgtgctc acctttaaag acaacattgt gaagacttttt gcttcgaatg   1380 ggaaaattct gggaggagga gcgattttag ctactggtaa ggtggaaatt accaataatt   1440
ccggaggaat ttcttttaca ggaaatgcga gagctccaca agctcttcca actcaagagg   1500
agtttccttt attcagcaaa aaagaagggc gaccactctc ttcaggatat tctggggggag   1560 gagcgatttt aggaagagaa gtagctattc tccacaacgc tgcagtagta tttgagcaaa   1620
atcgtttgca gtgcagcgaa gaagaagcga cattattagg ttgttgtgga ggaggcgctg   1680
ttcatgggat ggatagcact tcgattgttg gcaactcttc agtaagattt ggtaataatt   1740
acgcaatggg acaaggagtc tcaggaggag ctctttttatc taaaacagtg cagttagctg   1800
gaaatggaag cgtcgatttt tctcgaaata ttgctagttt gggaggacgc aatgttctgt   1860
tagcttcaga aacctttgct tccagagcaa atacatctcc ttcatcgctt cgctccttat   1920
atttccaagt aacctcatcc ccctctaatt gcgctaattt acatcaaatg cttgcttctt   1980
actcgccatc agagaaaacc gctgttatgg agtttctagt gaatggcatg gtagcagatt   2040
taaaatcgga gggcccttcc attcctcctg caaaattgca agtatatatg acggaactaa   2100
gcaatctcca agccttacac tctgtagata gcttttttga tagaaatatt gggaacttgg   2160
aaaatagctt aaagcatgaa ggacatgccc ctattccatc cttaacgaca ggaaatttaa   2220
ctaaaacctt cttacaatta gtagaagata aattcccttc ctcttccaaa gctcaaaagg   2280
cattaaatga actggtaggc ccagatactg gtcctcaaac tgaagttttta aacttattct   2340 tccgcgctct taatggctgt tcgcctagaa tattctctgg agctgaaaaa aaacagcagc   2400
tggcatcggt tatcacaaat acgctagatg cgataaatgc ggataatgag gattatccta   2460
aaccaggtga cttcccacga tcttccttct ctagtacgcc tcctcatgct ccagtaccte   2520 aatctgagat tccaacgtca cctacctcaa cacagcctcc atcaccctaa cttgtaaaaa   2580
ctgtaataaa aagagcgcgc ttcctttatg caaaatcaat ttgaacaact ccttactgaa   2640
ttagggactc aaatcaacag ccctcttact cctgattcca ataatgcctg tatagttcgc   2700
tttggataca acaatgttgc tgtacaaatt gaagaggatg gtaattcagg attttttagtt   2760 gctggagtca tgcttggaaa acttccagag aatacccttta gacaaaaaat tttcaaagct   2820
```

-continued

```
gctttgtcta tcaatggatc tccgcaatct aatattaaag gcactctagg atacggtgaa    2880
atctctaacc aactctatct ctgtgatcgg cttaacatga cctatctaaa tggagaaaag    2940
ctcgcccgtt acttagttct tttttcgcag catgccaata tctggatgca atctatctca    3000
aaaggagaac ttccagattt acatgctcta g                                   3031
```

<210> SEQ ID NO 88
<211> LENGTH: 976
<212> TYPE: DNA
<213> ORGANISM: Chlamydia

<400> SEQUENCE: 88

```
aggtggatgg ggcgcctgtc caagatgtgc tcgctactct atatggaagc aatcacaaag     60
ggactgcagc tgaagagtcg gctgctttaa gaacactatt ttctcgcatg gcctctttag    120
ggcacaaagt accttctggg cgcactactt taaagattcg tcgtcctttt ggtactacga    180
gagaagttcg tgtgaaatgg cgttatgttc ctgaaggtgt aggagatttg gctaccatag    240
ctccttctat cagggctcca cagttacaga atcgatgag aagcttttc cctaagaaag      300 atgatgcgtt tcatcggtct agttcgctat tctactctcc aatggttccg cattttggg     360 cagagcttcg caatcattat gcaacgagtg gtttgaaaag cgggtacaat attgggagta    420
ccgatgggtt tctccctgtc attgggcctg ttatatggga gtcggagggt cttttccgcg    480
cttatatttc ttcggtgact gatggggatg gtaagagcca taaagtagga tttctaagaa    540
ttcctacata tagttggcag gacatggaag attttgatcc ttcaggaccg cctccttggg    600
aagaatttgc taagattatt caagtatttt cttctaatac agaagctttg attatcgacc    660
aaacgaacaa cccaggtggt agtgtccttt atctttatgc actgctttcc atgttgacag    720
accgtccttt agaacttcct aaacatagaa tgattctgac tcaggatgaa gtggttgatg    780
ctttagattg gttaaccctg ttggaaaacg tagacacaaa cgtggagtct cgccttgctc    840
tgggagacaa catggaagga tatactgtgg atctacaggt tgccgagtat ttaaaaagct    900
ttggacgtca gtattgaat tgttggagta aagggatat cgagttatca acacctattc      960
ctcttttggg ttttga                                                    976
```

<210> SEQ ID NO 89
<211> LENGTH: 94
<212> TYPE: PRT
<213> ORGANISM: Chlamydia

<400> SEQUENCE: 89

```
Met His His His His His His Met Ser Gln Lys Asn Lys Asn Ser Ala
                 5                  10                  15

Phe Met His Pro Val Asn Ile Ser Thr Asp Leu Ala Val Ile Val Gly
             20                  25                  30

Lys Gly Pro Met Pro Arg Thr Glu Ile Val Lys Lys Val Trp Glu Tyr
         35                  40                  45

Ile Lys Lys His Asn Cys Gln Asp Gln Lys Asn Lys Arg Asn Ile Leu
     50                  55                  60

Pro Asp Ala Asn Leu Ala Lys Val Phe Gly Ser Ser Asp Pro Ile Asp
 65                  70                  75                  80

Met Phe Gln Met Thr Lys Ala Leu Ser Lys His Ile Val Lys
                 85                  90
```

<210> SEQ ID NO 90
<211> LENGTH: 474

-continued

<212> TYPE: PRT
<213> ORGANISM: Chlamydia

<400> SEQUENCE: 90

```
Met Ala Ser His His His His His His Met Asn Glu Ala Phe Asp Cys
                  5                  10                  15

Val Val Ile Gly Ala Gly Pro Gly Gly Tyr Val Ala Ala Ile Thr Ala
             20                  25                  30

Ala Gln Ala Gly Leu Lys Thr Ala Leu Ile Glu Lys Arg Glu Ala Gly
         35                  40                  45

Gly Thr Cys Leu Asn Arg Gly Cys Ile Pro Ser Lys Ala Leu Leu Ala
     50                  55                  60

Gly Ala Glu Val Val Thr Gln Ile Arg His Ala Asp Gln Phe Gly Ile
 65                  70                  75                  80

His Val Glu Gly Phe Ser Ile Asn Tyr Pro Ala Met Val Gln Arg Lys
                 85                  90                  95

Asp Ser Val Val Arg Ser Ile Arg Asp Gly Leu Asn Gly Leu Ile Arg
            100                 105                 110

Ser Asn Lys Ile Thr Val Phe Ser Gly Arg Gly Ser Leu Ile Ser Ser
        115                 120                 125

Thr Glu Val Lys Ile Leu Gly Glu Asn Pro Ser Val Ile Lys Ala His
    130                 135                 140

Ser Ile Ile Leu Ala Thr Gly Ser Glu Pro Arg Ala Phe Pro Gly Ile
145                 150                 155                 160

Pro Phe Ser Ala Glu Ser Pro Arg Ile Leu Cys Ser Thr Gly Val Leu
                165                 170                 175

Asn Leu Lys Glu Ile Pro Gln Lys Met Ala Ile Ile Gly Gly Gly Val
            180                 185                 190

Ile Gly Cys Glu Phe Ala Ser Leu Phe His Thr Leu Gly Ser Glu Val
        195                 200                 205

Ser Val Ile Glu Ala Ser Ser Gln Ile Leu Ala Leu Asn Asn Pro Asp
    210                 215                 220

Ile Ser Lys Thr Met Phe Asp Lys Phe Thr Arg Gln Gly Leu Arg Phe
225                 230                 235                 240

Val Leu Glu Ala Ser Val Ser Asn Ile Glu Asp Ile Gly Asp Arg Val
                245                 250                 255

Arg Leu Thr Ile Asn Gly Asn Val Glu Glu Tyr Asp Tyr Val Leu Val
            260                 265                 270

Ser Ile Gly Arg Arg Leu Asn Thr Glu Asn Ile Gly Leu Asp Lys Ala
        275                 280                 285

Gly Val Ile Cys Asp Glu Arg Gly Val Ile Pro Thr Asp Ala Thr Met
    290                 295                 300

Arg Thr Asn Val Pro Asn Ile Tyr Ala Ile Gly Asp Ile Thr Gly Lys
305                 310                 315                 320

Trp Gln Leu Ala His Val Ala Ser His Gln Gly Ile Ile Ala Ala Arg
                325                 330                 335

Asn Ile Gly Gly His Lys Glu Glu Ile Asp Tyr Ser Ala Val Pro Ser
            340                 345                 350

Val Ile Phe Thr Phe Pro Glu Val Ala Ser Val Gly Leu Ser Pro Thr
        355                 360                 365

Ala Ala Gln Gln Gln Lys Ile Pro Val Lys Val Thr Lys Phe Pro Phe
    370                 375                 380

Arg Ala Ile Gly Lys Ala Val Ala Met Gly Glu Ala Asp Gly Phe Ala
385                 390                 395                 400
```

```
Ala Ile Ile Ser His Glu Thr Thr Gln Gln Ile Leu Gly Ala Tyr Val
                405                 410                 415

Ile Gly Pro His Ala Ser Ser Leu Ile Ser Glu Ile Thr Leu Ala Val
            420                 425                 430

Arg Asn Glu Leu Thr Leu Pro Cys Ile Tyr Glu Thr Ile His Ala His
        435                 440                 445

Pro Thr Leu Ala Glu Val Trp Ala Glu Ser Ala Leu Leu Ala Val Asp
    450                 455                 460

Thr Pro Leu His Met Pro Pro Ala Lys Lys
465                 470
```

<210> SEQ ID NO 91
<211> LENGTH: 129
<212> TYPE: PRT
<213> ORGANISM: Chlamydia

<400> SEQUENCE: 91

```
Met His His His His His Met Pro Arg Ile Ile Gly Ile Asp Ile
                5                   10                  15

Pro Ala Lys Lys Lys Leu Lys Ile Ser Leu Thr Tyr Ile Tyr Gly Ile
            20                  25                  30

Gly Ser Ala Arg Ser Asp Glu Ile Ile Lys Lys Leu Lys Leu Asp Pro
        35                  40                  45

Glu Ala Arg Ala Ser Glu Leu Thr Glu Glu Val Gly Arg Leu Asn
    50                  55                  60

Ser Leu Leu Gln Ser Glu Tyr Thr Val Glu Gly Asp Leu Arg Arg
65                  70                  75                  80

Val Gln Ser Asp Ile Lys Arg Leu Ile Ala Ile His Ser Tyr Arg Gly
                85                  90                  95

Gln Arg His Arg Leu Ser Leu Pro Val Arg Gly Gln Arg Thr Lys Thr
            100                 105                 110

Asn Ser Arg Thr Arg Lys Gly Lys Arg Lys Thr Val Ala Gly Lys Lys
        115                 120                 125

Lys
```

<210> SEQ ID NO 92
<211> LENGTH: 202
<212> TYPE: PRT
<213> ORGANISM: Chlamydia

<400> SEQUENCE: 92

```
Met His His His His His Met Gly Ser Leu Val Gly Arg Gln Ala
                5                   10                  15

Pro Asp Phe Ser Gly Lys Ala Val Val Cys Gly Glu Glu Lys Glu Ile
            20                  25                  30

Ser Leu Ala Asp Phe Arg Gly Lys Tyr Val Val Leu Phe Phe Tyr Pro
        35                  40                  45

Lys Asp Phe Thr Tyr Val Cys Pro Thr Glu Leu His Ala Phe Gln Asp
    50                  55                  60

Arg Leu Val Asp Phe Glu Glu His Gly Ala Val Val Leu Gly Cys Ser
65                  70                  75                  80

Val Asp Asp Ile Glu Thr His Ser Arg Trp Leu Thr Val Ala Arg Asp
                85                  90                  95

Ala Gly Gly Ile Glu Gly Thr Gly Tyr Pro Leu Leu Ala Asp Pro Ser
            100                 105                 110
```

```
Phe Lys Ile Ser Glu Ala Phe Gly Val Leu Asn Pro Glu Gly Ser Leu
            115                 120                 125

Ala Leu Arg Ala Thr Phe Leu Ile Asp Lys His Gly Val Ile Arg His
        130                 135                 140

Ala Val Ile Asn Asp Leu Pro Leu Gly Arg Ser Ile Asp Glu Glu Leu
145                 150                 155                 160

Arg Ile Leu Asp Ser Leu Ile Phe Phe Glu Asn His Gly Met Val Cys
                165                 170                 175

Pro Ala Asn Trp Arg Ser Gly Glu Arg Gly Met Val Pro Ser Glu Glu
            180                 185                 190

Gly Leu Lys Glu Tyr Phe Gln Thr Met Asp
            195                 200
```

<210> SEQ ID NO 93
<211> LENGTH: 19
<212> TYPE: PRT
<213> ORGANISM: Artificial Sequence
<220> FEATURE:
<223> OTHER INFORMATION: made in a lab

<400> SEQUENCE: 93

```
Glu Asn Ser Leu Gln Asp Pro Thr Asn Lys Arg Asn Ile Asn Pro Asp
1               5                   10                  15

Asp Lys Leu
```

<210> SEQ ID NO 94
<211> LENGTH: 20
<212> TYPE: PRT
<213> ORGANISM: Artificial Sequence
<220> FEATURE:
<223> OTHER INFORMATION: Made in a lab

<400> SEQUENCE: 94

```
Asp Pro Thr Asn Lys Arg Asn Ile Asn Pro Asp Asp Lys Leu Ala Lys
1               5                   10                  15

Val Phe Gly Thr
            20
```

<210> SEQ ID NO 95
<211> LENGTH: 20
<212> TYPE: PRT
<213> ORGANISM: Artificial Sequence
<220> FEATURE:
<223> OTHER INFORMATION: Made in a lab

<400> SEQUENCE: 95

```
Lys Arg Asn Ile Asn Pro Asp Asp Lys Leu Ala Lys Val Phe Gly Thr
1               5                   10                  15

Glu Lys Pro Ile
            20
```

<210> SEQ ID NO 96
<211> LENGTH: 20
<212> TYPE: PRT
<213> ORGANISM: Artificial Sequence
<220> FEATURE:
<223> OTHER INFORMATION: Made in a lab

<400> SEQUENCE: 96

```
Asp Asp Lys Leu Ala Lys Val Phe Gly Thr Glu Lys Pro Ile Asp Met
1               5                   10                  15

Phe Gln Met Thr
```

```
<210> SEQ ID NO 97
<211> LENGTH: 20
<212> TYPE: PRT
<213> ORGANISM: Artificial Sequence
<220> FEATURE:
<223> OTHER INFORMATION: Made in a lab

<400> SEQUENCE: 97

Lys Val Phe Gly Thr Glu Lys Pro Ile Asp Met Phe Gln Met Thr Lys
 1               5                  10                  15

Met Val Ser Gln
            20

<210> SEQ ID NO 98
<211> LENGTH: 20
<212> TYPE: PRT
<213> ORGANISM: Artificial Sequence
<220> FEATURE:
<223> OTHER INFORMATION: Made in a lab

<400> SEQUENCE: 98

Asn Lys Arg Asn Ile Asn Pro Asp Asp Lys Leu Ala Lys Val Phe Gly
 1               5                  10                  15

Thr Glu Lys Pro
            20

<210> SEQ ID NO 99
<211> LENGTH: 16
<212> TYPE: PRT
<213> ORGANISM: Artificial Sequence
<220> FEATURE:
<223> OTHER INFORMATION: Made in a lab

<400> SEQUENCE: 99

Asn Lys Arg Asn Ile Leu Pro Asp Ala Asn Leu Ala Lys Val Phe Gly
 1               5                  10                  15

<210> SEQ ID NO 100
<211> LENGTH: 15
<212> TYPE: PRT
<213> ORGANISM: Artificial Sequence
<220> FEATURE:
<223> OTHER INFORMATION: Made in a lab

<400> SEQUENCE: 100

Lys Met Trp Asp Tyr Ile Lys Glu Asn Ser Leu Gln Asp Pro Thr
 1               5                  10                  15

<210> SEQ ID NO 101
<211> LENGTH: 20
<212> TYPE: PRT
<213> ORGANISM: Artificial Sequence
<220> FEATURE:
<223> OTHER INFORMATION: Made in a lab

<400> SEQUENCE: 101

Thr Glu Ile Val Lys Lys Val Trp Glu Tyr Ile Lys Lys His Asn Cys
 1               5                  10                  15

Gln Asp Gln Lys
            20

<210> SEQ ID NO 102
<211> LENGTH: 20
```

<212> TYPE: PRT
<213> ORGANISM: Artificial Sequence
<220> FEATURE:
<223> OTHER INFORMATION: Made in a lab

<400> SEQUENCE: 102

Lys Val Trp Glu Tyr Ile Lys Lys His Asn Cys Gln Asp Gln Lys Asn
1               5                   10                  15

Lys Arg Asn Ile
            20

<210> SEQ ID NO 103
<211> LENGTH: 15
<212> TYPE: PRT
<213> ORGANISM: Artificial Sequence
<220> FEATURE:
<223> OTHER INFORMATION: Made in a lab

<400> SEQUENCE: 103

Lys Val Trp Glu Tyr Ile Lys Lys His Asn Cys Gln Asp Gln Lys
1               5                   10                  15

<210> SEQ ID NO 104
<211> LENGTH: 20
<212> TYPE: PRT
<213> ORGANISM: Artificial Sequence
<220> FEATURE:
<223> OTHER INFORMATION: Made in a lab

<400> SEQUENCE: 104

Ala Glu Leu Thr Glu Glu Val Gly Arg Leu Asn Ala Leu Leu Gln
1               5                   10                  15

Ser Asp Tyr Val
            20

<210> SEQ ID NO 105
<211> LENGTH: 21
<212> TYPE: PRT
<213> ORGANISM: Artificial Sequence
<220> FEATURE:
<223> OTHER INFORMATION: Made in a lab

<400> SEQUENCE: 105

Leu Gln Ser Asp Tyr Val Val Glu Gly Asp Leu Arg Arg Arg Val Gln
1               5                   10                  15

Ser Asp Ile Lys Arg
            20

<210> SEQ ID NO 106
<211> LENGTH: 20
<212> TYPE: PRT
<213> ORGANISM: Artificial Sequence
<220> FEATURE:
<223> OTHER INFORMATION: Made in a lab

<400> SEQUENCE: 106

Met Pro Arg Ile Ile Gly Ile Asp Ile Pro Ala Lys Lys Lys Leu Lys
1               5                   10                  15

Ile Ser Leu Thr
            20

<210> SEQ ID NO 107
<211> LENGTH: 20
<212> TYPE: PRT
<213> ORGANISM: Artificial Sequence

```
<220> FEATURE:
<223> OTHER INFORMATION: Made in a lab

<400> SEQUENCE: 107

Ala Glu Leu Thr Glu Glu Glu Val Gly Arg Leu Asn Ala Leu Leu Gln
 1               5                  10                  15

Ser Asp Tyr Val
            20

<210> SEQ ID NO 108
<211> LENGTH: 20
<212> TYPE: PRT
<213> ORGANISM: Artificial Sequence
<220> FEATURE:
<223> OTHER INFORMATION: Made in a lab

<400> SEQUENCE: 108

Leu Asn Ala Leu Leu Gln Ser Asp Tyr Val Val Glu Gly Asp Leu Arg
 1               5                  10                  15

Arg Arg Val Gln
            20

<210> SEQ ID NO 109
<211> LENGTH: 20
<212> TYPE: PRT
<213> ORGANISM: Artificial Sequence
<220> FEATURE:
<223> OTHER INFORMATION: Made in a lab

<400> SEQUENCE: 109

Leu Asn Ser Leu Leu Gln Ser Glu Tyr Thr Val Glu Gly Asp Leu Arg
 1               5                  10                  15

Arg Arg Val Gln
            20
```

COMPOUNDS AND METHODS FOR TREATMENT AND DIAGNOSIS OF CHLAMYDIAL INFECTION

REFERENCE TO RELATED APPLICATIONS

This application is a continuation-in-part of U.S. patent application Ser. No. 09/288,594, filed Apr. 8, 1999, now U.S. Pat. No. 6,447,779, which is a continuation-in-part of U.S. patent application Ser. No. 09/208,277, filed Dec. 8, 1998 now U.S. Pat. No. 6,166,177.

TECHNICAL FIELD

The present invention relates generally to the detection and treatment of Chlamydial infection. In particular, the invention is related to polypeptides comprising a Chlamydia antigen and the use of such polypeptides for the serodiagnosis and treatment of Chlamydial infection.

BACKGROUND OF THE INVENTION

Chlamydiae are intracellular bacterial pathogens that are responsible for a wide variety of important human and animal infections. *Chlamydia trachomatis* is one of the most common causes of sexually transmitted diseases and can lead to pelvic inflammatory disease (PID), resulting in tubal obstruction and infertility. *Chlamydia trachomatis* may also play a role in male infertility. In 1990, the cost of treating PID in the US was estimated to be $4 billion. Trachoma, due to ocular infection with *Chlamydia trachomatis*, is the leading cause of preventable blindness worldwide. *Chlamydia pneumonia* is a major cause of acute respiratory tract infections in humans and is also believed to play a role in the pathogenesis of atherosclerosis and, in particular, coronary heart disease. Individuals with a high titer of antibodies to *Chlamydia pneumonia* have been shown to be at least twice as likely to suffer from coronary heart disease as seronegative individuals. Chlamydial infections thus constitute a significant health problem both in the US and worldwide.

Chlamydial infection is often asymptomatic. For example, by the time a woman seeks medical attention for PID, irreversible damage may have already occurred resulting in infertility. There thus remains a need in the art for improved vaccines and pharmaceutical compositions for the prevention and treatment of Chlamydia infections. The present invention fulfills this need and further provides other related advantages.

SUMMARY OF THE INVENTION

The present invention provides compositions and methods for the diagnosis and treatment of Chlamydia infection. In one aspect, polypeptides are provided comprising an immunogenic portion of a Chlamydia antigen, or a variant of such an antigen. In one embodiment, the antigen comprises an amino acid sequence encoded by a DNA sequence selected from the group consisting of (a) a sequence of SEQ ID NO: 1, 15, 21–25, 44–64, 66–76 or 79–88; (b) the complements of said sequences; and (c) sequences that hybridize to a sequence of (a) or (b) under moderately stringent conditions. In a specific embodiment, a polypeptide comprising an amino acid sequence of SEQ ID NO: 5 is provided.

In a related aspect, polynucleotide sequences encoding the above polypeptides, recombinant expression vectors comprising one or more of these polynucleotide sequences and host cells transformed or transfected with such expression vectors are also provided.

In another aspect, the present invention provides fusion proteins comprising an inventive polypeptide, or, alternatively, an inventive polypeptide and a known Chlamydia antigen. In yet another aspect, the present invention provides antibodies, both polyclonal and monoclonal, that bind to the polypeptides described above.

Within other aspects, the present invention provides pharmaceutical compositions that comprise one or more Chlamydia polypeptides disclosed herein, or a polynucleotide molecule encoding such a polypeptide, and a physiologically acceptable carrier. The invention also provides vaccines comprising one or more of the disclosed polypeptides and a non-specific immune response enhancer, together with vaccines comprising one or more polynucleotide sequences encoding such polypeptides and a non-specific immune response enhancer.

In yet another aspect, methods are provided for inducing protective immunity in a patient, comprising administering to a patient an effective amount of one or more of the above pharmaceutical compositions or vaccines.

In yet a further aspect, methods for the treatment of Chlamydia infection in a patient are provided, the methods comprising obtaining peripheral blood mononuclear cells (PBMC) from the patient, incubating the PBMC. with a polypeptide of the present invention (or a polynucleotide that encodes such a polypeptide) to provide incubated T cells and administering the incubated T cells to the patient. The present invention additionally provides methods for the treatment of Chlamydia infection that comprise incubating antigen presenting cells with a polypeptide of the present invention (or a polynucleotide that encodes such a polypeptide) to provide incubated antigen presenting cells and administering the incubated antigen presenting cells to the patient. In certain embodiments, the antigen presenting cells are selected from the group consisting of dendritic cells, macrophages, monocytes, B-cells, and fibroblasts. Compositions for the treatment of Chlamydia infection comprising T cells or antigen presenting cells that have been incubated with a polypeptide or polynucleotide of the present invention are also provided.

In further aspects of the subject invention, methods and diagnostic kits are provided for detecting Chlamydia infection in a patient. In one embodiment, the method comprises: (a) contacting a biological sample with at least one of the polypeptides or fusion proteins disclosed herein; and (b) detecting in the sample the presence of antibodies that bind to the polypeptide or fusion protein, thereby detecting Chlamydia infection in the biological sample. Suitable biological samples include whole blood, sputum, serum, plasma, saliva, cerebrospinal fluid and urine. In one embodiment, the diagnostic kits comprise one or more of the polypeptides or fusion proteins disclosed herein in combination with a detection reagent. In yet another embodiment, the diagnostic kits comprise either a monoclonal antibody or a polyclonal antibody that binds with a polypeptide of the present invention.

The present invention also provides methods for detecting Chlamydia infection comprising: (a) obtaining a biological sample from a patient; (b) contacting the sample with at least two oligonucleotide primers in a polymerase chain reaction, at least one of the oligonucleotide primers being specific for a polynucleotide sequence disclosed herein; and (c) detecting in the sample a polynucleotide sequence that amplifies in the presence of the oligonucleotide primers. In one embodiment, the oligonucleotide primer comprises at least about 10 contiguous nucleotides of a polynucleotide sequence peptide disclosed herein, or of a sequence that hybridizes thereto.

In a further aspect, the present invention provides a method for detecting Chlamydia infection in a patient comprising: (a) obtaining a biological sample from the patient; (b) contacting the sample with an oligonucleotide probe specific for a polynucleotide sequence disclosed herein; and (c) detecting in the sample a polynucleotide sequence that hybridizes to the oligonucleotide probe. In one embodiment, the oligonucleotide probe comprises at least about 15 contiguous nucleotides of a polynucleotide sequence disclosed herein, or a sequence that hybridizes thereto.

These and other aspects of the present invention will become apparent upon reference to the following detailed description. All references disclosed herein are hereby incorporated by reference in their entirety as if each was incorporated individually.

Sequence Identifiers

SEQ ID NO: 1 is the determined DNA sequence for the *C. trachomatis* clone 1-B1-66.

SEQ ID NO: 2 is the determined DNA sequence for the *C. trachomatis* clone 4-D7-28.

SEQ ID NO: 3 is the determined DNA sequence for the *C. trachomatis* clone 3-G3-10.

SEQ ID NO: 4 is the determined DNA sequence for the *C. trachomatis* clone 10-C10-31.

SEQ ID NO: 5 is the predicted amino acid sequence for 1-B1-66.

SEQ ID NO: 6 is the predicted amino acid sequence for 4-D7-28.

SEQ ID NO: 7 is a first predicted amino acid sequence for 3-G3-10.

SEQ ID NO: 8 is a second predicted amino acid sequence for 3-G3-10.

SEQ ID NO: 9 is a third predicted amino acid sequence for 3-G3-10.

SEQ ID NO: 10 is a fourth predicted amino acid sequence for 3-G3-10.

SEQ ID NO: 11 is a fifth predicted amino acid sequence for 3-G3-10.

SEQ ID NO: 12 is the predicted amino acid sequence for 10-C10-31.

SEQ ID NO: 13 is the amino acid sequence of the synthetic peptide 1-B1-66/48-67.

SEQ ID NO: 14 is the amino acid sequence of the synthetic peptide 1-B1-66/58-77.

SEQ ID NO: 15 is the determined DNA sequence for the *C. trachomatis* serovar LGV II clone 2C7-8

SEQ ID NO: 16 is the determined DNA sequence for a first putative open reading frame from *C. trachomatis* serovar D SEQ ID NO: 17 is the predicted amino acid sequence encoded by the first putative open reading frame from *C. trachomatis* serovar D SEQ ID NO: 18 is the amino acid sequence of the synthetic peptide CtC7.8-12

SEQ ID NO: 19 is the amino acid sequence of the synthetic peptide CtC7.8-13

SEQ ID NO: 20 is the predicted amino acid sequence encoded by a second putative open reading from *C. trachomatis* serovar D SEQ ID NO: 21 is the determined DNA sequence for clone 4C9-18 from *C. trachomatis* LGV II SEQ ID NO: 22 is the determined DNA sequence homologous to Lipoamide Dehydrogenase from *C. trachomatis* LGV II SEQ ID NO: 23 is the determined DNA sequence homologous to Hypothetical protein from *C. trachomatis* LGV II SEQ ID NO: 24 is the determined DNA sequence homologous to Ubiquinone Mehtyltransferase from *C. trachomatis* LGV II SEQ ID NO: 25 is the determined DNA sequence for clone 4C9-18#2 BL21 pLysS from *C. trachomatis* LGV II SEQ ID NO: 26 is the predicted amino acid sequence for 4C9-18#2 from *C. trachomatis* LGV II SEQ ID NO: 27 is the determined DNA sequence for Cp-SWIB from *C. pneumonia* strain TWAR SEQ ID NO: 28 is the predicted amino acid sequence for Cp-SWIB from *C. pneumonia* strain TWAR SEQ ID NO: 29 is the determined DNA sequence for Cp-S13 from *C. pneumonia* strain TWAR SEQ ID NO: 30 is the predicted amino acid sequence for Cp-S13 from *C. pneumonia* strain TWAR SEQ ID NO: 31 is the amino acid sequence for a 10 mer consensus peptide from CtC7.8-12 and CtC7.8-13

SEQ ID NO: 32 is the predicted amino acid sequence for clone 2C7-8 from *C. trachomatis* LGV II SEQ ID NO: 33 is the determined DNA sequence of a clone from *C. trachomatis* serovar D which shows homology to clone 2C7-8

SEQ ID NO: 34 is the predicted amino acid sequence encoded by the sequence of SEQ ID NO: 33

SEQ ID NO: 35 is the DNA sequence for C.p. SWIB Nde (5' primer) from *C. pneumonia*

SEQ ID NO: 36 is the DNA sequence for C.p. SWIB EcoRI (3' primer) from *C. pneumonia*

SEQ ID NO: 37 is the DNA sequence for C.p. S13 Nde (5' primer) from *C. pneumonia*

SEQ ID NO: 38 is the DNA sequence for C.p. S13 EcoRI (3' primer) from *C. pneumonia*

SEQ ID NO: 39 is the amino acid sequence for CtSwib 52–67 peptide from *C. trachomatis* LGV II SEQ ID NO: 40 is the amino acid sequence for CpSwib 53–68 peptide from *C. pneumonia*

SEQ ID NO: 41 is the amino acid sequence for HuSwib 288–302 peptide from Human SWI domain SEQ ID NO: 42 is the amino acid sequence for CtSWI-T 822–837 peptide from the topoisomerase-SWIB fusion of *C. trachomatis*

SEQ ID NO: 43 is the amino acid sequence for CpSWI-T 828–842 peptide from the topoisomerase-SWIB fusion of *C. pneumonia*

SEQ ID NO: 44 is a first determined DNA sequence for the *C. trachomatis* LGV II clone 19783.3,jen.seq (1>509)CTL2#11-3', representing the 3' end.

SEQ ID NO: 45 is a second determined DNA sequence for the *C. trachomatis* LGV II clone 19783.4,jen.seq (1>481)CTL2#11-5', representing the 5' end.

SEQ ID NO: 46 is the determined DNA sequence for the *C. trachomatis* LGV II clone 19784CTL2_12consensus.seq(1>427)CTL2#12.

SEQ ID NO: 47 is the determined DNA sequence for the *C. trachomatis* LGV II clone 19785.4,jen.seq(1>600) CTL2#16-5', representing the 5' end.

SEQ ID NO: 48 is a first determined DNA sequence for the *C. trachomatis* LGV II clone 19786.3,jen.seq (1>600)CTL2#18-3', representing the 3' end.

SEQ ID NO: 49 is a second determined DNA sequence for the *C. trachomatis* LGV II clone 19786.4,jen.seq (1>600)CTL2#18-5', representing the 5' end.

SEQ ID NO: 50 is the determined DNA sequence for the *C. trachomatis* LGV II clone 19788CTL2_21consensus.seq(1>406)CTL2#21.

SEQ ID NO: 51 is the determined DNA sequence for the *C. trachomatis* LGV II clone 19790CTL2_23consensus.seq(1>602)CTL2#23.

SEQ ID NO: 52 is the determined DNA sequence for the *C. trachomatis* LGV II clone 19791CTL2_24consensus.seq(1>145)CTL2#24.

SEQ ID NO: 53 is the determined DNA sequence for the *C. trachomatis* LGV II clone CTL2#4.

SEQ ID NO: 54 is the determined DNA sequence for the *C. trachomatis* LGV II clone CTL2#8b.

SEQ ID NO: 55 is the determined DNA sequence for the *C. trachomatis* LGV II clone 15-G1-89, sharing homology to the lipoamide dehydrogenase gene CT557.

SEQ ID NO: 56 is the determined DNA sequence for the *C. trachomatis* LGV II clone 14-H1-4, sharing homology to the thiol specific antioxidant gene CT603.

SEQ ID NO: 57 is the determined DNA sequence for the *C. trachomatis* LGV II clone 12-G3-83, sharing homology to the hypothetical protein CT622.

SEQ ID NO: 58 is the determined DNA sequence for the *C. trachomatis* LGV II clone 12-B3-95, sharing homology to the lipoamide dehydrogenase gene CT557.

SEQ ID NO: 59 is the determined DNA sequence for the *C. trachomatis* LGV II clone 11-H4-28, sharing homology to the dnaK gene CT396.

SEQ ID NO: 60 is the determined DNA sequence for the *C. trachomatis* LGV II clone 11-H3-68, sharing partial homology to the PGP6-D virulence protein and L1 ribosomal gene CT318.

SEQ ID NO: 61 is the determined DNA sequence for the *C. trachomatis* LGV II clone 11-G1-34, sharing partial homology to the malate dehydrogenase gene CT376 and to the glycogen hydrolase gene CT042.

SEQ ID NO: 62 is the determined DNA sequence for the *C. trachomatis* LGV II clone 11-G10-46, sharing homology to the hypothetical protein CT610.

SEQ ID NO: 63 is the determined DNA sequence for the *C. trachomatis* LGV II clone 11-C12-91, sharing homology to the OMP2 gene CT443.

SEQ ID NO: 64 is the determined DNA sequence for the *C. trachomatis* LGV II clone 11-A3-93, sharing homology to the HAD superfamily gene CT103.

SEQ ID NO: 65 is the determined amino acid sequence for the *C. trachomatis* LGV II clone 14-H1-4, sharing homology to the thiol specific antioxidant gene CT603.

SEQ ID NO: 66 is the determined DNA sequence for the *C. trachomatis* LGV II clone CtL2#9.

SEQ ID NO: 67 is the determined DNA sequence for the *C. trachomatis* LGV II clone CtL2#7.

SEQ ID NO: 68 is the determined DNA sequence for the *C. trachomatis* LGV II clone CtL2#6.

SEQ ID NO: 69 is the determined DNA sequence for the *C. trachomatis* LGV II clone CtL2#5.

SEQ ID NO: 70 is the determined DNA sequence for the *C. trachomatis* LGV II clone CtL2#2.

SEQ ID NO: 71 is the determined DNA sequence for the *C. trachomatis* LGV II clone CtL2#1.

SEQ ID NO: 72 is a first determined DNA sequence for the *C. trachomatis* LGV II clone 23509.2CtL2#3-5', representing the 5' end.

SEQ ID NO: 73 is a second determined DNA sequence for the *C. trachomatis* LGV II clone 23509.1CtL2#3-3', representing the 3' end.

SEQ ID NO: 74 is a first determined DNA sequence for the *C. trachomatis* LGV II clone 22121.2CtL2#10-5', representing the 5' end.

SEQ ID NO: 75 is a second determined DNA sequence for the *C. trachomatis* LGV II clone 22121.1CtL2#10-3', representing the 3' end.

SEQ ID NO: 76 is the determined DNA sequence for the *C. trachomatis* LGV II clone 19787.6CtL2#19-5', representing the 5' end.

SEQ ID NO: 77 is the determined DNA sequence for the *C. pneumoniae* LGV II clone CpS13-His.

SEQ ID NO: 78 is the determined DNA sequence for the *C. pneumoniae* LGV II clone Cp_SWIB-His.

SEQ ID NO: 79 is the determined DNA sequence for the *C. trachomatis* LGV II clone 23-G7-68, sharing partial homology to the L11, L10 and L1 ribosomal protein.

SEQ ID NO: 80 is the determined DNA sequence for the *C. trachomatis* LGV II clone 22-F8-91, sharing homology to the pmpC gene.

SEQ ID NO: 81 is the determined DNA sequence for the *C. trachomatis* LGV II clone 21-E8-95, sharing homology to the CT610-CT613 genes.

SEQ ID NO: 82 is the determined DNA sequence for the *C. trachomatis* LGV II clone 19-F12-57, sharing homology to the CT858 and recA genes.

SEQ ID NO: 83 is the determined DNA sequence for the *C. trachomatis* LGV II clone 19-F12-53, sharing homology to the CT445 gene encoding glutamyl tRNA synthetase.

SEQ ID NO: 84 is the determined DNA sequence for the *C. trachomatis* LGV II clone 19-A5-54, sharing homology to the cryptic plasmid gene.

SEQ ID NO: 85 is the determined DNA sequence for the *C. trachomatis* LGV II clone 17-E11-72, sharing partial homology to the OppC_2 and pmpD genes.

SEQ ID NO: 86 is the determined DNA sequence for the *C. trachomatis* LGV II clone 17-C1-77, sharing partial homology to the CT857 and CT858 open reading frames.

SEQ ID NO: 87 is the determined DNA sequence for the *C. trachomatis* LGV II clone 15-H2-76, sharing partial homology to the pmpD and SycE genes, and to the CT089 ORF.

SEQ ID NO: 88 is the determined DNA sequence for the *C. trachomatis* LGV II clone 15-A3-26, sharing homology to the CT858 ORF.

SEQ ID NO: 89 is the determined amino acid sequence for the *C. pneumoniae* clone Cp_SWIB-His.

SEQ ID NO: 90 is the determined amino acid sequence for the *C. trachomatis* LGV II clone CtL2_LPDA_FL.

SEQ ID NO: 91 is the determined amino acid sequence for the *C. pnuemoniae* clone CpS13-His.

SEQ ID NO: 92 is the determined amino acid sequence for the *C. trachomatis* LGV II clone CtL2_TSA_FL.

SEQ ID NO: 93 is the amino acid sequence for Ct-Swib 43–61 peptide from *C. trachomatis* LGV II.

SEQ ID NO: 94 is the amino acid sequence for Ct-Swib 48–67 peptide from *C. trachomatis* LGV II.

SEQ ID NO: 95 is the amino acid sequence for Ct-Swib 52–71 peptide from *C. trachomatis* LGV II.

SEQ ID NO: 96 is the amino acid sequence for Ct-Swib 58–77 peptide from *C. trachomatis* LGV II.

SEQ ID NO: 97 is the amino acid sequence for Ct-Swib 63–82 peptide from *C. trachomatis* LGV II.

SEQ ID NO: 98 is the amino acid sequence for Ct-Swib 51–66 peptide from *C. trachomatis* LGV II.

SEQ ID NO: 99 is the amino acid sequence for Cp-Swib 52–67 peptide from *C. pneumonia*.

SEQ ID NO: 100 is the amino acid sequence for Cp-Swib 37–51 peptide from *C. pneumonia*.

SEQ ID NO: 101 is the amino acid sequence for Cp-Swib 32–51 peptide from *C. pneumonia*.

SEQ ID NO: 102 is the amino acid sequence for Cp-Swib 37–56 peptide from *C. pneumonia*.

SEQ ID NO: 103 is the amino acid sequence for Ct-Swib 36–50 peptide from *C. trachomatis*.

SEQ ID NO: 104 is the amino acid sequence for Ct-S13 46–65 peptide from *C. trachomatis*.

SEQ ID NO: 105 is the amino acid sequence for Ct-S13 60–80 peptide from *C. trachomatis*.

SEQ ID NO: 106 is the amino acid sequence for Ct-S13 1–20 peptide from *C. trachomatis*.

SEQ ID NO: 107 is the amino acid sequence for Ct-S13 46–65 peptide from *C. trachomatis*.

SEQ ID NO: 108 is the amino acid sequence for Ct-S13 56;75 peptide from *C. trachomatis*.

SEQ ID NO: 109 is the amino acid sequence for Cp-S13 56–75 peptide from *C. pneumoniae*.

DESCRIPTION OF THE FIGURES

FIG. 6 illustrates the 5' and 3' primer sequences designed from *C. pneumoniae* which were used to isolate the SWIB and S13 genes from *C. pneumoniae*.

FIG. 8 shows the identification of T cell epitopes in Chlamydial ribosomal S13 protein with T-cell line TCL 8 EB/DC.

FIG. 9 illustrates the proliferative response of CP-21 T-cells generated against *C. pnuemoniae*-infected dendritic cells to recombinant *C. pneumonia*-SWIBprotein, but not *C. trachomatis* SWIB protein.

FIG. 10 shows the *C. trachomatis*-specific SWIB proliferative responses of a primary T-cell line (TCT-10 EB) from an asymptomatic donor.

FIG. 11 illustrates the identification of T-cell epitope in *C. trachomatis* SWIB with an antigen specific T-cell line (TCL-10 EB).

DETAILED DESCRIPTION OF THE INVENTION

Figure 1:
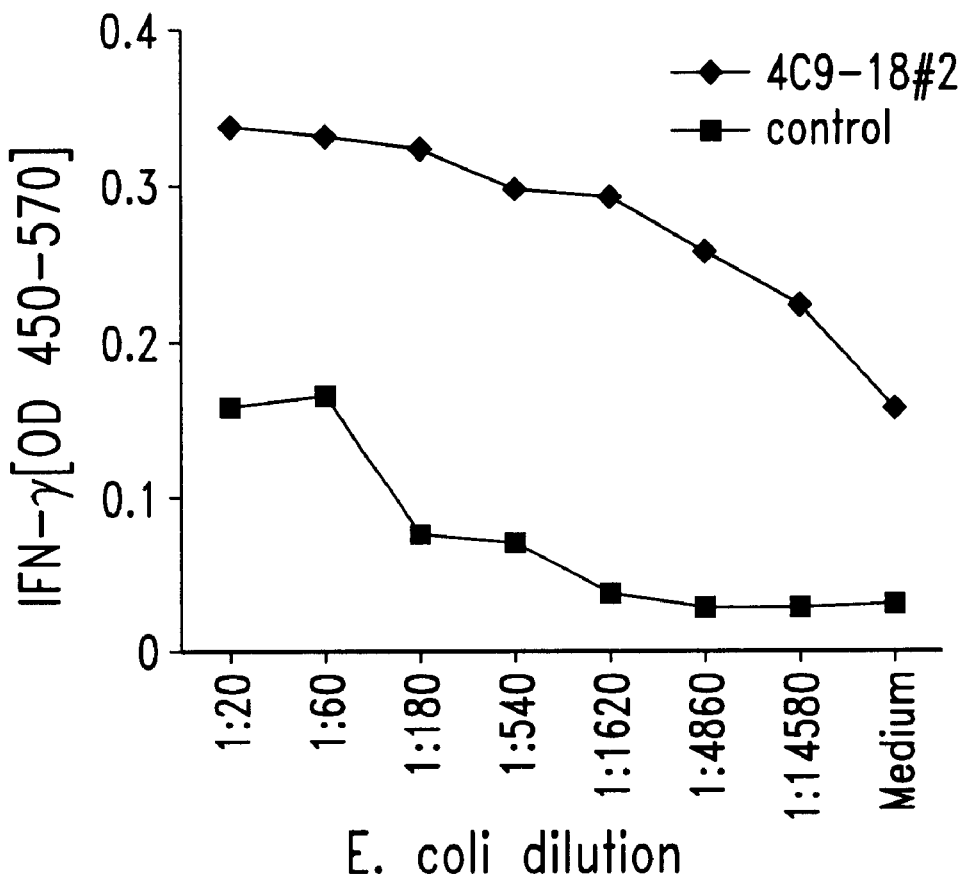
FIG. 1 illustrates induction of INF-γ from a Chlamydia-specific T cell line activated by target cells expressing clone 4C9-18#2.

As noted above, the present invention is generally directed to compositions and methods for the diagnosis and treatment of Chlamydial infection. In one aspect, the compositions of the subject invention include polypeptides that comprise at least one immunogenic portion of a Chlamydia antigen, or a variant thereof.

In specific embodiments, the subject invention discloses polypeptides comprising an immunogenic portion of a Chlamydia antigen, wherein the Chlamydia antigen comprises an amino acid sequence encoded by a polynucleotide molecule including a sequence selected from the group consisting of (a) nucleotide sequences recited in SEQ ID NO: 1–4, 15, 21–25, 44–64, 66–76 and 79–88 (b) the complements of said nucleotide sequences, and (c) variants of such sequences.

As used herein, the term "polypeptide" encompasses amino acid chains of any length, including full length proteins (i.e., antigens), wherein the amino acid residues are linked by covalent peptide bonds. Thus, a polypeptide comprising an immunogenic portion of one of the inventive antigens may consist entirely of the immunogenic portion, or may contain additional sequences. The additional sequences may be derived from the native Chlamydia antigen or may be heterologous, and such sequences may (but need not) be immunogenic.

The term "polynucleotide(s)," as used herein, means a single or double-stranded polymer of deoxyribonucleotide or ribonucleotide bases and includes DNA and corresponding RNA molecules, including HnRNA and mRNA molecules, both sense and anti-sense strands, and comprehends cDNA, genomic DNA and recombinant DNA, as well as wholly or partially synthesized polynucleotides. An HnRNA molecule contains introns and corresponds to a DNA molecule in a generally one-to-one manner. An mRNA molecule corresponds to an HnRNA and DNA molecule from which the introns have been excised. A polynucleotide may consist of an entire gene, or any portion thereof. Operable anti-sense polynucleotides may comprise a fragment of the corresponding polynucleotide, and the definition of "polynucleotide" therefore includes all such operable anti-sense fragments.

An "immunogenic portion" of an antigen is a portion that is capable of reacting with sera obtained from a Chlamydia-infected individual (i.e., generates an absorbance reading with sera from infected individuals that is at least three standard deviations above the absorbance obtained with sera from uninfected individuals, in a representative ELISA assay described herein). Such immunogenic portions generally comprise at least about 5 amino acid residues, more preferably at least about 10, and most preferably at least about 20 amino acid residues. Methods for preparing and identifying immunogenic portions of antigens of known sequence are well known in the art and include those summarized in Paul, *Fundamental Immunology*, 3$^{rd}$ ed., Raven Press, 1993, pp. 243–247. Examples of immunogenic portions of antigens contemplated by the present invention include, for example, the T cell stimulating epitopes provided in SEQ ID NO: 9, 10, 18, 19, 31 and 39. Polypeptides comprising at least an immunogenic portion of one or more Chlamydia antigens as described herein may generally be used, alone or in combination, to detect Chlamydial infection in a patient.

The compositions and methods of the present invention also encompass variants of the above polypeptides and polynucleotide molecules. Such variants include, but are not limited to, naturally occurring allelic variants of the inventive sequences. In particular, variants include other Chlamydiae serovars, such as serovars D, E and F, as well as the several LGV serovars which share homology to the inventive polypeptide and polynucleotide molecules described herein. Preferably, the serovar homologues show 95–99% homology to the corresponding polypeptide sequence(s) described herein.

A polypeptide "variant," as used herein, is a polypeptide that differs from the recited polypeptide only in conservative substitutions and/or modifications, such that the antigenic properties of the polypeptide are retained. In a preferred embodiment, variant polypeptides differ from an identified sequence by substitution, deletion or addition of five amino acids or fewer. Such variants may generally be identified by modifying one of the above polypeptide sequences, and evaluating the antigenic properties of the modified polypeptide using, for example, the representative procedures described herein. Polypeptide variants preferably exhibit at least about 70%, more preferably at least about 90% and most preferably at least about 95% identity (determined as described below) to the identified polypeptides.

As used herein, a "conservative substitution" is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (I) ala, pro, gly, glu, asp, gin, asn, ser, thr; (2) cys, ser, tyr, thr; (3) val, ile, leu, met, ala, phe; (4) lys, arg, his; and (5) phe, tyr, trp, his.

Variants may also, or alternatively, contain other modifications, including the deletion or addition of amino acids that have minimal influence on the antigenic properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

A nucleotide "variant" is a sequence that differs from the recited nucteotide sequence in having one or more nucleotide deletions, substitutions or additions. Such modifications may be readily introduced using standard mutagenesis techniques, such as oligonucleotide-directed site-specific mutagenesis as taught, for example, by Adelman et al. (*DNA*, 2:183, 1983). Nucleotide variants may be naturally occurring allelic variants as discussed below, or non-naturally occurring variants. Variant nucleotide sequences preferably exhibit at least about 70%, more preferably at least about 80% and most preferably at least about 90% identity (determined as described below) to the recited sequence.

The polypeptides provided by the present invention include variants that are encoded by polynucleotide sequences which are substantially homologous to one or more of the polynucleotide sequences specifically recited herein. "Substantial homology," as used herein, refers to polynucleotide sequences that are capable of hybridizing under moderately stringent conditions. Suitable moderately stringent conditions include prewashing in a solution of 5×SSC, 0.5%/ SDS, 1.0 mM EDTA (pH 8.0); hybridizing at 50° C.–65° C. 5×SSC, overnight or, in the event of cross-species homology, at 45° C. with 0.5×SSC; followed by washing twice at 65° C. for 20 minutes with each of 2×, 0.5× and 0.2×SSC containing 0.1% SDS. Such hybridizing polynucleotide sequences are also within the scope of this invention, as are nucleotide sequences that, due to code degeneracy, encode a polypeptide that is the same as a polypeptide of the present invention.

Two nucleotide or polypeptide sequences are said to be "identical" if the sequence of nucleotides or amino acid residues in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment. schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Resarch Foundaiton, Washington D.C. Vol. 5, Suppl. 3, pp. 345–358; Hein J. (1990) Unified Approach to Alignment and Phylogenes pp. 626–645 *Methods in Enzymology* vol. 183, Academic Press, Inc., San Diego, Calif.; Higgins, D. G. and Sharp, P. M. (1989) Fast and sensitive multiple sequence alignments on a microcomputer *CABIOS* 5:151–153; Myers, E. W. and Muller W. (1988) Optimal alignments in linear space *CABIOS* 4:11–17; Robinson, E. D. (1971) *Comb. Theor* 11:105; Santou, N. Nes, M. (1987) The neighbor joining method. A new method for reconstructing phylogenetic trees *Mol. Biol. Evol.* 4:406–425; Sneath, P. H. A. and Sokal, R. R. (1973) *Numerical Taxonomy—the Principles and Practice of Numerical Taxonomy,* Freeman Press, San Francisco, Calif.; Wilbur, W. J. and Lipman, D. J. (1983) Rapid similarity searches of nucleic acid and protein data banks *Proc. Natl. Acad., Sci. USA* 80:726–730.

Preferably, the "percentage of sequence identity" is determined by comparing two optimally aligned sequences over a window of comparison of at least 20 positions, wherein the portion of the polynucleotide sequence in the comparison window may comprise additions or deletions (i.e. gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Also included in the scope of the present invention are alleles of the genes encoding the nucleotide sequences recited in herein. As used herein, an "allele" or "allellic sequence" is an alternative form of the gene which may result from at least one mutation in the nucleic acid sequence. Alleles may result in altered mRNAs or polypeptides whose structure or function may or may not be altered. Any given gene may have none, one, or many allelic forms. Common mutational changes which give rise to alleles are generally ascribed to natural deletions, additions, or substitutions of nucleotides. Each of these types of changes may occur alone or in combination with the others, one or more times in a given sequence. In specific embodiments, the subject invention discloses polypeptides comprising at least an immunogenic portion of a Chlamydia antigen (or a variant of such an antigen), that comprises one or more of the amino acid sequences encoded by (a) a polynucleotide sequence selected from the group consisting of SEQ ID NO: 1–4, 15 21–25, 44–64, 66–76 and 79–88; (b) the complements of such DNA sequences or (c) DNA sequences substantially homologous to a sequence in (a) or (b). As discussed in the Examples below, several of the Chlamydia antigens disclosed herein recognize a T cell line that recognizes both *Chlamydia trachomatis* and *Chlamydia pneumoniae* infected monocyte-derived dendritic cells, indicating that they may represent an immunoreactive epitope shared by *Chlamydia trachomatis* and *Chlamydia pneumoniae*. The antigens may thus be employed in a vaccine for both *C. trachomatis* genital tract infections and for *C. pneumonia* infections. Further characterization of these Chlamydia antigens from *Chlamydia trachomatis* and *Chlamydia pneumonia* to determine the extent of cross-reactivity is provided in Example 6. Additionally, Example 4 describes cDNA fragments (SEQ ID NO: 15, 16 and 33) isolated from *C. trachomatis* which encode proteins (SEQ ID NO: 17–19 and 32) capable of stimulating a Chlamydia-specific murine CD8+ T cell line.

In general, Chlamydia antigens, and polynucleotide sequences encoding such antigens, may be prepared using any of a variety of procedures. For example, polynucleotide molecules encoding Chlamydia antigens may be isolated from a Chlamydia genomic or cDNA expression library by screening with a Chlamydia-specific T cell line as described below, and sequenced using techniques well known to those of skill in the art. Antigens may be produced recombinantly, as described below, by inserting a polynucleotide sequence that encodes the antigen into an expression vector and expressing the antigen in an appropriate host. Antigens may be evaluated for a desired property, such as the ability to react with sera obtained from a Chlamydia-infected individual as described herein, and may be sequenced using, for example, traditional Edman chemistry. See Edman and Berg, *Eur. J. Biochem.* 80:116–132, 1967.

Polynucleotide sequences encoding antigens may also be obtained by screening an appropriate Chlamydia cDNA or genomic DNA library for polynucleotide sequences that hybridize to degenerate oligonucleotides derived from partial amino acid sequences of isolated antigens. Degenerate oligonucleotide sequences for use in such a screen may be designed and synthesized, and the screen may be performed, as described (for example) in Sambrook et al., *Molecular Cloning: A Laboratory Manual,* Cold Spring Harbor Laboratories, Cold Spring Harbor, N.Y. (and references cited therein). Polymerase chain reaction (PCR) may also be employed, using the above oligonucleotides in methods welt known in the art, to isolate a nucleic acid probe from a cDNA or genomic library. The library screen may then be performed using the isolated probe.

An amplified portion may be used to isolate a full length gene from a suitable library (e.g., a Chlamydia cDNA library) using well known techniques. Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences.

For hybridization techniques, a partial sequence may be labeled (e.g., by nick-translation or end-labeling with $^{32}$P) using well known techniques. A bacterial or bacteriophage library is then screened by hybridizing filters containing denatured bacterial colonies (or lawns containing phage plaques) with the labeled probe (see Sambrook et al., *Molecular Cloning: A Laboratory Manual,* Cold Spring Harbor Laboratories, Cold Spring Harbor, N.Y., 1989). Hybridizing colonies or plaques are selected and expanded, and the DNA is isolated for further analysis. cDNA clones may be analyzed to determine the amount of additional sequence by, for example, PCR using a primer from the partial sequence and a primer from the vector. Restriction maps and partial sequences may be generated to identify one or more overlapping clones. The complete sequence may then be determined using standard techniques which may involve generating a series of deletion clones. The resulting overlapping sequences are then assembled into a single contiguous sequence. A full length cDNA molecule can be generated by ligating suitable fragments, using well known techniques.

Alternatively, there are numerous amplification techniques for obtaining a full length coding sequence from a partial cDNA sequence. Within such techniques, amplification is generally performed via PCR. Any of a variety of commercially available kits may be used to perform the amplification step. Primers may be designed using techniques well known in the art (see, for example, Mullis et al., *Cold Spring Harbor Symp. Quant. Biol.* 51:263, 1987, Erlich ed., *PCR Technology,* Stockton Press, NY, 1989), and software well known in the art may also be employed. Primers are preferably 22–30 nucleotides in length, have a GC content of at least 50% and anneal to the target sequence at temperatures of about 68° C. to 72° C. The amplified region may be sequenced as described above, and overlapping sequences assembled into a contiguous sequence.

One such amplification technique is inverse PCR (see Triglia et al., *Nucl. Acids Res.* 16:8186, 1988), which uses restriction enzymes to generate a fragment in the known region of the gene. The fragment is then circularized by intramolecular ligation and used as a template for PCR with divergent primers derived from the known region. Within an alternative approach, sequences adjacent to a partial sequence may be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in WO 96/38591. Additional techniques include capture PCR (Lagerstrom et al., *PCR Methods Applic.* 1:111–19, 1991) and walking PCR (Parker et al., *Nucl. Acids. Res.* 19:3055–60, 1991). Transcription-Mediated Amplification, or TMA is another method that may be utilized for the amplification of DNA, rRNA, or mRNA, as described in Patent No. PCT/US91/03184. This autocatalytic and isothermic non-PCR based method utilizes two primers and two enzymes: RNA polymerase and reverse transcriptase. One primer contains a promoter sequence for RNA polymerase. In the first amplification, the promoter-primer hybridizes to the target rRNA at a defined site. Reverse transcriptase creates a DNA copy of the target rRNA by extension from the 3'end of the promoter-primer. The RNA in the resulting complex is degraded and a second primer binds to the DNA copy. A new strand of DNA is synthesized from the end of the primer by reverse transcriptase creating double stranded DNA. RNA polymerase recognizes the promoter sequence in the DNA template and initiates transcription. Each of the newly synthesized RNA amplicons re-enters the TMA process and serves as a template for a new round of replication leading to the expotential expansion of the RNA amplicon. Other methods employing amplification may also be employed to obtain a full length cDNA sequence.

In certain instances, it is possible to obtain a full length cDNA sequence by analysis of sequences provided in an expressed sequence tag (EST) database, such as that available from GenBank. Searches for overlapping ESTs may generally be performed using well known programs (e.g., NCBI BLAST searches), and such ESTs may be used to generate a contiguous full length sequence.

Synthetic polypeptides having fewer than about 100 amino acids, and generally fewer than about 50 amino acids, may be generated using techniques well known in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Perkin Elmer/Applied BioSystems Division, Foster City, Calif., and may be operated according to the manufacturer's instructions.

As noted above, immunogenic portions of Chlamydia antigens may be prepared and identified using well known techniques, such as those summarized in Paul, *Fundamental Immunology,* 3d ed., Raven Press, 1993, pp. 243–247 and references cited therein. Such techniques include screening polypeptide portions of the native antigen for immunogenic properties. The representative ELISAs described herein may generally be employed in these screens. An immunogenic portion of a polypeptide is a portion that, within such representative assays, generates a signal in such assays that is substantially similar to that generated by the full length antigen. In other words, an immunogenic portion of a Chlamydia antigen generates at least about 20%, and preferably about 100%, of the signal induced by the full length antigen in a model ELISA as described herein.

Portions and other variants of Chlamydia antigens may be generated by synthetic or recombinant means. Variants of a native antigen may generally be prepared using standard mutagenesis techniques, such as oligonucleotide-directed site-specific mutagenesis. Sections of the polynucleotide sequence may also be removed using standard techniques to permit preparation of truncated polypeptides.

Recombinant polypeptides containing portions and/or variants of a native antigen may be readily prepared from a polynucleotide sequence encoding the polypeptide using a variety of techniques well known to those of ordinary skill in the art. For example, supernatants from suitable host/vector systems which secrete recombinant protein into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant protein.

Any of a variety of expression vectors known to those of ordinary skill in the art may be employed to express recombinant polypeptides as described herein. Expression may be achieved in any appropriate host cell that has been transformed or transfected with an expression vector containing a polynucleotide molecule that encodes a recombinant polypeptide. Suitable host cells include prokaryotes, yeast and higher eukaryotic cells. Preferably, the host cells employed are *E. coli,* yeast or a mammalian cell line, such as COS or CHO. The DNA sequences expressed in this manner may encode naturally occurring antigens, portions of naturally occurring antigens, or other variants thereof.

In general, regardless of the method of preparation, the polypeptides disclosed herein are prepared in an isolated, substantially pure, form. Preferably, the polypeptides are at least about 80% pure more preferably at least about 90% pure and most preferably at least about 99% pure.

In a further aspect, the present invention provides fusion proteins comprising either a first and a second inventive polypeptide, or an inventive polypeptide and a known Chlamydia antigen, together with variants of such fusion proteins. The fusion proteins of the present invention may include a linker peptide between the polypeptides.

A DNA sequence encoding a fusion protein of the present invention may be constructed using known recombinant DNA techniques to assemble separate DNA sequences encoding, for example, the first and second polypeptides, into an appropriate expression vector. The 3' end of a DNA sequence encoding the first polypeptide is ligated, with or without a peptide linker, to the 5' end of a DNA sequence encoding the second polypeptide so that the reading frames of the sequences are in phase to permit mRNA translation of the two DNA sequences into a single fusion protein that retains the biological activity of both the first and the second polypeptides.

A peptide linker sequence may be employed to separate the first and the second polypeptides by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation, (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci. USA* 83:8258–8562, 1986; U.S. Pat. Nos. 4,935,233 and 4,751,180. The linker sequence may be from 1 to about 50 amino acids in length. As an alternative to the use of a peptide linker sequence (when desired), one can utilize non-essential N-terminal amino acid regions (when present) on the first and second polypeptides to separate the functional domains and prevent steric hindrance.

In another aspect, the present invention provides methods for using one or more of the above polypeptides or fusion proteins (or polynucleotides encoding such polypeptides or fusion proteins) to induce protective immunity against Chlamydial infection in a patient. As used herein, a "patient" refers to any warm-blooded animal, preferably a human. A patient may be afflicted with a disease, or may be free of detectable disease and/or infection. In other words, protective immunity may be induced to prevent or treat Chlamydial infection.

In this aspect, the polypeptide, fusion protein or polynucleotide molecule is generally present within a pharmaceutical composition or a vaccine. Pharmaceutical compositions may comprise one or more polypeptides, each of which may contain one or more of the above sequences (or variants thereof), and a physiologically acceptable carrier. Vaccines may comprise one or more of the above polypeptides and a non-specific immune response enhancer, such as an adjuvant or a liposome (into which the polypeptide is incorporated). Such pharmaceutical compositions and vaccines may also contain other Chlamydia antigens, either incorporated into a combination polypeptide or present within a separate polypeptide.

Alternatively, a vaccine mav contain polynucleotides encoding one or more polypeptides or fusion proteins as described above, such that the polypeptide is generated in situ. In such vaccines, the polynucleotides may be present within any of a variety of delivery systems known to those of ordinary skill in the art, including nucleic acid expression systems, bacterial and viral expression systems. Appropriate nucleic acid expression systems contain the necessary polynucleotide sequences for expression in the patient (such as a suitable promoter and terminating signal). Bacterial delivery systems involve the administration of a bacterium (such as Bacillus-Calmette-Guerrin) that expresses an immunogenic portion of the polypeptide on its cell surface. In a preferred embodiment, the polynucleotides may be introduced using a viral expression system (e.g., vaccinia or other pox virus, retrovirus, or adenovirus), which may involve the use of a non-pathogenic (defective) virus. Techniques for incorporating polynucleotides into such expression systems are well known to those of ordinary skill in the art. The polynucleotides may also be "naked," as described, for example, in Ulmer et al., *Science* 259:1745–1749, 1993 and reviewed by Cohen, *Science* 259:1691–1692, 1993. The uptake of naked polynucleotides may be increased by coating the polynucleotides onto biodegradable beads, which are efficiently transported into the cells.

In a related aspect, a polynucleotide vaccine as described above may be administered simultaneously with or sequentially to either a polypeptide of the present invention or a known Chlamydia antigen. For example, administration of polynucleotides encoding a polypeptide of the present invention, either "naked" or in a delivery system as described above, may be followed by administration of an antigen in order to enhance the protective immune effect of the vaccine.

Polypeptides and polynucleotides disclosed herein may also be employed in adoptive immunotherapy for the treatment of Chlamydial infection. Adoptive immunotherapy may be broadly classified into either active or passive immunotherapy. In active immunotherapy, treatment relies on the in vivo stimulation of the endogenous host immune system with the administration of immune response-modifying agents (for example, vaccines, bacterial adjuvants, and/or cytokines).

In passive immunotherapy, treatment involves the delivery of biologic reagents with established immune reactivity (such as effector cells or antibodies) that can directly or indirectly mediate anti-Chlamydia effects and does not necessarily depend on an intact host immune system. Examples of effector cells include T lymphocytes (for example, CD8+ cytotoxic T-lymphocyte, CD4+ T-helper, tumor-infiltrating lymphocytes), killer cells (such as Natural Killer cells, lymphokine-activated-killer cells), B cells, or antigen presenting cells (such as dendritic cells and macrophages) expressing the disclosed antigens. The polypeptides disclosed herein may also be used to generate antibodies or anti-idiotypic antibodies (as in U.S. Pat. No. 4,918,164), for passive immunotherapy.

The predominant method of procuring adequate numbers of T-cells for adoptive immunotherapy is to grow immune T-cells in vitro. Culture conditions for expanding single antigen-specific T-cells to several billion in number with retention of antigen recognition in vivo are well known in the art. These in vitro culture conditions typically utilize intermittent stimulation with antigen, often in the presence of cytokines, such as IL-2, and non-dividing feeder cells. As noted above, the immunoreactive polypeptides described herein may be used to rapidly expand antigen-specific T cell cultures in order to generate sufficient number of cells for immunotherapy. In particular, antigen-presenting cells, such as dendritic, macrophage, monocyte, fibroblast, or B-cells, may be pulsed with immunoreactive polypeptides, or polynucleotide sequence(s) may be introduced into antigen presenting cells, using a variety of standard techniques well known in the art. For example, antigen presenting cells may be transfected or transduced with a polynucleotide sequence, wherein said sequence contains a promoter region appropriate for increasing expression, and can be expressed as part of a recombinant virus or other expression system. Several viral vectors may be used to transduce an antigen presenting cell, including pox virus, vaccinia virus, and adenovirus; also, antigen presenting cells may be transfected with polynucleotide sequences disclosed herein by a variety of means, including gene-gun technology, lipid-mediated delivery, electroporation, osmotic shock, and particulate delivery mechanisms, resulting in efficient and acceptable expression levels as determined by one of ordinary skill in the art. For cultured T-cells to be effective in therapy, the cultured T-cells must be able to grow and distribute widely and to survive long term in vivo. Studies have demonstrated that cultured T-cells can be induced to grow in vivo and to survive long term in substantial numbers by repeated stimulation with antigen supplemented with IL-2 (see, for example, Cheever, M., et al, "Therapy With Cultured T Cells: Principles Revisited," *Immunological Reviews*, 157:177, 1997).

The polypeptides disclosed herein may also be employed to generate and/or isolate chlamydial-reactive T-cells, which can then be administered to the patient. In one technique, antigen-specific T-cell lines may be generated by in vivo immunization with short peptides corresponding to immunogenic portions of the disclosed polypeptides. The resulting antigen specific CD8+ or CD4+ T-cell clones may be isolated from the patient, expanded using standard tissue culture techniques, and returned to the patient.

Alternatively, peptides corresponding to immunogenic portions of the polypeptides may be employed to generate chlamydia reactive T cell subsets by selective in vitro stimulation and expansion of autologous T cells to provide antigen-specific T cells which may be subsequently transferred to the patient as described, for example, by Chang et al, (*Crit. Rev. Oncol. Hematol.*, 22(3), 213, 1996). Cells of the immune system, such as T cells, may be isolated from the peripheral blood of a patient, using a commercially available cell separation system, such as Isolex™ System, available from Nexell Therapeutics, Inc. Irvine, Calif. The separated cells are stimulated with one or more of the immunoreactive polypeptides contained within a delivery vehicle, such as a microsphere, to provide antigen-specific T cells. The population of antigen-specific T cells is then expanded using standard techniques and the cells are administered back to the patient.

In other embodiments, T-cell and/or antibody receptors specific for the polypeptides disclosed herein can be cloned, expanded, and transferred into other vectors or effector cells for use in adoptive immunotherapy. In particular, T cells may be transfected with the appropriate genes to express the variable domains from chlamydia specific monoclonal antibodies as the extracellular recognition elements and joined to the T cell receptor signaling chains, resulting in T cell activation, specific lysis, and cytokine release. This enables the T cell to redirect its specificity in an MHC-independent manner. See for example, Eshhar, Z., *Cancer Immunol Immunother,* 45(3-4):131–6, 1997 and Hwu, P., et al, *Cancer Res,* 55(15):3369–73, 1995. Another embodiment may include the transfection of chlamydia antigen specific alpha and beta T cell receptor chains into alternate T cells, as in Cole, D J, et al, *Cancer Res,* 55(4):748–52, 1995.

In a further embodiment, syngeneic or autologous dendritic cells may be pulsed with peptides corresponding to at least an immunogenic portion of a polypeptide disclosed herein. The resulting antigen-specific dendritic cells may either be transferred into a patient, or employed to stimulate T cells to provide antigen-specific T cells which may, in turn, be administered to a patient. The use of peptide-pulsed dendritic cells to generate antigen-specific T cells and the subsequent use of such antigen-specific T cells to eradicate disease in a murine model has been demonstrated by Cheever et al, *Immuological Reviews,* 157:177, 1997).

Additionally, vectors expressing the disclosed polynucleotides may be introduced into stem cells taken from the patient and clonally propagated in vitro for autologous transplant back into the same patient.

Routes and frequency of administration of pharmaceutical compositions and vaccines, as well as dosage, will vary from individual to individual. In general, the pharmaceutical compositions and vaccines may be administered by injection (e.g., intracutaneous, intramuscular, intravenous or subcutaneous), intranasally (e.g., by aspiration) or orally. Between 1 and 3 doses may be administered for a 1–36 week period. Preferably, 3 doses are administered, at intervals of 3–4 months, and booster vaccinations may be given periodically thereafter. Alternate protocols may be appropriate for individual patients. A suitable dose is an amount of polypeptide or DNA that, when administered as described above, is capable of raising an immune response in an immunized patient sufficient to protect the patient from Chlamydial infection for at least 1–2 years. In general, the amount of polypeptide present in a dose (or produced in situ by the DNA in a dose) ranges from about 1 pg to about 100 mg per kg of host, typically from about 10 pg to about 1 mg, and preferably from about 100 pg to about 1 µg. Suitable dose sizes will vary with the size of the patient, but will typically range from about 0.1 mL to about 5 mL.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109.

Any of a variety of non-specific immune response enhancers may be employed in the vaccines of this invention. For example, an adjuvant may be included. Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); SBAS2 and SBAS7 Adjuvants (SmithKline Beecham, London, England), aluminum salts such as aluminum hydroxide gel (alum) or aluminum phosphate, salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF or interleukin-2, -7, or -12, may also be used as adjuvants.

In certain vaccine formulations, an adjuvant composition designed to induce an immune response that is predominantly of the Th1 type may be indicated. Preferred adjuvants for use in eliciting a predominantly Th1-type response include, for example, a combination of monophosphoryl lipid A, preferably 3-de-O-acylated monophosphoryl lipid A (3D-MPL), together with an aluminum salt. MPL adjuvants are available from Ribi ImmunoChem Research Inc. (Hamillton, Mont.) (see U.S. Pat. Nos. 4,436,727; 4,877,611; 4,866,034 and 4,912,094). CpG-containing oligonucleotides (in which the CpG dinucleotide is unmethylated) also induce a predominantly Th1 response. Such oligonucleotides are well known and are described, for example, in WO 96/02555. Another preferred adjuvant is a saponin, preferably QS21, which may be used alone or in combination with other adjuvants. For example, an enhanced system involves the combination of a monophosphoryl lipid A and saponin derivative, such as the combination of QS21 and 3D-MPL as described in WO 94/00153, or a less reactogenic composition where the QS21 is quenched with cholesterol, as described in WO 96/33739. Other preferred formulations comprises an oil-in-water emulsion and tocopherol. A particularly potent adjuvant formulation involving QS21, 3D-MPL and tocopherol in an oil-in-water emulsion is described in WO 95/17210. Any vaccine provided herein may be prepared using well known methods that result in a combination of antigen, immune response enhancer and a suitable carrier or excipient.

The compositions described herein may be administered as part of a sustained release formulation (i.e., a formulation such as a capsule or sponge that effects a slow release of compound following administration). Such formulations may generally be prepared using well known technology and administered by, for example, oral, rectal or subcutaneous implantation, or by implantation at the desired target site. Sustained-release formulations may contain a polypeptide, polynucleotide or antibody dispersed in a carrier matrix and/or contained within a reservoir surrounded by a rate controlling membrane. Carriers for use within such formulations are biocompatible, and may also be biodegradable; preferably the formulation provides a relatively constant level of active component release. The amount of active compound contained within a sustained release formulation depends upon the site of implantation the rate and expected duration of release and the nature of the condition to be treated or prevented.

Any of a variety of delivery vehicles may be employed within pharmaceutical compositions and vaccines to facilitate production of an antigen-specific immune response that targets tumor cells. Delivery vehicles include antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-tumor effects per se and/or to be immunologically compatible with the receiver (i.e., matched HLA haplotype). APCs may generally be isolated from any of a variety of biological fluids and organs, including tumor and peritumoral tissues, and may be autologous, allogeneic, syngeneic or xenogeneic cells.

In another aspect, the present invention provides methods for using the polypeptides described above to diagnose Chlamydial infection. In this aspect, methods are provided for detecting Chlamydial infection in a biological sample, using one or more of the above polypeptides, either alone or in combination. For clarity, the term "polypeptide" will be used when describing specific embodiments of the inventive diagnostic methods. However, it will be clear to one of skill in the art that the fusion proteins of the present invention may also be employed in such methods.

As used herein, a "biological sample" is any antibody-containing sample obtained from a patient. Preferably, the sample is whole blood, sputum, serum, plasma, saliva, cerebrospinal fluid or urine. More preferably, the sample is a blood, serum or plasma sample obtained from a patient. The polypeptides are used in an assay, as described below, to determine the presence or absence of antibodies to the polypeptide(s) in the sample, relative to a predetermined cut-off value. The presence of such antibodies indicates previous sensitization to Chlamydia antigens which may be indicative of Chlamydia-infection.

In embodiments in which more than one polypeptide is employed, the polypeptides used are preferably complementary (i.e., one component polypeptide will tend to detect infection in samples where the infection would not be detected by another component polypeptide). Complementary polypeptides may generally be identified by using each polypeptide individually to evaluate serum samples obtained from a series of patients known to be infected with Chlamydia. After determining which samples test positive (as described below) with each polypeptide, combinations of two or more polypeptides may be formulated that are capable of detecting infection in most, or all, of the samples tested.

A variety of assay formats are known to those of ordinary skill in the art for using one or more polypeptides to detect antibodies in a sample. See, e.g., Harlow and Lane, *Antibodies: A Laboratory Manual,* Cold Spring Harbor Laboratory, 1988, which is incorporated herein by reference. In a preferred embodiment, the assay involves the use of polypeptide immobilized on a solid support to bind to and remove the antibody from the sample. The bound antibody may then be detected using a detection reagent that contains a reporter group. Suitable detection reagents include antibodies that bind to the antibody/polypeptide complex and free polypeptide labeled with a reporter group (e.g., in a semi-competitive assay). Alternatively, a competitive assay may be utilized, in which an antibody that binds to the polypeptide is labeled with a reporter group and allowed to bind to the immobilized antigen after incubation of the antigen with the sample. The extent to which components of the sample inhibit the binding of the labeled antibody to the polypeptide is indicative of the reactivity of the sample with the immobilized polypeptide.

The solid support may be any solid material known to those of ordinary skill in the art to which the antigen may be attached. For example, the solid support may be a test well in a microtiter plate, or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681.

The polypeptides may be bound to the solid support using a variety of techniques known to those of ordinary skill in the art. In the context of the present invention, the term "bound" refers to both noncovalent association, such as adsorption, and covalent attachment (which may be a direct linkage between the antigen and functional groups on the support or may be a linkage by way of a cross-linking agent). Binding by adsorption to a well in a microtiter plate or to a membrane is preferred. In such cases, adsorption may be achieved by contacting the polypeptide, in a suitable buffer, with the solid support for a suitable amount of time. The contact time varies with temperature, but is typically between about 1 hour and 1 day. In general, contacting a well of a plastic microtiter plate (such as polystyrene or polyvinylchloride) with an amount of polypeptide ranging from about 10 ng to about 1 $\mu$g, and preferably about 100 ng, is sufficient to bind an adequate amount of antigen.

Covalent attachment of polypeptide to a solid support may generally be achieved by first reacting the support with a bifunctional reagent that will react with both the support and a functional group, such as a hydroxyl or amino group, on the polypeptide. For example, the polypeptide may be bound to supports having an appropriate polymer coating using benzoquinone or by condensation of an aldehyde group on the support with an amine and an active hydrogen on the polypeptide (see, e.g., Pierce Immunotechnology Catalog and Handbook, 1991, at A12–A13).

In certain embodiments, the assay is an enzyme linked immunosorbent assay (ELISA). This assay may be performed by first contacting a polypeptide antigen that has been immobilized on a solid support, commonly the well of a microtiter plate, with the sample, such that antibodies to the polypeptide within the sample are allowed to bind to the immobilized polypeptide. Unbound sample is then removed from the immobilized polypeptide and a detection reagent capable of binding to the immobilized antibody-polypeptide complex is added. The amount of detection reagent that remains bound to the solid support is then determined using a method appropriate for the specific detection reagent.

More specifically, once the polypeptide is immobilized on the support as described above, the remaining protein binding sites on the support are typically blocked Any suitable blocking agent known to those of ordinary skill in the art, such as bovine serum albumin (BSA) or Tween 20™ (Sigma Chemical Co., St. Louis, Mo.) may be employed. The immobilized polypeptide is then incubated with the sample, and antibody is allowed to bind to the antigen. The sample may be diluted with a suitable dilutent, such as phosphate-buffered saline (PBS) prior to incubation. In general, an appropriate contact time (i.e., incubation time) is that period of time that is sufficient to detect the presence of antibody within an HGE-infected sample. Preferably, the contact time is sufficient to achieve a level of binding that is at least 95% of that achieved at equilibrium between bound and unbound antibody. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. Detection reagent may then be added to the solid support. An appropriate detection reagent is any compound that binds to the immobilized antibody-polypeptide complex and that can be detected by any of a variety of means known to those in the art. Preferably, the detection reagent contains a binding agent (such as, for example, Protein A, Protein G, immunoglobulin, lectin or free antigen) conjugated to a reporter group. Preferred reporter groups include enzymes (such as horseradish peroxidase), substrates, cofactors, inhibitors, dyes, radionuclides, luminescent groups, fluorescent groups and biotin. The conjugation of binding agent to reporter group may be achieved using standard methods known to those of ordinary skill in the art. Common binding agents may also be purchased conjugated to a variety of reporter groups from many commercial sources (e.g., Zymed Laboratories, San Francisco, Calif., and Pierce, Rockford, Ill.).

The detection reagent is then incubated with the immobilized antibody-polypeptide complex for an amount of time sufficient to detect the bound antibody. An appropriate amount of time may generally be determined from the manufacturer's instructions or by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of anti-Chlamydia antibodies in the sample, the signal detected from the reporter group that remains bound to the solid support is generally compared to a signal that corresponds to a predetermined cut-off value. In one preferred embodiment, the cut-off value is the average mean signal obtained when the immobilized antigen is incubated with samples from an uninfected patient. In general, a sample generating a signal that is three standard deviations above the predetermined cut-off value is considered positive for Chlamydia-infection. In an alternate preferred embodiment, the cut-off value is determined using a Receiver Operator Curve, according to the method of Sackett et al., *Clinical Epidemiology: A Basic Science for Clinical Medicine,* Little Brown and Co., 1985, pp. 106–107. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for Chlamydial infection.

In a related embodiment, the assay is performed in a rapid flow-through or strip test format, wherein the antigen is immobilized on a membrane, such as nitrocellulose. In the flow-through test, antibodies within the sample bind to the immobilized polypeptide as the sample passes through the membrane. A detection reagent (e.g., protein A-colloidal gold) then binds to the antibody-polypeptide complex as the solution containing the detection reagent flows through the membrane. The detection of bound detection reagent may then be performed as described above. In the strip test format, one end of the membrane to which polypeptide is bound is immersed in a solution containing the sample. The sample migrates along the membrane through a region containing detection reagent and to the area of immobilized polypeptide. Concentration of detection reagent at the polypeptide indicates the presence of anti-Chlamydia antibodies in the sample. Typically, the concentration of detection reagent at that site generates a pattern, such as a line, that can be read visually. The absence of such a pattern indicates a negative result. In general, the amount of polypeptide immobilized on the membrane is selected to generate a visually discernible pattern when the biological sample contains a level of antibodies that would be sufficient to generate a positive signal in an ELISA, as discussed above. Preferably, the amount of polypeptide immobilized on the membrane ranges from about 25 ng to about 1 $\mu$g, and more preferably from about 50 ng to about 500 ng. Such tests can typically be performed with a very small amount (e.g., one drop) of patient serum or blood.

Of course, numerous other assay protocols exist that are suitable for use with the polypeptides of the present invention. The above descriptions are intended to be exemplary only. One example of an alternative assay protocol which may be usefully employed in such methods is a Western blot, wherein the proteins present in a biological sample are separated on a gel, prior to exposure to a binding agent. Such techniques are well known to those of skill in the art.

In yet another aspect, the present invention provides antibodies to the polypeptides of the present invention. Antibodies may be prepared by any of a variety of techniques known to those of ordinary skill in the art. See, e.g., Harlow and Lane, *Antibodies: A Laboratory Manual,* Cold Spring Harbor Laboratory, Cold Spring Harbor, N.Y., 1988. In one such technique, an immunogen comprising the antigenic polypeptide is initially injected into any of a wide variety of mammals (e.g., mice, rats, rabbits, sheep and goats). The polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide or antigenic epitope may then be purified from such antisera by, for example, affinity chromatography using the polypeptide coupled to a suitable solid support.

Monoclonal antibodies specific for the antigenic polypeptide or epitope of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide or antigenic epitope of interest). Such cell lines may be produced, for example, from spleen-cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and tested for binding activity against the polypeptide or antigenic epitope. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides or antigenic epitopes of this invention may be used in the purification process in, for example, an affinity chromatography step.

Antibodies may be used in diagnostic tests to detect the presence of Chlamydia antigens using assays similar to those detailed above and other techniques well known to those of skill in the art, thereby providing a method for detecting Chlamydial infection in a patient.

Diagnostic reagents of the present invention may also comprise DNA sequences encoding one or more of the above polypeptides, or one or more portions thereof. For example, at least two oligonucleotide primers may be employed in a polymerase chain reaction (PCR) based assay to amplify Chlamydia-specific cDNA derived from a biological sample, wherein at least one of the oligonucleotide primers is specific for a DNA molecule encoding a polypeptide of the present invention. The presence of the amplified cDNA is then detected using techniques well known in the art, such as gel electrophoresis. Similarly, oligonucleotide probes specific for a DNA molecule encoding a polypeptide of the present invention may be used in a hybridization assay to detect the presence of an inventive polypeptide in a biological sample.

As used herein, the term "oligonucleotide primer/probe specific for a DNA molecule" means an oligonucleotide sequence that has at least about 80%, preferably at least about 90% and more preferably at least about 95%, identity to the DNA molecule in question. Oligonucleotide primers and/or probes which may be usefully employed in the inventive diagnostic methods preferably have at least about 10–40 nucleotides. In a preferred embodiment, the oligonucleotide primers comprise at least about 10 contiguous nucleotides of a DNA molecule encoding one of the polypeptides disclosed herein. Preferably, oligonucleotide probes for use in the inventive diagnostic methods comprise at least about 15 contiguous oligonucleotides of a DNA molecule encoding one of the polypeptides disclosed herein. Techniques for both PCR based assays and hybridization assays are well known in the art (see, for example, Mullis et al. Ibid, Ehrlich, Ibid). Primers or probes may thus be used to detect Chlamydia-specific sequences in biological samples. DNA probes or primers comprising oligonucleotide sequences described above may be used alone or in combination with each other.

The following Examples are offered by way of illustration and not by way of limitation.

EXAMPLE 1

Isolation of DNA Sequences Encoding Chlamydia Antigens

Chlamydia antigens of the present invention were isolated by expression cloning of a genomic DNA library of *Chlamydia trachomatis* LGV II essentially as described by Sanderson et al. (*J. Exp. Med.*, 1995, 182:1751–1757) and were shown to induce PBMC proliferation and IFN-γ in an immunoreactive T cell line.

A Chlamydia-specific T cell line was generated by stimulating PBMCs from a normal donor with no history of chlamydial genital tract infection with elementary bodies of *Chlamydia trachomatis* LGV II. This T cell line, referred to as TCL-8, was found to recognize both *Chlamydia trachomatis* and *Chlamydia pneumonia* infected monocyte-derived dendritic cells.

A randomly sheared genomic library of *Chlamydia trachomatis* LGV II was constructed in Lambda ZAP (Stratagene, La Jolla, Calif.) and the amplified library plated out in 96 well microtiter plates at a density of 30 ciones/well. Bacteria were induced to express recombinant protein in the presence of 2 mM IPTG for 3 h, then pelleted and resuspended in 200 µl of RPMI 10% FBS. 10 µl of the induced bacterial suspension was transferred to 96 well plates containing autologous monocyte-derived dendritic cells. After a 2 h incubation, dendritic cells were washed to remove free *E. coli* and Chlamydia-specific T cells were added. Positive *E. coli* pools were identified by determining IFN-γ production and proliferation of the T cells in response to the pools.

Four positive pools were identified, which were broken down to yield four pure clones (referred to as 1-B1-66, 4-D7-28, 3-G3-10 and 10-C10-31), with insert sizes of 481 bp, 183 bp, 110 bp and 1400 bp, respectively. The determined DNA sequences for 1-B1-66, 4-D7-28, 3-G3-10 and 10-C10-31 are provided in SEQ ID NO: 1–4, respectively. Clone 1-B1-66 is approximately in region 536690 of the *C. trachomatis* genome (NCBI *C. trachomatis* database). Within clone 1-B1-66, an open reading frame (ORF) has been identified (nucleotides 115–375) that encodes a previously identified 9 kDa protein (Stephens, et al. Genbank Accession No. AE001320), the sequence of which is provided in SEQ ID NO: 5). Clone 4-D7-28 is a smaller region of the same ORF (amino acids 22–82 of 1-B1-66). Clone 3-G3-10 is approximately in region 74559 of the *C. trachomatis* genome. The insert is cloned in the antisense orientation with respect to its orientation in the genome. The clone 10-C10-31 contains an open reading frame that corresponds to a previously published sequence for S13 ribosomal protein from Chlamydia trachomatis (Gu, L. et al. *J. Bacteriology*, 177:2594–2601, 1995). The predicted protein sequences for 4-D7-28 and 10-C10-31 are provided in SEQ ID NO: 6 and 12, respectively. Predicted protein sequences for 3-G3-10 are provided in SEQ ID NO: 7–11.

In a related series of screening studies, an additional T cell line was used to screen the genomic DNA library of *Chlamydia trachomatis* LGV II described above. A Chlamydia-specific T cell line (TCT-1) was derived from a patient with a chlamydial genital tract infection by stimulating patient PBMC with autologous monocyte-derived dendritic cells infected with elementary bodies of *Chlamydia trachomatis* LGV II. One clone, 4C9-18 (SEQ ID NO: 21), containing a 1256 bp insert, elicited a specific immune response, as measured by standard proliferation assays, from the Chlamydia-specific T cell line TCT-1. Subsequent analysis revealed this clone to contain three known sequences: lipoamide dehydrogenase (Genbank Accession No. AE001326), disclosed in SEQ ID NO: 22; a hypothetical protein CT429 (Genbank Accession No. AE001316), disclosed in SEQ ID NO: 23; and part of an open reading frame of ubiquinone methyltransferase CT428 (Genbank Accession No. AE001316), disclosed in SEQ ID NO: 24.

In further studies involving clone 4C9-18 (SEQ ID NO: 21), the full-length amino acid sequence for lipoamide dehydrognase (SEQ ID NO: 22) from *C. trachomatis* (LGV II) was expressed in clone CtL2-LPDA-FL, as disclosed in SEQ ID NO: 90.

To further characterize the open reading frame containing the T cell stimulating epitope(s), a cDNA fragment containing nucleotides 1–695 of clone 4C9-18 with a cDNA sequence encoding a 6X-Histidine tag on the amino terminus was subcloned into the NdeI/EcoRI site of the pET17b vector (Novagen, Madison, Wis.), referred to as clone 4C9-18#2 BL21 pLysS (SEQ ID NO: 25, with the corresponding amino acid sequence provided in SEQ ID NO: 26) and transformed into *E. coli*. selective induction of the transformed *E. coli* with 2 mM IPTG for three hours resulted in the expression of: a 26 kDa protein from clone 4C9-18#2 BL21 pLysS, as evidenced by standard Coomassie-stained SDS-PAGE. To determine the immunogenicity of the protein encoded by clone 4C9-18#2 BL21 pLysS, *E. coli* expressing the 26 kDa protein were titered onto $1 \times 10^4$ monocyte-derived dendritic cells and incubated for two hours. The dendritic cell cultures were washed and $2.5 \times 10^4$ T cells (TCT-1) added and allowed to incubate for an additional 72 hours, at which time the level of IFN-γ in the culture supernatant was determined by ELISA. As shown in FIG. 1, the T-cell line TCT-1 was found to respond to induced cultures as measured by IFN-γ, indicating a Chlamydia-specific T-cell response against the lipoamide dehydrogenase sequence. Similarly, the protein encoded by clone 4C9-18#2 BL21 pLysS was shown to stimulate the TCT-1 T-cell line by standard proliferation assays. Subsequent studies to identify additional *Chlamydia trachomatis* antigens using the above-described CD4+ T-cell expression cloning technique yielded additional clones. The TCT-1 and TCL-8 Chlamydia-specific T-cell lines, as well as the TCP-21 T-cell line were utilized to screen the *Chlamydia trachomatis* LGVII genomic library. The TCP-21 T-cell line was derived from a patient having a humoral immune response to *Chlamydia pnuemoniae*. The TCT-1 cell line identified 37 positive pools, the TCT-3 cell line identified 41 positive pools and the TCP-21 cell line identified 2 positive pools. The following clones were derived from 10 of these positive pools. Clone 11-A3-93 (SEQ ID NO: 64), identified by the TCP-21 cell line, is a 1339 bp genomic fragment sharing homology to the HAD superfamily (CT103). The second insert in the same clone shares homology with the fab I gene (CT104) present on the complementary strand. Clone 11-C12-91 (SEQ ID NO: 63), identified using the TCP-21 cell line, has a 269 bp insert that is part of the OMP2 gene (CT443) and shares homology with the 60 kDa cysteine rich outer membrane protein of *C. pnuemoniae*.

Clone 11-G10-46, (SEQ ID NO: 62), identilied using the TCT-3 cell line, contains a 688 bp insert that shares homology to the hypothetical protein CT610. Clone 11-G1-34, (SEQ ID NO: 61), identified using the TCT-3 cell line has two partial open reading frames (ORF) with an insert size of 1215 bp. One ORF shares homology to the malate dehydrogenase gene (CT376), and the other ORF shares homology to the glycogen hydrolase gene (CT042). Clone 11-H3-68, (SEQ ID NO: 60), identified using the TCT-3 cell line, has two ORFs with a total insert size of 1180 bp. One partial ORF encodes the plasmid-encoded PGP6-D virulence protein while the second ORF is a complete ORF for the L1 ribosomal gene (CT318). Clone 11-H4-28, (SEQ ID NO: 59), identified using the TCT-3 cell line, has an insert size of 552 bp and is part of the ORF for the dnaK gene (CT396). Clone 12-B3-95, (SEQ ID NO: 58), identified using the TCT-1 cell line, has an insert size of 463 bp and is a part of the ORF for for the lipoamide dehydrogenase gene (CT557). Clones 15-G1-89 and 12-B3-95 are identical, (SEQ ID NO: 55 and 58, respectively), identified using the TCT-1 cell line, has an insert size of 463 bp and is part of the ORF for the lipoamide dehydrogenase gene (CT557). Clone 12-G3-83, (SEQ ID NO: 57), identified using the TCT-1 cell line has an insert size of 1537 bp and has part of the ORF for the hypothetical protein CT622.

Clone 23-G7-68, (SEQ ID NO: 79), identified using the TCT-3 cell line, contains a 950 bp insert and contains a small part of the L11 ribosomal ORF, the entire ORF for L1 ribosomal protein and a part of the ORF for L10 ribosomal protein. Clone 22-F8-91, (SEQ ID NO: 80), identified using the TCT-1 cell line, contains a 395 bp insert that contains a part of the pmpC ORF on the complementary strand of the clone. Clone 21-E8-95, (SEQ ID NO: 81), identified using the TCT-3 cell line, contains a 2,085 bp insert which contains part of CT613 ORF, the complete ORF for CT612, the complete ORF for CT611 and part of the ORF for CT610. Clone 19-F12-57, (SEQ ID NO: 82), identified using the TCT-3 cell line, contains a 405 bp insert which contains part of the CT 858 ORF and a small part of the recA ORF. Clone 19-F12-53, (SEQ ID NO: 83), identified using the TCT-3 cell line, contains a 379 bp insert that is part of the ORF for CT455 encoding glutamyl tRNA synthetase. Clone 19-A5-54, (SEQ ID NO: 84), identified using the TCT-3 cell line, contains a 715 bp insert that is part of the ORF3 (complementary strand of the clone) of the cryptic plasmid. Clone 17-E11-72, (SEQ ID NO: 85), identified using the TCT-1 cell line, contains a 476 bp insert that is part of the ORF for Opp_2 and pmpD. The pmpD region of this clone is covered by the pmpD region of clone 15-H2-76. Clone 17-C1-77, (SEQ ID NO: 86), identified using the TCT-3 cell line, contains a 1551 bp insert that is part of the CT857 ORF, as well as part of the CT858 ORF. Clone 15-H2-76, (SEQ ID NO: 87), identified using the TCT-1 cell line, contains a 3,031 bp insert that contains a large part of the pmpD ORF, part of the CT089 ORF, as well as part of the ORF for SycE. Clone 15-A3-26, (SEQ ID NO: 88), contains a 976 bp insert that contains part of the ORF for CT858.

Clone 14-H1-4, (SEQ ID NO: 56), identified using the TCT-3 cell line, contains a complete ORF for the TSA gene, thiol specific antioxidant—CT603 (the CT603 ORF is a homolog of CPn0778 from *C. pneumoniae*). The TSA open reading frame in clone 14-H1-4 was amplified such that the expressed protein possess an additional methionine and a 6x histidine tag (amino terminal end). This amplified insert was sub-cloned into the Nde/EcoRI sites of the pET17b vector. Upon induction of this clone with IPTG, a 22.6 kDa protein was purified by Ni-NTA agarose affinity chromatography. The determined amino acid sequence for the 195 amino acid ORF of clone 14-H1-4 encoding the TSA gene is provided in SEQ ID NO: 65. Further analysis yielded a full-length clone for the TSA gene, referred to as CTL2-TSA-FL, with the full-length amino acid sequence provided in SEQ ID NO: 92.

Additional Chlamydia antigens were obtained by screening a genomic expression library of *Chlamydia trachomatis* (LGV II serovar) in Lambda Screen-1 vector (Novagen, Madison, Wis.) with sera pooled from several Chlamydia-infected individuals using techniques well known in the art. The following immuno-reactive clones were identified and the inserts containing Chlamydia genes sequenced: CTL2#1 (SEQ ID NO: 71); CTL2#2 (SEQ ID NO: 70); CTL2#3-5' (SEQ ID NO: 72, a first determined genomic sequence representing the 5' end); CTL2#3-3' (SEQ ID NO: 73, a second determined genomic sequence representing the 3' end); CTL2#4 (SEQ ID NO: 53); CTL2#5 (SEQ ID NO: 69); CTL2#6 (SEQ ID NO: 68); CTL2#7 (SEQ ID NO: 67); CTL2#8b (SEQ ID NO: 54); CTL2#9 (SEQ ID NO: 66); CTL2#10-5' (SEQ ID NO: 74, a first determined genomic sequence representing the 5' end); CTL2#10-3' (SEQ ID NO: 75, a second determined genomic sequence representing the 3' end); CTL2#11-5' (SEQ ID NO: 45, a first determined genomic sequence representing the 5' end); CTL2#11-3' (SEQ ID NO: 44, as econd determined genomic sequence representing the 3' end); CTL2#12 (SEQ ID NO: 46); CTL2#16-5' (SEQ ID NO: 47); CTL2#18-5' (SEQ ID NO: 49, a first determined genomic sequence representing the 5' end); CTL2#18-3' (SEQ ID NO: 48, a second determined genomic sequence representing the 3' end); CTL2#19-5' (SEQ ID NO: 76, the determined genomic sequence representing the 5' end); CTL2#21 (SEQ ID NO: 50); CTL2#23 (SEQ ID NO: 51; and CTL2#24 (SEQ ID NO: 52).

EXAMPLE 2

Induction of T Cell Proliferation and Interferon-γ Production by *Chlamydia Trachomatis* Antigens The ability of recombinant *Chlamydia trachomatis* antigens to induce T cell proliferation and interferon-γ production is determined as follows.

Proteins are induced by IPTG and purified by Ni-NTA agarose affinity chromatograph (Webb et al., *J. Immunology* 157:5034–5041, 1996). The purified polypeptides are then screened for the ability to induce T-cell proliferation in PBMC preparations. PBMCs from *C. trachomatis* patients as well as from normal donors whose T-cells are known to proliferate in response to Chlamydia antigens, are cultured in medium comprising RPMI 1640 supplemented with 10% pooled human serum and 50 μg/ml gentamicin. Purified polypeptides are added in duplicate at concentrations of 0.5 to 10 μg/mL. After six days of culture in 96-well round-bottom plates in a volume of 200 μl, 50 μl of medium is removed from each well for determination of IFN-γ levels, as described below. The plates are then pulsed with 1 μCi/well of tritiated thymidine for a further 18 hours, harvested and tritium uptake determined using a gas scintillation counter. Fractions that result in proliferation in both replicates three fold greater than the proliferation observed in cells cultured in medium alone are considered positive.

IFN-γ is measured using an enzyme-linked immunosorbent assay (ELISA). ELISA plates are coated with a mouse monoclonal antibody directed to human IFN-γ (PharMingen, San Diego, Calif.) in PBS for four hours at room temperature. Wells are then blocked with PBS containing 5% (W/V) non-fat dried milk for 1 hour at room temperature. The plates are washed six times in PBS/0.2% TWEEN-20 and samples diluted 1:2 in culture medium in the ELISA plates are incubated overnight at room temperature. The plates are again washed and a polyclonal rabbit anti-human IFN-γ serum diluted 1:3000 in PBS/10% normal goat serum is added to each well. The plates are then incubated for two hours at room temperature, washed and horseradish peroxidase-coupled anti-rabbit IgG (Sigma Chemical So., St. Louis, Mo.) is added at a 1:2000 dilution in PBS/5% non-fat dried milk. After a further two hour incubation at room temperature, the plates are washed and TMB substrate added. The reaction is stopped after 20 min with 1 N sulfuric acid. Optical density is determined at 450 nm using 570 nm as a reference wavelength. Fractions that result in both replicates giving an OD two fold greater than the mean OD from cells cultured in medium alone, plus 3 standard deviations, are considered positive.

Using the above methodology, recombinant 1B1-66 protein (SEQ ID NO: 5) as well as two synthetic peptides corresponding to amino acid residues 48–67 (SEQ ID NO: 13; referred to as 1-B1-66/48-67) and 58–77 (SEQ ID NO: 14, referred to as 1B1-66/58-77), respectively, of SEQ ID NO: 5, were found to induce a proliferative response and IFN-γ production in a Chlamydia-specific T cell line used to screen a genomic library of *C. trachomatis* LGV II.

Further studies have identified a *C. trachomatis*-specific T-cell epitope in the ribosomal S13 protein. Employing standard epitope mapping techniques well known in the art, two T-cell epitopes in the ribosomal S13 protein (rS13) were identified with a Chlamydia-specific T-cell line from donor CL-8 (T-cell line TCL-8 EB/DC). FIG. 8 illustrates that the first peptide, rS13 1–20 (SEQ ID NO: 106), is 100% identical with the corresponding *C. pneumoniae* sequence, explaining the cross-reactivity of the T-cell line to recombinant *C. trachomatis* and *C. pneumoniae*-rS13. The response to the second peptide rS13 56–75 (SEQ ID NO: 108) is *C. trachomatis*-specific, indicating that the rS13 response in this healthy asymptomatic donor was elicited by exposure to *C. trachomatis* and not to *C. pneumoniae,* or any other microbial infection.

EXAMPLE 3

Preparation of Synthetic Polypeptides

Polypeptides may be synthesized on a Millipore 9050 peptide synthesizer using FMOC chemistry with HPTU (O-Benzotriazole-N,N,N',N'-tetramethyluronium hexafluorophosphate) activation. A Gly-Cys-Gly sequence may be attached to the amino terminus of the peptide to provide a method of conjugating or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0–60% acetonitrile (containing 0.1% TFA) in water (containing 0.1% TFA) may be used to elute the peptides. Following lyophilization of the pure fractions, the peptides may be characterized using electrospray mass spectrometry and by amino acid analysis.

EXAMPLE 4

Figure 2:
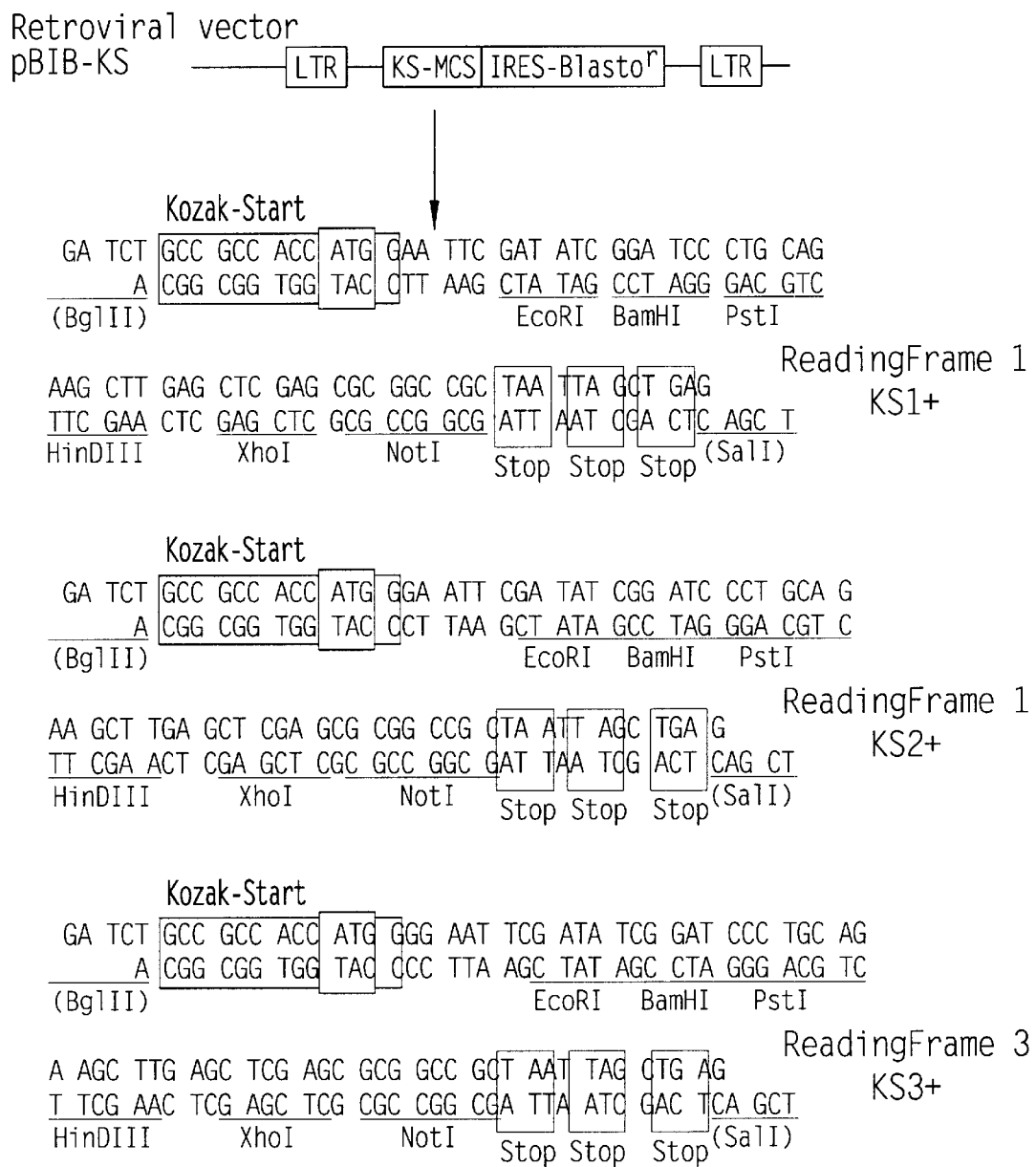
FIG. 2 illustrates retroviral vectors pBIB-KS1,2,3 modified to contain a Kosak translation initiation site and stop codons.
Figure 3:
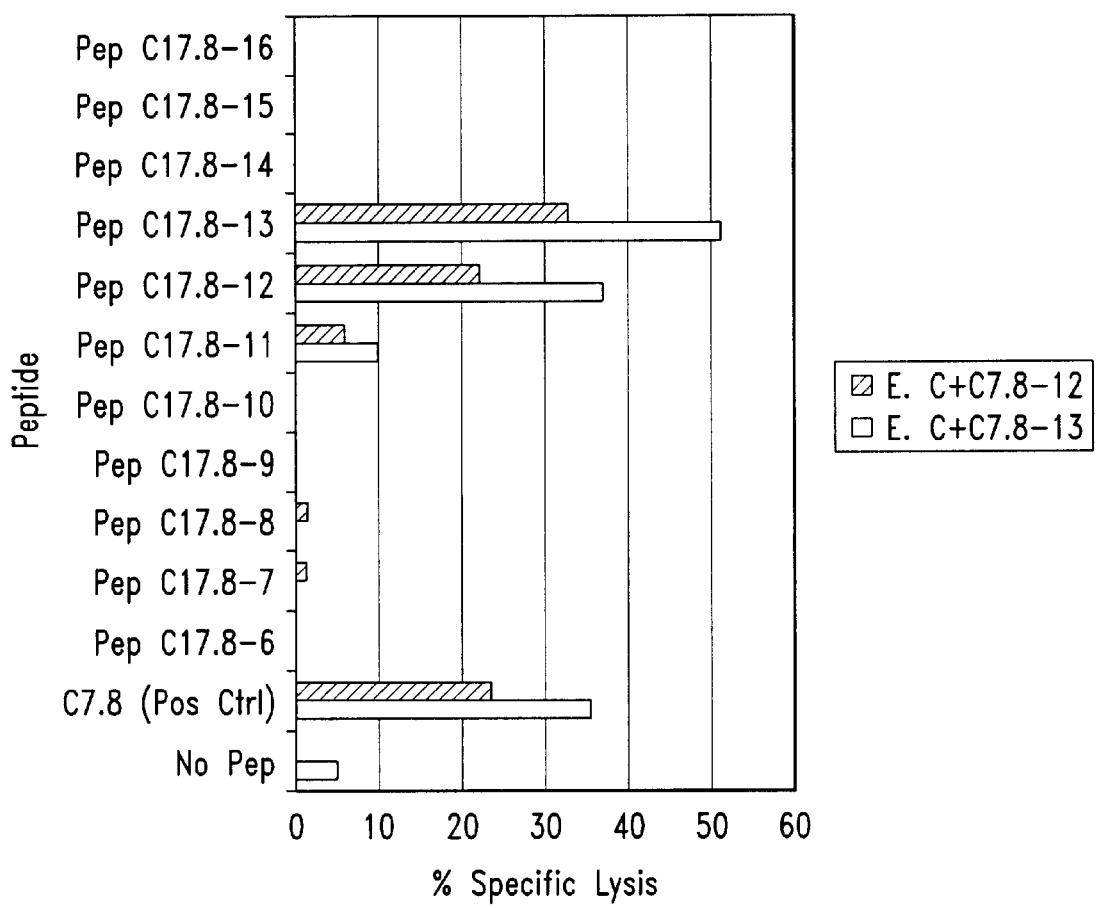
FIG. 3 shows specific lysis in a chromium release assay of P815 cells pulsed with Chlamydia peptides CtC7.8–12 (SEQ ID NO: 18) and CtC7.8–13 (SEQ ID NO: 19).
Figure 4:
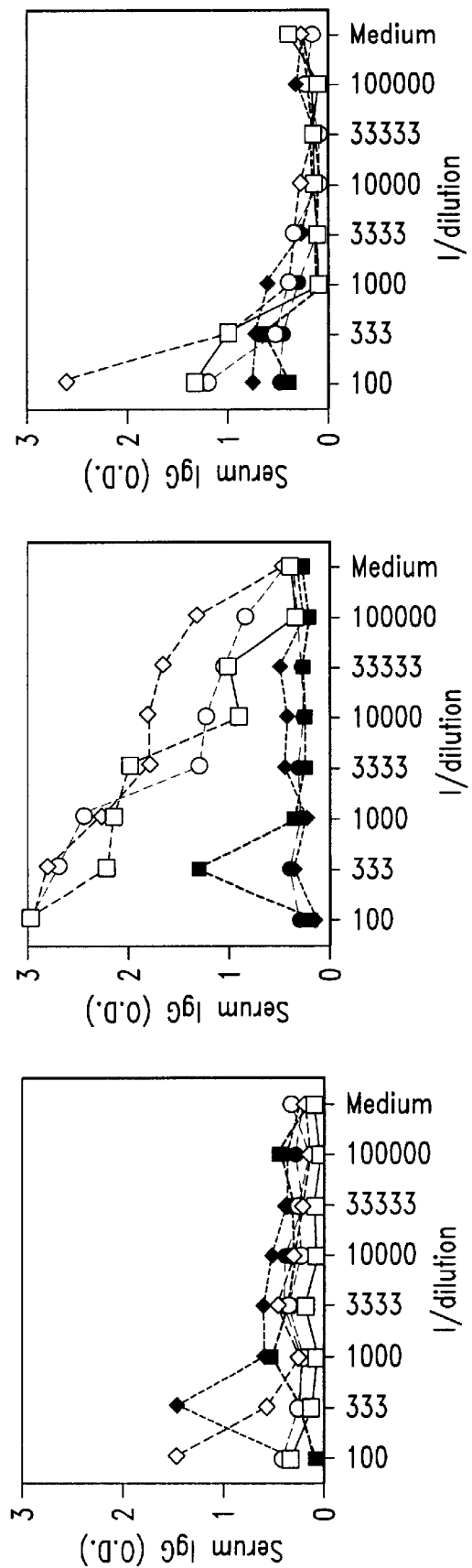
FIG. 4 shows antibody isotype titers in C57B/16 mice immunized with *C. trachomatis* SWIB protein.
Figure 5:
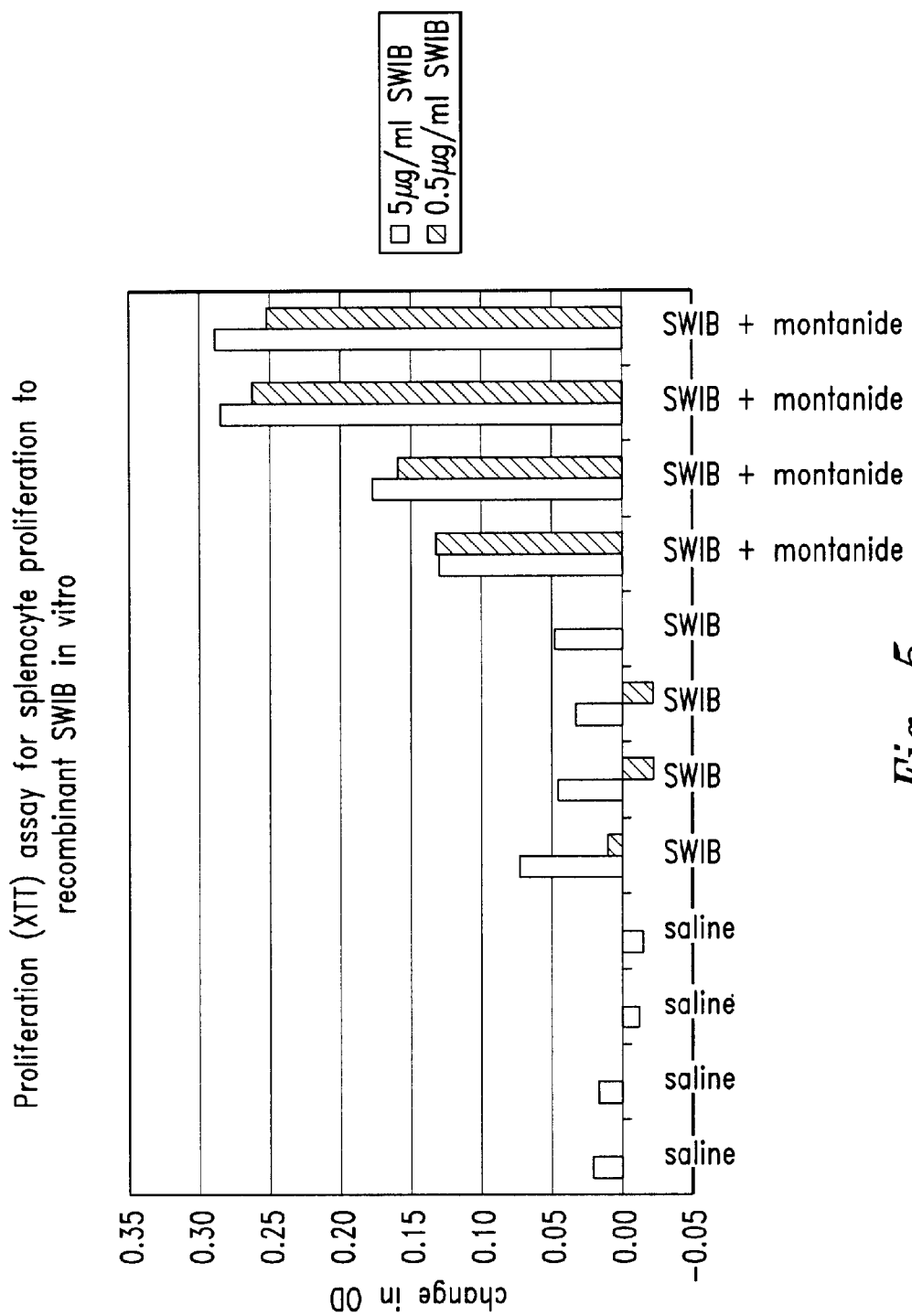
FIG. 5 shows Chlamydia-specific T-cell proliferative responses in splenocytes from C3H mice immunized with *C. trachomatis* SWIB protein.
Figure 7A:
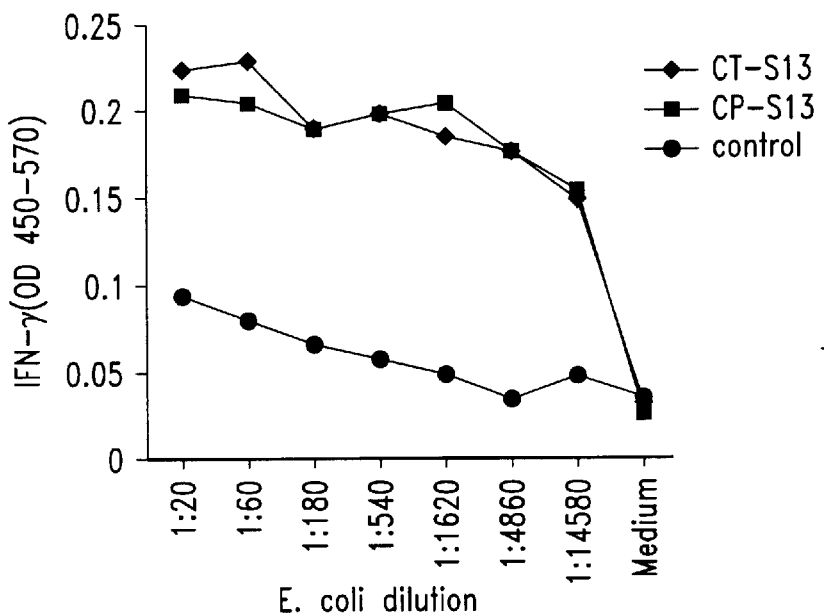
FIGS. 7A and 7B show induction of IFN-γ from a human anti-chlamydia T-cell line (TCL-8) capable of cross-reacting to *C. trachomatis* and *C. pneumonia* upon activation by monocyte-derived dendritic cells expressing chlamydial proteins.
Figure 7B:
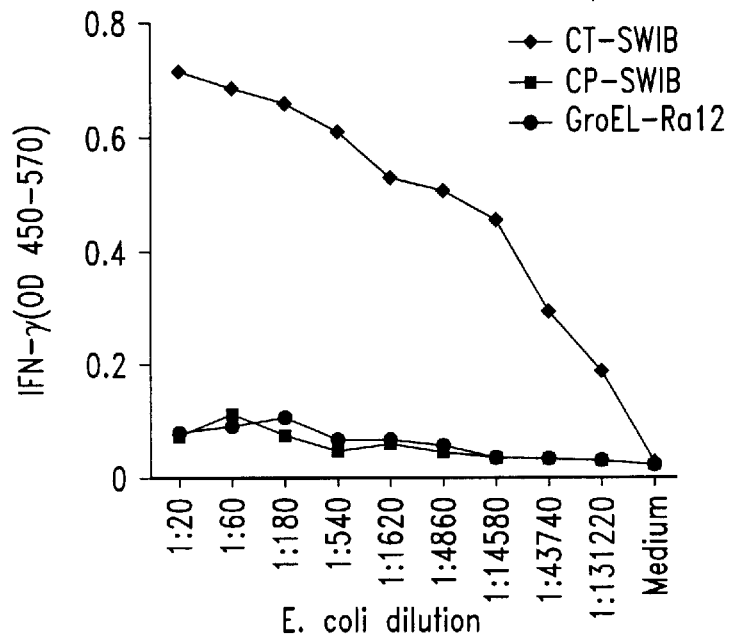

Lysis of Target Cells by a Murine CD8+ T-Cell Line Specific for Chlamydia Antigens A genomic library of *Chlamydia trachomatis* LGV II was constructed by limited digests using BamHI, BglII, BstYi and MboI restriction enzymes. The restriction digest fragments were subsequently ligated into the BamHI site of the retroviral vectors pBIB-KS1,2,3. This vector set was modified to contain a Kosak translation initiation site and stop codons in order to allow expression of proteins from short DNA genomic fragments, as shown in FIG. 2. DNA pools of 80 clones were prepared and transfected into the retroviral packaging line Phoenix-Ampho, as described in Pear, W. S., Scott, M. L. and Nolan, G. P., Generation of High Titre, Helper-free Retroviruses by Transient Transfection. Methods in Molecular Medicine: Gene Therapy Protocols, Humana Press, Totowa, N.J., pp. 41–57. The Chlamydia library in retroviral form was then transduced into H2-Ld expressing P815 cells, which were then used as target cells to stimulate an antigen specific T-cell line.

A Chlamydia-specific, murine H2-Ld restricted CD8+ T-cell line was expanded in culture by repeated rounds of stimulation with irradiated *C. trachomatis*-infected J774 cells and irradiated syngeneic spleen cells, as described by Starnbach, M., in *J. Immunol.,* 153:5183, 1994. This Chlamydia-specific T-cell line was used to screen the above Chlamydia genomic library expressed by the retrovirally-transduced P815 cells. Positive DNA pools were identified by detection of IFN-γ production using Elispot analysis (see Lalvani et al., *J. Experimental Medicine* 186:859–865, 1997).

Two positive pools, referred to as 2C7 and 2E10, were identified by standard chromium release assays. Stable transductants of P815 cells from pool 2C7 were cloned by limiting dilution and individual clones were selected based upon their capacity to elicit IFN-γ production from the Chlamydia-specific CTL line. From this screening process, four positive clones were selected, referred to as 2C7-8, 2C7-9, 2C7-19 and 2C7-21.

Transgenic DNA from these four positive clones was PCR amplified using pBIB-KS specific primers to selectively amplify the Chlamydia DNA insert Amplified inserts were gel purified and sequenced. One immunoreactive clone, 2C7-8 (SEQ ID NO: 15, with the predicted amino acid sequence provided in SEQ ID NO: 32), is a 160 bp fragment with homology to nucleotides 597304–597145 of *Chlamydia trachomatis,* serovar D (NCBI, BLASTN search; SEQ ID NO: 33, with the predicted amino acid sequence provided in SEQ ID NO: 34). The sequence of clone 2C7-8 maps within two putative open reading frames from the region of high homology described immediately above, and in particular, one of these putative open reading frames, consisting of a 298 amino acid fragment (SEQ ID NO: 16, with the predicted amino acid sequence provided in SEQ ID NO: 17), was demonstrated to exhibit immunological activity.

To determine if these two putative open reading frames (SEQ ID NO: 16 and 20) encoded a protein with an associated immunological function, overlapping peptides (17–20 amino acid lengths) spanning the lengths of the two open reading frames were synthesized, as described in Example 3. A standard chromium release assay was utilized to determine the per cent specific lysis of peptide-pulsed H2-Ld restricted target cells. In this assay, aliquots of P815 cells (H2-Ld) were labeled at 37° C. for one hour with 100 $\mu$Ci of $^{51}$Cr in the presence or absence of 1 $\mu$g/ml of the indicated peptides. Following this incubation, labeled P815 cells were washed to remove excess $^{51}$Cr and peptide, and subsequently plated in duplicate in microculture plates at a concentration of 1,000 cells/well. Effector CTL (Chlamydia-specific CD8 T cells) were added at the indicated effector-:target ratios. Following a 4 hour incubation, supernatants were harvested and measured by gamma-counter for release of $^{51}$Cr into the supernatant. Two overlapping peptides from the 298 amino acid open reading frame did specifically stimulate the CTL line. As shown in FIG. 3, peptides CtC7.8-12 (SEQ ID NO: 18) and CtC7.8-13(SEQ ID NO: 19) were able to elicit 38 to 52% specific lysis, respectively, at an effector to target ratio of 10:1. Notably, the overlap between these two peptides contained a predicted Ld binding peptide. A 10 amino acid peptide was synthesized to correspond to this overlapping sequence (SEQ ID NO: 31) and was found to generate a strong immune response from the anti-Chlamydia CTL line by elispot assay. Significantly, a search of the most recent Genbank database revealed no proteins have previously been described for this gene. Therefore, the putative open reading frame encoding clone 2C7-8 (SEQ ID NO: 15) defines a gene which encompasses an antigen from Chlamydia capable of stimulating antigen-specific CD8+ T-cells in a MHC-I restricted manner, demonstrating this antigen could be used to develop a vaccine against Chlamydia.

EXAMPLE 5

Generation of Antibody and CD4+ T-Cell Responses in Mice Immunized with Chlamydia Antigens Immunogenicity studies were conducted to determine the antibody and CD4+ T cell responses in mice immunized with either purified SWIB or S13 proteins formulated with Montanide adjuvant, or DNA-based immunizations with pcDNA-3 expression vectors containing the DNA sequences for SWIB or S13. SWIB is also referred to as clone 1-B1-66 (SEQ ID NO: 1, with the corresponding amino acid sequence provided in SEQ ID NO: 5), and S13 ribosomal protein is also referred to as clone 10-C10-31 (SEQ ID NO: 4, with the corresponding amino acid sequence provided in SEQ ID NO: 12). In the first experiment, groups of three C57BL/6 mice were immunized twice and monitored for antibody and CD4+ T-cell responses. DNA immunizations were intradermal at the base of the tail and polypeptide immunizations were administered by subcutaneous route. Results from standard $^3$H-incorporation assays of spleen cells from immunized mice shows a strong proliferative response from the group immunized with purified recombinant SWIB polypeptide (SEQ ID NO: 5). Further analysis by cytokine induction assays, as previously described, demonstrated that the group immunized with SWIB polypeptide produced a measurable IFN-γ and IL-4 response. Subsequent ELISA-based assays to determine the predominant antibody isotype response in the experimental group immunized with the SWIB polypeptide were performed. FIG. 4 illustrates the SWIB-immunized group gave a humoral response that was predominantly IgG1.

In a second experiment, C3H mice were immunized three times with 10 $\mu$g purified SWIB protein (also referred to as clone 1-B1-66, SEQ ID NO: 5) formulated in either PBS or Montanide at three week intervals and harvested two weeks after the third immunization. Antibody titers directed against the SWIB protein were determined by standard ELISA-based techniques well known in the art, demonstrating the SWIB protein formulated with Montanide adjuvant induced a strong humoral immune response. T-cell proliferative responses were determined by a XTT-based assay (Scudiero, et al, *Cancer Research,* 1988, 48:4827). As shown in FIG. 5, splenocytes from mice immunized with the SWIB polypeptide plus Montanide elicited an antigen specific proliferative response. In addition, the capacity of splenocytes from immunized animals to secrete IFN-γ in response to soluble recombinant SWIB polypeptide was determined using the cytokine induction assay previously described. The splenocytes from all animals in the group immunized with SWIB polypeptide formulated with montanide adjuvant secreted IFN-γ in response to exposure to the SWIB Chlamydia antigen, demonstrating an Chlamydia-specific immune response.

In a further experiment, C3H mice were immunized at three separate time points at the base of the tail with 10 μg of purified SWIB or S13 protein (C. trachomatis, SWIB protein, clone 1-B1-66, SEQ ID-NO: 5, and S13 protein, clone 10-C10-31, SEQ ID NO: 4) formulated with the SBAS2 adjuvant (SmithKline Beecham, London, England). Antigen-specific antibody titers were measured by ELISA, showing both polypeptides induced a strong IgG response, ranging in titers from $1 \times 10^{-4}$ to $1 \times 10^{-5}$ The IgG1 and IgG2a components of this response were present in fairly equal amounts. Antigen-specific T-cell proliferative responses, determined by standard $^3$H-incorporation assays on spleen cells isolated from immunized mice, were quite strong for SWIB (50,000 cpm above the negative control) and even stronger for s13 (100,000 cpm above the negative control). The IFNγ production was assayed by standard ELISA techniques from supernatant from the proliferating culture. In vitro restimulation of the culture with S13 protein induced high levels of IFNγ production, approximately 25 ng/ml versus 2 ng/ml for the negative control. Restimulation with the SWIB protein also induced IFNγ, although to a lesser extent.

In a related experiment, C3H mice were immunized at three separate time points with 10 μg of purified SWIB or S13 protein (C. trachomatis, SWIB protein, clone 1-B1-66, SEQ ID NO: 5, and S13 protein, clone 10-C10-31, SEQ ID NO: 4) mixed with 10 μg of Cholera Toxin. Mucosal immunization was through intranasal inoculation. Antigen-specific antibody responses were determined by standard ELISA techniques. Antigen-specific IgG antibodies were present in the blood of SWIB-immunized mice, with titers ranging from $1 \times 10^{-3}$ to $1 \times 10^{-4}$, but non-detectable in the S13-immunized animals. Antigen-specific T-cell responses from isolated splenocytes, as measured by IFNγ production, gave similar results to those described immediately above for systemic immunization.

A protection study was conducted in mice to determine whether DNA-based immunization with SWIB can influence genital tract disease resulting from chlamydial elementary bodies inoculation. Two models were utilized; a model of intravaginal inoculation that uses a human isolate containing a strain of Chlamydia psittaci, and a model of intrauterine inoculation that involves a human isolate identified as Chlamydia trachomatis,* serovar F. Both strains induce inflammation in the upper genital tract, which resemble endometritis and salpingitis caused by *Chlamydia trachomatis.* C3H mice were immunized at three time points at the base of the tail with 100 μg of pcDNA-3 expression vector containing SWIB DNA (*C. trachomatis,* as described above). Two weeks post the third immunization, animals were treated with progesterone and infected, either through intravaginal or intrauterine inoculation. Two weeks post infection, mice were sacrificed and genital tracts sectioned, stained and examined for histopathology. In the intrauterine-inoculation model, mock-immunized animals receiving empty vector showed consistent inflammation with an ovary/oviduct mean inflammation score of 6.12, versus 2.62 for the DNA-immunized group. In the model of vaginal inoculation and ascending infection, mock-immunized mice had an ovary/oviduct mean inflammation score of 8.37 versus 5 for the DNA-immunized group. Additionally, in a later model, vaccinated mice showed no signs of tubal occlusion while negative control mice had inflammatory cells in the lumen of the oviduct.

EXAMPLE 6

Expression and Characterization of *Chlamydia Pneumoniae* Genes

The human T-cell line, TCL-8, described in Example 1, recognizes *Chlamydia trachomatis* as well as *Chlamydia pneumonia* infected monocyte-derived dendritic cells, suggesting *Chlamydia trachomatis* and *pneumonia* may encode cross-reactive T-cell epitopes. To isolate the *Chlamydia pneumonia* genes homologous to *Chlamydia trachomatis* LGV II clones 1B1-66, also referred to as SWIB (SEQ ID NO: 1) and clone 10C10-31, also referred to as S13 ribosomal protein (SEQ ID NO: 4), HeLa 229 cells were infected with *C. pneumonia* strain TWAR (CDC/CWL-029). After three days incubation, the *C. pneumonia*-infected HeLa cells were harvested, washed and resuspended in 200 μl water and heated in a boiling water bath for 20 minutes. Ten microliters of the disrupted cell suspension was used as the PCR template.

*C. pneumonia* specific primers were designed for clones 1B1-66 and 10C10-31 such that the 5' end had a 6X-Histidine tag and a Nde I site inserted, and the 3" end had a stop codon and a BamHI site included (FIG. 6). The PCR products were amplified and sequenced by standard techniques well known in the art. The *C. pneumonia*-specific PCR products were cloned into expression vector pET17B (Novagen, Madison, Wis.) and transfected into *E. coli* BL21 pLysS for expression and subsequent purification utilizing the histidine-nickel chromatographic methodology provided by Novagen. Two proteins from *C. pneumonia* were thus generated, a 10–11 kDa protein referred to as CpSWIB (SEQ ID NO: 27, and SEQ ID NO: 78 having a 6×His tag, with the corresponding amino acid sequence provided in SEQ ID NO: 28, respectively), a 15 kDa protein referred to as CpS13 (SEQ ID NO: 29, and SEQ ID NO: 77, having a 6X His tag, with the corresponding amino acid sequence provided in SEQ ID NO: 30 and 91, respectively). A human anti-chlamydia T-cell line (TCL-8) capable of cross-reacting to *C. trachomatis* and *C. pneumonia* was used to determine whether the expressed proteins. possessed T-cell epitopes common to both *C. trachomatis* and *C. pneumonia.* Briefly, *E. coli* expressing chlamydial proteins were titered on $1\times10^4$ monocyte-derived dendritic cells. After two hours, the dendritic cells cultures were washed and $2.5\times10^4$ T cells (TCL-8) added and allowed to incubate for an additional 72 hours. The amount of INF-γ in the culture supernatant was then determined by ELISA. As shown in FIGS. 7A and 7B, the TCL-8 T-cell line specifically recognized the S13 ribosomal protein from both *C. trachomatis* and *C. pneumonia* as demonstrated by the antigen-specific induction of IFN-γ, whereas only the SWIB protein from *C. trachomatis* was recognized by the T-cell line. To validate these results, the T cell epitope of *C. trachomatis* SWIB was identified by epitope mapping using target cells pulsed with a series of overlapping peptides and the T-cell line TCL-8. 3H-thymidine incorporation assays demonstrated that the peptide, referred to as C.t.SWIB 52–67, of SEQ ID NO: 39 gave the strongest proliferation of the TCL-8 line. The homologous peptides corresponding to the SWIB of *C. pneumoniae* sequence (SEQ ID NO: 40), the topoisomerase-SWIB fusion of *C. pneumoniae* (SEQ ID NO: 43) and *C. trachomatis* (SEQ ID NO: 42) as well as the human SWI domain (SEQ ID NO: 41) were synthesized and tested in the above assay. The T-cell line TCL-8 only recognized the *C. trachomatis* peptide of SEQ ID NO: 39 and not the corresponding *C. pneumoniae* peptide (SEQ ID NO: 40), or the other corresponding peptides described above (SEQ ID NO; 41–43).

EXAMPLE 7

Induction of T Cell Proliferation and Interferon-γ Production by Chlamydia Pneumoniae Antigens The ability of recombinant *Chlamydia pneumoniae* antigens to induce T cell proliferation and interferon-γ production is determined as follows.

Proteins are induced by IPTG and purified by Ni-NTA agarose affinity chromatograph (Webb et al., *J. Immunology* 157:5034–5041, 1996). The purified polypeptides are then screened for the ability to induce T-cell proliferation in PBMC preparations. PBMCs from *C. pneumoniae* patients as well as from normal donors whose T-cells are known to proliferate in response to Chlamydia antigens, are cultured in medium comprising RPMI 1640 supplemented with 10% pooled human serum and 50 μg/ml gentamicin. Purified polypeptides are added in duplicate at concentrations of 0.5 to 10 μg/mL. After six days of culture in 96-well round-bottom plates in a volume of 200 μl, 50 μl of medium is removed from each well for determination of IFN-γ levels, as described below. The plates are then pulsed with 1 μCi/well of tritiated thymidine for a further 18 hours, harvested and tritium uptake determined using a gas scintillation counter. Fractions that result in proliferation in both replicates three fold greater than the proliferation observed in cells cultured in medium alone are considered positive.

IFN-γ was measured using an enzyme-linked immunosorbent assay (ELISA). ELISA plates are coated with a mouse monoclonal antibody directed to human IFN-γ (PharMingen, San Diego, Calif.) in PBS for four hours at room temperature. Wells are then blocked with PBS containing 5% (W/V) non-fat dried milk for 1 hour at room temperature. The plates are washed six times in PBS/0.2% TWEEN-20 and samples diluted 1:2 in culture medium in the ELISA plates are incubated overnight at room temperature. The plates are again washed and a polyclonal rabbit anti-human IFN-γ serum diluted 1:3000 in PBS/10% normal goat serum is added to each well. The plates are then incubated for two hours at room temperature, washed and horseradish peroxidase-coupled anti-rabbit IgG (Sigma Chemical So., St. Louis, Mo.) is added at a 1:2000 dilution in PBS/5% non-fat dried milk. After a further two hour incubation at room temperature, the plates are washed and TMB substrate added. The reaction is stopped after 20 min with 1 N sulfuric acid. Optical density is determined at 450 nm using 570 nm as a reference wavelength. Fractions that result in both replicates giving an OD two fold greater than the mean OD from cells cultured in medium alone, plus 3 standard deviations, are considered positive.

Chlamydia-specific T cell lines were generated from donor CP-21 with a positive serum titer against *C. pnuemoniae* by stimulating donor PBMC with either *C. trachomatis* or *C. pneumoniae*-infected monocyte-derived dendritic cells, respectively. T-cells generated against *C. pneumoniae* responded to recombinant *C. pneumoniae*-SWIB but not *C. trachomatis*-SWIB, whereas the T-cell line generated against *C. trachomatis* did not respond to either *C. trachomatis*- or *C. pneumoniae*-SWIB (see FIG. 59). The *C. pneumoniae*-SWIB specific immune response of donor CP-21 confirms the *C. pneumoniae* infection and indicates the elicitation of *C. pneumoniae*-SWIB specific T-cells during in vivo *C. pneumoniae* infection. Epitope mapping of the T-cell response to *C. pneumoniae*-SWIB has shown that Cp-SWIB-specific T-cells responded to the overlapping peptides Cp-SWIB 32–51 (SEQ ID NO: 101) and Cp-SWIB 37–56 (SEQ ID NO: 102), indicating a *C. pneumoniae*-SWIB-specific T-cell epitope Cp-SWIB 37–51 (SEQ ID NO: 100).

In additional experiments, T-cell lines were generated from donor CP1, also a *C. pneumoniae* seropositive donor, by stimulating PBMC with non-infectious elementary bodies from *C. trachomatis* and *C. pneumoniae*, respectively. In particular, proliferative responses were determined by stimulating $2.5 \times 10^4$ T-cells in the presence of $1 \times 10^4$ monocyte-derived dendritic cells and non-infectious elementary bodies derived from *C. trachomatis* and *C. pneumoniae*, or either recombinant *C. trachomatis* or *C. pneumoniae* SWIB protein. The T-cell response against SWIB resembled the data obtained with T-cell lines from CP-21 in that *C. pneumoniae*-SWIB, but not *C. trachomatis*-SWIB elicited a response by the *C. pneumoniae* T-cell line. In addition, the *C. trachomatis* T-cell line did not proliferate in response to either *C. trachomatis* or *C. pneumoniae* SWIB, though it did proliferate in response to both CT and CP elementary bodies.

EXAMPLE 8

Immune Responses of Normal Studu Subjects Against Chlamydia Antigens

The examples provided herein suggest that there is a population of healthy donors among the general population that has been infected with *C. trachomatis* and generated a protective immune response controlling the *C. trachomatis* infection. These donors remained clinically asymptomatic and seronegative for *C. trachomatis*. To characterize the immune reponses of normal donors against chlamydial antigens identified by CD4 expression cloning, PBMC obtained from 12 health donors were tested against a panel of recombinant chlamydial antigens including *C. trachomatis*-, *C. pneumoniae*-SWIB and *C. trachomatis*-, *C. pneumoniae*-S13. The data are summarized in Table I below. All donors were seronegative for *C. trachomatis*, whereas 6/12 had a positive *C. pneumoniae* titer. Using a stimulation index of >4 as a positive response, 11/12 of the subjects responded to *C. trachomatis* elementary bodies and 12/12 responded to *C. pneumoniae* elementary bodies. One donor, AD104, responded to recombinant *C. pneumoniae*-S13 protein, but not to recombinant *C. trachomatis*-S13 protein, indicating a *C. pneumoniae*-specific response. Three out of 12 donors had a *C. trachomatis*-SWIB, but not a *C. pneumoniae*-SWIB specific response, confirming a *C. trachomatis* infection. *C. trachomatis* and *C. pneumoniae*-S13. elicited a response in 8/12 donors suggesting a chlamydial infection. These data demonstrate the ability of SWIB and S13 to elicit a T-cell response in PBMC of normal study subjects.

TABLE I

Immune response of normal study subjects against Chlamydia

| Donor | Sex | Chlamydia IgG titer | CT EB | CP EB | CT Swib | CP Swib | CT S13 | CP S13 |
|---|---|---|---|---|---|---|---|---|
| AD100 | male | negative | ++ | +++ | + | – | ++ | ++ |
| AD104 | female | negative | +++ | ++ | – | – | – | ++ |
| AD108 | male | CP 1:256 | ++ | ++ | + | +/– | + | + |
| AD112 | female | negative | ++ | ++ | + | – | + | – |
| AD120 | male | negative | – | + | – | – | – | – |
| AD124 | female | CP 1:128 | ++ | ++ | – | – | – | – |
| AD128 | male | CP 1:512 | + | ++ | – | – | ++ | + |
| AD132 | female | negative | ++ | ++ | – | – | + | + |
| AD136 | female | CP 1:128 | + | ++ | – | – | +/– | – |
| AD140 | male | CP 1:256 | ++ | ++ | – | – | + | + |
| AD142 | female | CP 1:512 | ++ | ++ | – | – | + | + |
| AD146 | female | negative | ++ | ++ | – | – | ++ | + |

Proliferative responses were determined by stimulating $3 \times 10^5$ PBMC with $1 \times 10^4$ monocyte-derived dendritic cells pre-incubated with the respective recombinant antigens or elementary bodies (EB). Assays were harvested after 6 days with a $^3$H-thymidine pulse for the last 18 h.

SI: Stimulation Index
+/−: SI~4
+: SI>4
++: SI 10–30
+++: SI>30

In a first series of experiments, T-cell lines were generated from a healthy female individual (CT-10) with a history of genital exposure to *C. trachomatis* by stimulating T-cells with *C. trachomatis* LGV II elementary bodies as previously described. Although the study subject was exposed to *C. trachomatis*, she did not seroconvert and did not develop clinical symptoms, suggesting donor CT-10 may have developed a protective immune response against *C. trachomatis*. As shown in FIG. 10, a primary Chlamydia-specific T-cell line derived from donor CT-10 responded to *C. trachomatis*-SWIB, but not *C. pneumoniae*-SWIB recombinant proteins, confirming the exposure of CT-10 to *C. trachomatis*. Epitope mapping of the T-cell response to *C. trachomatis*-SWIB showed that this donor responded to the same epitope Ct-SWIB 52–67 (SEQ ID NO: 39) as T-cell line TCL-8, as shown in FIG. 11.

Although the present invention has been described in some detail by way of illustration and example for purposes of clarity of understanding, changes and modifications can be carried out without departing from the scope of the invention which is intended to be limited only by the scope of the appended claims.

What is claimed is:

1. A method of stimulating an immune response against a Chlamydia antigen in a patient, said method comprising:

(a) providing a phannaceutical composition, wherein said pharmaceutical composition comprises an isolated polypeptide comprising an immunogenic portion of a Chlamydia antigen, wherein said immunogenic portion comprises at least 20 contiguous amino acid residues from SEQ ID NO:5, wherein said antigen comprises the amino acid sequence encoded by a polynucleotide sequence selected from the group consisting of (a) a sequence encoding the polypeptide of SEQ ID NO:5; (b) a sequence 95% identical to a sequence encoding the polypeptide of SEQ ID NO:5; and (c) a sequence that hybridizes with a sequence encoding the polypeptide of SEQ ID NO:5 under moderately stringent conditions, and a physiologically acceptable carrier, wherein the polypeptide encoded by the polynucleotide of (b) or (c) binds to an antibody or T-cell that is specific for the polypeptide of SEQ ID NO:5;

(b) administering said pharmaceutical composition to the patient; and (c) thereby stimulating an immune response in the patient.

2. The method of claim 1, wherein said polypeptide is encoded by a polynucleotide selected from the group consisting of (a) the polynucleotide of SEQ ID NO:1, (b) a polynucleotide at least 95% identical to SEQ ID NO:1; and (c) a polynucleotide that hybridizes with SEQ ID NO:1 under moderately stringent conditions, wherein said polypeptide encoded by the polynucleotide of (b) or (c) binds to an antibody or T-cell that is specific for the polypeptide of SEQ ID NO:5.

3. The method of claim 1, wherein said immunogenic portion comprises SEQ ID NOs:13 or 14.

* * * * *

UNITED STATES PATENT AND TRADEMARK OFFICE
CERTIFICATE OF CORRECTION

PATENT NO.    : 6,555,115 B1
DATED         : April 29, 2003
INVENTOR(S)   : Peter Probst et al.

It is certified that error appears in the above-identified patent and that said Letters Patent is hereby corrected as shown below:

Column 109,
Line 43, phannaceutical" should read -- pharmaceutical --

Signed and Sealed this

Sixteenth Day of September, 2003

JAMES E. ROGAN
*Director of the United States Patent and Trademark Office*